(12) United States Patent
Seth et al.

(10) Patent No.: US 8,278,426 B2
(45) Date of Patent: Oct. 2, 2012

(54) CARBOCYCLIC BICYCLIC NUCLEIC ACID ANALOGS

(75) Inventors: Punit P. Seth, Carlsbad, CA (US); Eric E. Swayze, Encinits, CA (US)

(73) Assignee: Isis Pharmaceuticals, Inc., Carlsbad, CA (US)

(*) Notice: Subject to any disclaimer, the term of this patent is extended or adjusted under 35 U.S.C. 154(b) by 272 days.

(21) Appl. No.: 12/602,993

(22) PCT Filed: Jun. 6, 2008

(86) PCT No.: PCT/US2008/066154
§ 371 (c)(1),
(2), (4) Date: Jun. 2, 2010

(87) PCT Pub. No.: WO2008/154401
PCT Pub. Date: Dec. 18, 2008

(65) Prior Publication Data
US 2010/0233806 A1    Sep. 16, 2010

Related U.S. Application Data

(60) Provisional application No. 60/942,824, filed on Jun. 8, 2007, provisional application No. 60/978,671, filed on Oct. 9, 2007, provisional application No. 60/948,024, filed on Jul. 5, 2007.

(51) Int. Cl.
C07H 19/00 (2006.01)
C07H 21/04 (2006.01)

(52) U.S. Cl. ............ 536/22.1; 536/23.1; 536/24.5; 536/26.1; 536/27.1; 514/42; 514/43; 514/44 A

(58) Field of Classification Search .................. None
See application file for complete search history.

(56) References Cited

U.S. PATENT DOCUMENTS

| | | |
|---|---|---|
| 3,687,808 A | 8/1972 | Merigan et al. |
| 4,415,732 A | 11/1983 | Caruthers et al. |
| 4,458,066 A | 7/1984 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,668,777 A | 5/1987 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,013,830 A | 5/1991 | Ohtsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,069 E | 9/1992 | Koster et al. |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,185,444 A | 2/1993 | Summerton et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,220,007 A | 6/1993 | Pederson et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,432,272 A | 7/1995 | Benner |
| 5,434,257 A | 7/1995 | Matteucci et al. |

(Continued)

FOREIGN PATENT DOCUMENTS

| | | |
|---|---|---|
| WO | WO 94/02499 | 2/1994 |

(Continued)

OTHER PUBLICATIONS

Srivastava et al. (Journal of the American Chemical Society, vol. 129, No. 26, 2007, pp. 8362-8379.*
Albaek et al., "Analogues of a Locked Nucleic Acid with Three-Carbon 2',4'~Linkages: Synthesis by Ring-Closing Metathesis and Influence on Nucleic Acid Duplex Stability and Structure" J. Org. Chem. (2006) 71:7731-7740.
Bass et al., "Double-Stranded RNA as a Template for Gene Silencing" Cell (2000) 101:235-238.
Beaucage et al., "The Functionalization of Oligonucleotides Via Phosphoroamidite Derivatives" Tetrahedron (1993) 49(10):1925-1963.
Beaucage et al., "The Synthesis of Specific Ribonucleotides and Unrelated Phosphorylated Biomolecules by the Phosphoramidite Method" Tetrahedron (1993) 49(46):10441-10488.
Beaucage et al., "Advances in the Synthesis of Oligonucleotides by the Phosphoramidite Approach" Tetrahedron (1992) 48(12):2223-2311.

(Continued)

*Primary Examiner* — Traviss C McIntosh, III
(74) *Attorney, Agent, or Firm* — Isis Pharmaceuticals, Inc.

(57) ABSTRACT

Provided herein are saturated and unsaturated carbocyclic bicyclic nucleosides, oligomeric compounds prepared therefrom and methods of using these oligomeric compounds. The saturated and unsaturated carbocyclic bicyclic nucleosides are useful for enhancing properties of oligomeric compounds including nuclease resistance.

55 Claims, No Drawings

U.S. PATENT DOCUMENTS

| | | | |
|---|---|---|---|
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Misiura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci et al. |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci et al. |
| 5,652,355 A | 7/1997 | Metelev et al. |
| 5,652,356 A | 7/1997 | Agrawal |
| 5,658,873 A | 8/1997 | Bertsch-Frank et al. |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,747 A | 8/1998 | Schally et al. |
| 5,830,653 A | 11/1998 | Froehler et al. |
| 6,005,096 A | 12/1999 | Matteucci et al. |
| 6,268,490 B1 | 7/2001 | Imanishi et al. |
| 6,426,220 B1 | 7/2002 | Bennett et al. |
| 6,600,032 B1 | 7/2003 | Manoharan et al. |
| 6,770,748 B2 | 8/2004 | Imanishi et al. |
| 6,794,499 B2 | 9/2004 | Wengel et al. |
| 7,053,207 B2 | 5/2006 | Wengel |
| 2003/0082807 A1 | 5/2003 | Wengel |
| 2003/0207841 A1 | 11/2003 | Kaneko et al. |
| 2003/0224377 A1 | 12/2003 | Wengel et al. |
| 2004/0014959 A1 | 1/2004 | Sorensen et al. |
| 2004/0143114 A1 | 7/2004 | Imanishi et al. |
| 2004/0192918 A1 | 9/2004 | Imanishi et al. |
| 2004/0219565 A1 | 11/2004 | Kauppinen et al. |
| 2010/0331538 A1* | 12/2010 | Seth et al. ............... 536/24.5 |

FOREIGN PATENT DOCUMENTS

| | | |
|---|---|---|
| WO | WO 94/17093 | 8/1994 |
| WO | WO 02/36743 | 5/2002 |
| WO | WO 2005121372 | 11/2005 |
| WO | WO 2005121371 | 12/2005 |
| WO | WO 2008/111908 | 9/2008 |

OTHER PUBLICATIONS

Chiang et al., "Antisense Oligonucleotides Inhibit Intercellular Adhesion Molecule 1 Expression by Two Distinct Mechanisms" J. Biol. Chem. (1991) 266(27):18162-18171.

Eckstein (ed.), "Oligonucleotides attached to intercalators, photoreactive and cleavage agents" Oligonucleotides and Analogues, a Practical Approach, Oxford University Press, New York (1991).

Elbashir et al., "Duplexes of 21-nucleotide RNAs mediate RNA interference in cultured mammalian cells" Nature (2001) 411:494-498.

Elbashir et al., "RNA interference is mediated by 21- and 22-nucleotide RNAs" Genes Dev. (2001) 15:188-200.

Englisch et al., "Chemically Modified Oligonucleotides as Probes and Inhibitors" Angewandte Chemie, International Edition (1991) 30:613.

Fire et al., "Potent and specific genetic interference by double-stranded RNA in *Caenorhabditis elegans*" Nature (1998) 391:806-811.

Freier et al., "The ups and downs of nucleic acid duplex stability: structure-stability studies on chemically-modified DNA:RNA duplexes" Nucleic Acids Research (1997) 25(22):4429-4443.

Gait et al., "Applications of Chemically Synthesized RNA" in RNA: Protein Interactions, Ed. Smith (1998) 1-36.

Gallo et al., "2'-C-Methyluridine phosphoramidite: a new building block for the preparation of RNA analogues carrying the 2'-hydroxyl group" Tetrahedron (2001) 57:5707-5713.

Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition" Tetrahedron (1998) 54:3607-3630.

Kroschwitz, Tthe Concise Encyclopedia of Polymer Science and Engineering, John Wiley & Sons, 1990, pp. 858-859.

Kumar et al., "The First Analogues of LNA (Locked Nucleic Acids): Phosphorothioate-LNA and 2'-Thio-LNA" Bioorg. Med. Chem. Lett. (1998) 8:2219-2222.

Montgomery et al., "RNAa as a target of double-stranded RNA-mediated genetic interference in *Caenorhabditis elegans*" PNAS (1998) 95:15502-15507.

Nishikura et al., "A Short Primer on RNAi: RNA-Directed RNA Polymerase Acts as a Key Catalyst" Cell (2001) 107:415-416.

Sanghvi etal., Antisense Research and Applications, Crooke & Lebleu ed., CRC Press, 1993, Chapter 15.

Scaringe, "RNA Oligonucleotide Synthesis via 5'-Silyl-2'-Orthoester Chemistry" Methods (2001) 23:206-217.

Singh et al., "LNA (locked nucleic acids): synthesis and high-affinity nucleic acid recognition" Chem. Commun. (1998) 4:455-456.

Singh et al., "Synthesis of 2'-Amino-LNA: A Novel Conformationally Restricted High-Affinity Oligonucleotide Analogue with a Handle" J. Org. Chem. (1998) 63(26):10035-10039.

Srivastava et al., "Five- and Six-Membered Conformationally Locked 2'-4'-Carbocyclic ribo-Thymidines: Synthesis, Structure, and Biochemical Studies" J. Am. Chem. Soc. (2007) 129(26):8362-8379.

Tabara et al., "RNAi in *C. elegans*: Soaking in the Genome Sequence" Science (1998) 282:430-431.

Tijsterman et al., "RNA Helicase MUT-14-Dependent Gene Silencing Triggered in *C. elegans* by Short Antisense RNAs" Science (2002) 295:694-697.

Timmons et al., "Specific interference by ingested dsRNA" Nature (1998) 395:854.

Timmons et al., "Ingestion of bacterially expressed dsRNAs can produce specific and potent genetic interference in *Caenorhabditis elegans*" Gene (2001) 263:103-112.

Tuschl et al., "Targeted mRNA degradation by double-stranded RNA in vitro" Genes Dev. (1999) 13:3191-3197.

Wahlestedt et al., "Potent and nontoxic antisense oligonucleotides containing locked nucleic acids" PNAS (2000) 97(10):5633-5638.

Wengel et al., "Chemistry of Locked Nucleic Acids (LNA): Design, Synthesis, and Bio-Physical Properties" International Journal of Peptide Research and Therapeutics (2003) 10(3-4):237-253.

International Search Report for application No. PCT/US2008/066154 dated Jan. 7, 2009.

* cited by examiner

CARBOCYCLIC BICYCLIC NUCLEIC ACID ANALOGS

CROSS-REFERENCE TO RELATED APPLICATIONS

This application is a national phase entry pursuant to 35 U.S.C. §371 of International Application No. PCT/US2008/066154, filed Jun. 6, 2008, which claims priority benefit to the following U.S. Provisional Applications: No. 60/942,824, filed Jun. 8, 2007, entitled "Carbocyclic Bicyclic Nucleic Acid Analogs"; No. 60/978,671, filed Oct. 9, 2007, entitled, "Carbocyclic Bicyclic Nucleic Acid Analogs"; and 60/948,024, filed Jul. 5, 2007, entitled, "Unsaturated Carbocyclic Bicyclic Nucleic Acid Analogs"; the entirety of each disclosure is incorporated herein by reference.

SEQUENCE LISTING

The present application is being filed along with a Sequence Listing in electronic format. The Sequence Listing is provided as a file entitled CHEM0038WOSEQ.txt, created on Jun. 6, 2008 which is 5.11 Kb in size. The information in the electronic format of the sequence listing is incorporated herein by reference in its entirety.

FIELD OF THE INVENTION

Provided herein are carbocyclic bicyclic nucleosides, oligomeric compounds prepared therefrom and methods of using these oligomeric compounds. The saturated and unsaturated carbocyclic bicyclic nucleosides are useful for enhancing properties of oligomeric compounds including nuclease resistance. In certain embodiments, the oligomeric compounds and compositions hybridize to a portion of a target RNA resulting in loss of normal function of the target RNA.

BACKGROUND OF THE INVENTION

Antisense technology is an effective means for reducing the expression of one or more specific gene products and can therefore prove to be uniquely useful in a number of therapeutic, diagnostic, and research applications. Chemically modified nucleosides are routinely used for incorporation into antisense sequences to enhance one or more properties such as for example nuclease resistance. One such group of chemical modifications includes bicyclic nucleosides wherein the furanose portion of the nucleoside includes a bridge connecting two atoms on the furanose ring thereby forming a bicyclic ring system. Such bicyclic nucleosides have various names including BNA's and LNA's for bicyclic nucleic acids or locked nucleic acids respectively.

Various BNA's have been prepared and reported in the patent literature as well as in scientific literature, see for example: Singh et al., Chem. Commun., 1998, 4, 455-456; Koshkin et al., Tetrahedron, 1998, 54, 3607-3630; Wahlestedt et al., Proc. Natl. Acad. Sci. U.S.A., 2000, 97, 5633-5638; Kumar et al., Bioorg. Med. Chem. Lett., 1998, 8, 2219-2222; Wengel et al., PCT International Application WO 98-DK393 19980914; Singh et al., J. Org. Chem., 1998, 63, 10035-10039, the text of each is incorporated by reference herein, in their entirety. Examples of issued US patents and published applications include for example: U.S. Pat. Nos. 7,053,207, 6,770,748, 6,268,490 and 6,794,499 and published U.S. applications 20040219565, 20040014959, 20030207841, 20040192918, 20030224377, 20040143114 and 20030082807; the text of each is incorporated by reference herein, in their entirety.

Many LNA's are toxic. See, e.g., Swayze, E. E.; Siwkowski, A. M.; Wancewicz, E. V.; Migawa, M. T.; Wyrzykiewicz, T. K.; Hung, G.; Monia, B. P.; Bennett, C. F., Antisense oligonucleotides containing locked nucleic acid improve potency but cause significant hepatotoxicity in animals. Nucl. Acids Res., doi: 10.1093/nar/gkl1071 (December 2006, advanced online publication).

One carbocyclic BNA has been previously reported (Frier et al., Nucleic Acids Research, 1997, 25 (22), 4429-4443) having a 4'-(CH$_2$)$_3$-2' bridge. This modification was reported to drop the Tm about 2.5° C. per modification for a poly T oligomer having a BNA T nucleoside in place of one or more T nucleosides when hybridized to complementary RNA. This same BNA having the 4'-(CH$_2$)$_3$-2' bridge as reported by Frier et al., or the alkenyl analog bridge 4'-CH=CH—CH$_2$-2' has also been reported to have increased stability with an increased Tm of from about 2.5 to 5.0° C. per modification (see Albaek et al., J. Org. Chem., 2006, 71, 7731-7740).

Carbocyclic bicyclic nucleosides and oligonucleotides prepared therefrom have been recently reported by Srivastava et al., J. Am. Chem. Soc. 2007, 129(26), 8362-8379, published on line on Jun. 7, 2007.

There remains a long-felt need for agents that specifically regulate gene expression via antisense mechanisms. Disclosed herein are carbocyclic BNA's and antisense compounds prepared therefrom useful for modulating gene expression pathways, including those relying on mechanisms of action such as RNaseH, RNAi and dsRNA enzymes, as well as other antisense mechanisms based on target degradation or target occupancy. One having skill in the art, once armed with this disclosure will be able, without undue experimentation, to identify, prepare and exploit antisense compounds for these uses.

BRIEF SUMMARY OF THE INVENTION

Provided herein are bicyclic nucleosides, oligomeric compounds comprising the bicyclic nucleosides and methods of using the oligomeric compounds. In certain embodiments, the bicyclic nucleosides impart enhanced properties to oligomeric compounds they are incorporated into.

The variables are defined individually in further detail herein. It is to be understood that the bicyclic nucleosides, oligomer compounds, and methods of use thereof provided herein include all combinations of the embodiments disclosed and variables defined herein.

In certain embodiments, bicyclic nucleosides are provided here having Formula I:

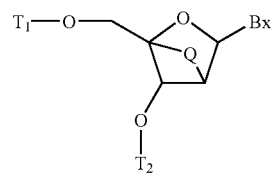

wherein:

Bx is a heterocyclic base moiety;

one of T$_1$ and T$_2$ is H or a hydroxyl protecting group and the other of T$_1$ and T$_2$ is H, a hydroxyl protecting group or a reactive phosphorus group;

Q is C(q$_1$)(q$_2$)C(q$_3$)(q$_4$), C(q$_1$)=C(q$_3$), C[=C(q$_1$)(q$_2$)]-C(q$_3$)(q$_4$) or C(q$_1$)(q$_2$)-C[=C(q$_3$)(q$_4$)];

q$_1$, q$_2$, q$_3$ and q$_4$ are each, independently, H, halogen, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_1$-C$_{12}$ alkoxy, substituted C$_1$-C$_{12}$ alkoxy, OJ$_1$, SJ$_1$, SOJ$_1$, SO$_2$J$_1$, NJ$_1$J$_2$, N$_3$, CN, C(=O)OJ$_1$, C(=O)—NJ$_1$J$_2$, C(=O)J$_1$, O—C(=O)NJ$_1$J$_2$, N(H)C(=NH)NJ$_1$J$_2$, N(H)C(=O)NJ$_1$J$_2$ or N(H)C(=S)NJ$_1$J$_2$;

wherein each substituted group is, independently, mono or poly substituted with substituent groups independently selected from halogen, $OJ_1$, $SJ_1$, $NJ_1J_2$, $N_3$, CN, $C(=O)OJ_1$, $C(=O)NJ_1J_2$, $C(=O)J_1$, $O-C(=O)NJ_1J_2$, $N(H)C(=O)NJ_1J_2$ or $N(H)C(=S)NJ_1J_2$;

each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group; and wherein when Q is $C(q_1)(q_2)C(q_3)(q_4)$ and one of $q_3$ or $q_4$ is $CH_3$ then at least one of the other of $q_3$ or $q_4$ or one of $q_1$ and $q_2$ is other than H.

In certain embodiments, the bicyclic nucleosides have Formula II:

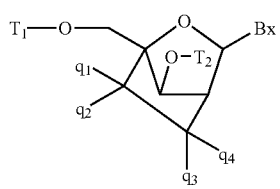

II wherein:

Bx is a heterocyclic base moiety; one of $T_1$ and $T_2$ is H or a hydroxyl protecting group and the other of $T_1$ and $T_2$ is H, a hydroxyl protecting group or a reactive phosphorus group;

each $q_1$, $q_2$, $q_3$ and $q_4$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_1$, $SJ_1$, $SOJ_1$, $SO_2J_1$, $NJ_1J_2$, $N_3$, CN, $C(=O)OJ_1$, $C(=O)NJ_1J_2$, $C(=O)J_1$, $O-C(=O)NJ_1J_2$, $N(H)C(=NH)NJ_1J_2$, $N(H)C(=O)NJ_1J_2$ or $N(H)C(=S)NJ_1J_2$;

wherein each substituted group is, independently, mono or poly substituted with substituent groups independently selected from halogen, $C_1$-$C_6$ alkyl, $C_2$-$C_6$ alkenyl, $C_2$-$C_6$ alkynyl, $OJ_1$, $SJ_1$, $NJ_1J_2$, $N_3$, CN, $C(=O)OJ_1$, $C(=O)NJ_1J_2$, $C(=O)J_1$, $O-C(=O)NJ_1J_2$, $N(H)C(=O)-NJ_1J_2$ or $N(H)C(=S)NJ_1J_2$;

each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group; and wherein when one of $q_3$ or $q_4$ is $CH_3$ then at least one of the other of $q_3$ or $q_4$ or one of $q_1$ and $q_2$ is other than H.

In certain embodiments, bicyclic nucleosides having Formula II are provided wherein $q_1$, $q_2$, $q_3$ and $q_4$ are each H. In certain embodiments, three of $q_1$, $q_2$, $q_3$ and $q_4$ are each H and the other one of $q_1$, $q_2$, $q_3$ and $q_4$ is other than H. In certain embodiments, three of $q_1$, $q_2$, $q_3$ and $q_4$ are each H and the other one of $q_1$, $q_2$, $q_3$ and $q_4$ is halogen, $C_1$-$C_6$ alkyl, substituted $C_1$-$C_6$ alkyl, $C_1$-$C_6$ alkoxy, substituted $C_1$-$C_6$ alkoxy, $OJ_1$, $SJ_1$, $NJ_1J_2$ or CN. In certain embodiments, three of $q_1$, $q_2$, $q_3$ and $q_4$ are each H and the other one of $q_1$, $q_2$, $q_3$ and $q_4$ is halogen, $C_1$-$C_6$ alkyl or $C_1$-$C_6$ alkoxy. In certain embodiments, three of $q_1$, $q_2$, $q_3$ and $q_4$ are each H and the other one of $q_1$, $q_2$, $q_3$ and $q_4$ is $CH_3$ or F.

In certain embodiments, bicyclic nucleosides having Formula II are provided wherein two of $q_1$, $q_2$, $q_3$ and $q_4$ are each H and the other two of $q_1$, $q_2$, $q_3$ and $q_4$ are each other than H. In certain embodiments, two of $q_1$, $q_2$, $q_3$ and $q_4$ are each H and the other two of $q_1$, $q_2$, $q_3$ and $q_4$ are each, independently, halogen, $C_1$-$C_6$ alkyl, substituted $C_1$-$C_6$ alkyl, $C_1$-$C_6$ alkoxy, substituted $C_1$-$C_6$ alkoxy, $OJ_1$, $SJ_1$, $NJ_1J_2$ or CN. In certain embodiments, bicyclic nucleosides having Formula II are provided wherein two of $q_1$, $q_2$, $q_3$ and $q_4$ are each H and the other two of $q_1$, $q_2$, $q_3$ and $q_4$ are each, independently, halogen $C_1$-$C_6$ alkyl or $C_1$-$C_6$ alkoxy. In certain embodiments, bicyclic nucleosides having Formula II are provided wherein two of $q_1$, $q_2$, $q_3$ and $q_4$ are each H and the other two of $q_1$, $q_2$, $q_3$ and $q_4$ are each, independently, $CH_3$ or F.

In certain embodiments, bicyclic nucleosides having Formula II are provided wherein one of $q_1$ and $q_2$ is H and one of $q_3$ and $q_4$ is H or both of $q_1$ and $q_2$ are H or both of $q_3$ and $q_4$ are H and the other two of $q_1$, $q_2$, $q_3$ and $q_4$ are other than H. In certain embodiments, one of $q_1$ and $q_2$ is H and one of $q_3$ and $q_4$ is H or both of $q_1$ and $q_2$ are H or both of $q_3$ and $q_4$ are H and the other two of $q_1$, $q_2$, $q_3$ and $q_4$ are other than H and are different one from the other.

In certain embodiments, bicyclic nucleosides having Formula II are provided wherein one of $q_1$ and $q_2$ is H, one of $q_3$ and $q_4$ is H and the other two of $q_1$, $q_2$, $q_3$ and $q_4$ are each, independently, $C_1$-$C_6$ alkyl or F. In certain embodiments, one of $q_1$ and $q_2$ is H, one of $q_3$ and $q_4$ is H and the other two of $q_1$, $q_2$, $q_3$ and $q_4$ are each, independently, a hydroxyl protecting group.

In certain embodiments, bicyclic nucleosides having Formula II are provided wherein each of the hydroxyl protecting groups is, independently, selected from acetyl, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, benzoyl, p-phenylbenzoyl, 2,6-dichlorobenzyl, diphenylmethyl, p-nitrobenzyl, trimethylsilyl, triethylsilyl, t-butyldimethylsilyl, t-butyldiphenylsilyl, triphenylsilyl, triisopropylsilyl, benzoylformate, chloroacetyl, trichloroacetyl, trifluoroacetyl, pivaloyl, 9-fluorenylmethyl carbonate, mesylate, tosylate, triflate, trityl, monomethoxytrityl, dimethoxytrityl, trimethoxytrityl and substituted pixyl.

In certain embodiments, bicyclic nucleosides having Formula II are provided wherein $T_1$ is acetyl, benzyl, t-butyldimethylsilyl, t-butyldiphenylsilyl or dimethoxytrityl. In certain embodiments, $T_1$ is 4,4'-dimethoxytrityl. In certain embodiments, $T_2$ is a reactive phosphorus group. In certain embodiments, the reactive phosphorus group is diisopropylcyanoethoxy phosphoramidite or H-phosphonate. In certain embodiments, $T_1$ is 4,4'-dimethoxytrityl and $T_2$ is diisopropylcyanoethoxy phosphoramidite.

In certain embodiments, bicyclic nucleosides having Formula II are provided wherein Bx is a pyrimidine, substituted pyrimidine, purine, or substituted purine. In certain embodiments, Bx is uracil, 5-methyluracil, 5-propynyl-uracil, 5-thiazolo-uracil, thymine, cytosine, 5-methyl-cytosine, 5-propynyl-cytosine, 5-thiazolo-cytosine, adenine, guanine or 2,6-diaminopurine.

In certain embodiments, bicyclic nucleosides having Formula II are provided wherein each hand $J_1$ and $J_2$ is, independently, H or $C_1$-$C_3$ alkyl.

In certain embodiments, bicyclic nucleosides having Formula II are provided further having the configuration of Formula III:

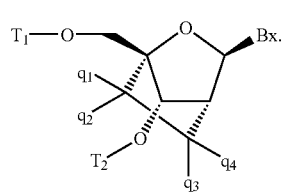

III

In certain embodiments, oligomeric compounds are provided comprising at least one bicyclic nucleoside having Formula IV:

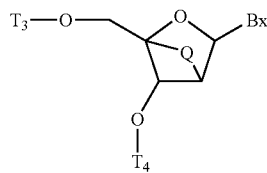

wherein independently for each of said at least one bicyclic nucleoside having Formula IV:

Bx is a heterocyclic base moiety;

$T_3$ and $T_4$ are each, independently, an internucleoside linking group linking the bicyclic nucleoside having Formula IV to the oligomeric compound or one of $T_3$ and $T_4$ is an internucleoside linking group linking the bicyclic nucleoside having Formula IV to the oligomeric compound and the other of $T_3$ and $T_4$ is H, a hydroxyl protecting group, a linked conjugate group or a 5' or 3'-terminal group;

Q is $C(q_1)(q_2)C(q_3)(q_4)$, $C(q_1)=C(q_3)$, $C[=C(q_1)(q_2)]-C(q_3)(q_4)$ or $C(q_1)(q_2)-C[=C(q_3)(q_4)]$;

$q_1$, $q_2$, $q_3$ and $q_4$ are each, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_1$, $SJ_1$, $SOJ_1$, $SO_2J_1$, $NJ_1J_2$, $N_3$, CN, $C(=O)OJ_1$, $C(=O)NJ_1J_2$, $C(=O)J_1$, $O-C(=O)NJ_1J_2$, $N(H)C(=NH)NJ_1J_2$, $N(H)C(=O)NJ_1J_2$ or $N(H)C(=S)NJ_1J_2$;

wherein each substituted group is, independently, mono or poly substituted with substituent groups independently selected from halogen, $C_1$-$C_6$ alkyl, $C_2$-$C_6$ alkenyl, $C_2$-$C_6$ alkynyl, $OJ_1$, $SJ_1$, $NJ_1J_2$, $N_3$, CN, $C(=O)OJ_1$, $C(=O)NJ_1J_2$, $C(=O)J_1$, $O-C(=O)NJ_1J_2$, $N(H)C(=O)-NJ_1J_2$ or $N(H)C(=S)NJ_1J_2$; and each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group; and wherein when Q is $C(q_1)(q_2)C(q_3)(q_4)$ and one of $q_3$ or $q_4$ is $CH_3$ then at least one of the other of $q_3$ or $q_4$ or one of $q_1$ and $q_2$ is other than H.

In certain embodiments, oligomeric compounds are provided comprising at least one bicyclic nucleoside having Formula V:

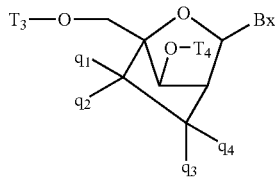

wherein independently for each of said at least one bicyclic nucleoside having Formula V:

Bx is a heterocyclic base moiety;

$T_3$ and $T_4$ are each, independently, an internucleoside linking group linking the bicyclic nucleoside having Formula V to the oligomeric compound or one of $T_3$ and $T_4$ is an internucleoside linking group linking the bicyclic nucleoside having Formula V to the oligomeric compound and the other of $T_3$ and $T_4$ is H, a hydroxyl protecting group, a linked conjugate group or a 5' or 3'-terminal group;

each $q_1$, $q_2$, $q_3$ and $q_4$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_1$, $SJ_1$, $SOJ_1$, $SO_2J_1$, $NJ_1J_2$, $N_3$, CN, $C(=O)OJ_1$, $C(=O)NJ_1J_2$, $O-C(=O)NJ_1J_2$, $N(H)C(=NH)NJ_1J_2$, $N(H)C(=O)NJ_1J_2$ or $N(H)C(=S)NJ_1J_2$;

wherein each substituted group is, independently, mono or poly substituted with substituent groups independently selected from halogen, $C_1$-$C_6$ alkyl, $C_2$-$C_6$ alkenyl, $C_2$-$C_6$ alkynyl, $OJ_1$, $SJ_1$, $NJ_1J_2$, $N_3$, CN, $C(=O)OJ_1$, $C(=O)NJ_1J_2$, $C(=O)J_1$, $O-C(=O)NJ_1J_2$, $N(H)C(=O)-NJ_1J_2$ or $N(H)C(=S)NJ_1J_2$;

each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group; and wherein when one of $q_3$ or $q_4$ is $CH_3$ then at least one of the other of $q_3$ or $q_4$ or one of $q_1$ and $q_2$ is other than H.

In certain embodiments, oligomeric compounds comprising at least one bicyclic nucleoside having Formula V are provided wherein each of $q_1$, $q_2$, $q_3$ and $q_4$ is H. In certain embodiments, three of $q_1$, $q_2$, $q_3$ and $q_4$ are each H and the other one of $q_1$, $q_2$, $q_3$ and $q_4$ is H. In certain embodiments, three of $q_1$, $q_2$, $q_3$ and $q_4$ are each H and the other one of $q_1$, $q_2$, $q_3$ and $q_4$ is halogen, $C_1$-$C_6$ alkyl, substituted $C_1$-$C_6$ alkyl, $C_1$-$C_6$ alkoxy, substituted $C_1$-$C_6$ alkoxy, $OJ_1$, $SJ_1$, $NJ_1J_2$ or CN. In certain embodiments, three of $q_1$, $q_2$, $q_3$ and $q_4$ are each H and the other one of $q_1$, $q_2$, $q_3$ and $q_4$ is halogen $C_1$-$C_6$ alkyl or $C_1$-$C_6$ alkoxy. In certain embodiments, three of $q_1$, $q_2$, $q_3$ and $q_4$ are each H and the other one of $q_1$, $q_2$, $q_3$ and $q_4$ is $CH_3$ or F.

In certain embodiments, oligomeric compounds comprising at least one bicyclic nucleoside having Formula V are provided wherein two of $q_1$, $q_2$, $q_3$ and $q_4$ are each H and the other two of $q_1$, $q_2$, $q_3$ and $q_4$ are each, independently, halogen, $C_1$-$C_6$ alkyl, substituted $C_1$-$C_6$ alkyl, $C_1$-$C_6$ alkoxy, substituted $C_1$-$C_6$ alkoxy, $OJ_1$, $SJ_1$, $NJ_1J_2$ or CN. In certain embodiments, two of $q_1$, $q_2$, $q_3$ and $q_4$ are each H and the other two of $q_1$, $q_2$, $q_3$ and $q_4$ are each, independently, halogen, $C_1$-$C_6$ alkyl, substituted $C_1$-$C_6$ alkyl, $C_1$-$C_6$ alkoxy, substituted $C_1$-$C_6$ alkoxy or $OJ_1$. In certain embodiments, two of $q_1$, $q_2$, $q_3$ and $q_4$ are each H and the other two of $q_1$, $q_2$, $q_3$ and $q_4$ are each, independently, halogen $C_1$-$C_6$ alkyl or $C_1$-$C_6$ alkoxy. In certain embodiments, two of $q_1$, $q_2$, $q_3$ and $q_4$ are each H and the other two of $q_1$, $q_2$, $q_3$ and $q_4$ are each, independently, $CH_3$ or F.

In certain embodiments, oligomeric compounds comprising at least one bicyclic nucleoside having Formula V are provided wherein one of $q_1$ and $q_2$ is H and one of $q_3$ and $q_4$ is H or both of $q_1$ and $q_2$ are H or both of $q_3$ and $q_4$ are H and the other two of $q_1$, $q_2$, $q_3$ and $q_4$ are other than H. In certain embodiments, one of $q_1$ and $q_2$ is H and one of $q_3$ and $q_4$ is H or both of $q_1$ and $q_2$ are H or both of $q_3$ and $q_4$ are H and the other two of $q_1$, $q_2$, $q_3$ and $q_4$ are other than H and are different one from the other.

In certain embodiments, oligomeric compounds comprising at least one bicyclic nucleoside having Formula V are provided wherein one of $q_1$ and $q_2$ and one of $q_3$ and $q_4$ is H and the other two of $q_1$, $q_2$, $q_3$ and $q_4$ are each, independently, $C_1$-$C_6$ alkyl or F.

In certain embodiments, oligomeric compounds comprising at least one bicyclic nucleoside having Formula V are provided wherein one $T_3$ is H or a hydroxyl protecting group. In certain embodiments, at least one $T_3$ is an internucleoside linking group. In certain embodiments, one $T_4$ is H or a hydroxyl protecting group. In certain embodiments, at least one $T_4$ is an internucleoside linking group. In certain embodiments, at least one of $T_3$ and $T_4$ is a 3' or 5'-terminal group.

In certain embodiments, oligomeric compounds comprising at least one bicyclic nucleoside having Formula V are provided wherein each internucleoside linking group is, independently, a phosphodiester or phosphorothioate. In certain embodiments, each internucleoside linking group is a phosphorothioate.

In certain embodiments, oligomeric compounds are provided comprising at least one bicyclic nucleoside having Formula V wherein each bicyclic nucleoside of Formula V further has the configuration of Formula VI:

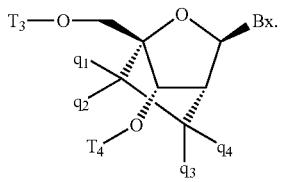

VI

In certain embodiments, oligomeric compounds comprising at least one bicyclic nucleoside having Formula V are provided comprising at least one region of at least two contiguous bicyclic nucleosides having Formula V. In certain embodiments, at least one of the regions of at least two contiguous bicyclic nucleosides having Formula V is located at the 3' or the 5'-end of the oligomeric compound. In certain embodiments, at least one of the regions of at least two contiguous bicyclic nucleosides having Formula V is located at the 3' or the 5'-end of the oligomeric compound and at least one bicyclic nucleoside having Formula V located at the other of the 3' or the 5'-end of the oligomeric compound.

In certain embodiments, oligomeric compounds are provided comprising a gapped motif having an internal region of from about 6 to about 14 monomeric subunits separating two external regions independently comprising from 1 to about 5 contiguous bicyclic nucleosides having Formula V. In certain embodiments, essentially each monomeric subunit in the internal region is a β-D-2'-deoxyribonucleoside. In certain embodiments, the internal region comprises from about 8 to about 14 β-D-2'-deoxyribonucleosides. In certain embodiments, the internal region comprises from about 10 to about 14 β-D-2'-deoxyribonucleosides. In certain embodiments, the internal region comprises from about 10 to about 12 β-D-2'-deoxyribonucleosides. In certain embodiments, each external region independently comprises from 2 to about 3 bicyclic nucleosides having Formula V. In certain embodiments, each external region independently comprises 2 bicyclic nucleosides having Formula V. In certain embodiments, each external region independently comprises 2 bicyclic nucleosides having Formula V and the internal region comprises 10 β-D-2'-deoxyribonucleosides. In certain embodiments, each external region independently comprises from 2 to about 3 bicyclic nucleosides having Formula V and the internal region comprises 14 β-D-2'-deoxyribonucleosides. In certain embodiments, each external region independently comprises 2 bicyclic nucleosides having Formula V and the internal region comprises 14 β-D-2'-deoxyribonucleosides.

In certain embodiments, oligomeric compounds are provided comprising a gapped motif having an internal region of from about 6 to about 14 monomeric subunits separating two external regions independently comprising from 1 to about 5 contiguous bicyclic nucleosides having Formula V wherein each bicyclic nucleoside of Formula V has the configuration of Formula VI:

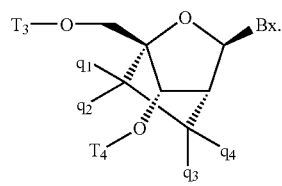

VI

In certain embodiments, oligomeric compounds comprising at least one bicyclic nucleoside having Formula V are provided comprising from about 8 to about 40 monomer subunits in length. In certain embodiments, oligomeric compounds comprising at least one bicyclic nucleoside having Formula V are provided comprising from about 8 to about 20 monomer subunits in length. In certain embodiments, oligomeric compounds comprising at least one bicyclic nucleoside having Formula V are provided comprising from about 10 to about 16 monomer subunits in length. In certain embodiments, oligomeric compounds comprising at least one bicyclic nucleoside having Formula V are provided comprising from about 10 to about 14 monomer subunits in length.

In certain embodiments, methods of reducing target messenger RNA are provided comprising contacting one or more cells, a tissue or an animal with an oligomeric compound comprising at least one bicyclic nucleoside having Formula V.

In certain embodiments, bicyclic nucleosides are provided having Formula VII:

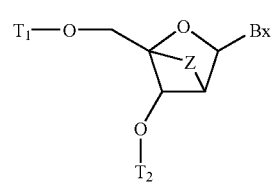

VII wherein:

Bx is a heterocyclic base moiety;

one of $T_1$ and $T_2$ is H or a hydroxyl protecting group and the other of $T_1$ and $T_2$ is H, a hydroxyl protecting group or a reactive phosphorus group;

Z is $C(q_1)=C(q_3)$, $C[=C(q_1)(q_2)]-C(q_3)(q_4)$ or $C(q_1)(q_2)-C[=C(q_3)(q_4)]$;

$q_1$, $q_2$, $q_3$ and $q_4$ are each, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_1$, $SJ_1$, $SOJ_1$, $SO_2J_1$, $NJ_1J_2$, $N_3$, CN, $C(=O)OJ_1$, $C(=O)NJ_1J_2$, $C(=O)J_1$, O—$C(=O)NJ_1J_2$, $N(H)C(=NH)NJ_1J_2$, $N(H)C(=O)NJ_1J_2$ or $N(H)C(=S)NJ_1J_2$;

wherein each substituted group is, independently, mono or poly substituted with substituent groups independently selected from halogen, $C_1$-$C_6$ alkyl, $C_2$-$C_6$ alkenyl, $C_2$-$C_6$ alkynyl, $OJ_1$, $SJ_1$, $NJ_1J_2$, $N_3$, CN, $C(=O)OJ_1$, $C(=O)NJ_1J_2$, $C(=O)J_1$, O—$C(=O)NJ_1J_2$, $N(H)C(=O)$—$NJ_1J_2$ or $N(H)C(=S)NJ_1J_2$; and each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group.

In certain embodiments, bicyclic nucleosides are provided having Formula VII wherein Z is $C(q_1)=C(q_3)$. In certain embodiments, Z is $C[=C(q_1)(q_2)]-C(q_3)(q_4)$. In certain embodiments, Z is $C(q_1)(q_2)-C[=C(q_3)(q_4)]$.

In certain embodiments, bicyclic nucleosides are provided having Formula VII wherein $q_1$, $q_2$, $q_3$ and $q_4$ are each H.

In certain embodiments, bicyclic nucleosides are provided having Formula VII wherein Z is $C[=C(q_1)(q_2)]-C(q_3)(q_4)$ or $C(q_1)(q_2)-C[=C(q_3)(q_3)]$ and three of $q_1$, $q_2$, $q_3$ and $q_4$ are H and the other one of $q_1$, $q_2$, $q_3$ and $q_4$ is other than H. In certain embodiments, the other one of $q_1$, $q_2$, $q_3$ and $q_4$ is halogen, $C_1$-$C_6$ alkyl, substituted $C_1$-$C_6$ alkyl, $C_1$-$C_6$ alkoxy, substituted $C_1$-$C_6$ alkoxy, $OJ_1$, $SJ_1$, $NJ_1J_2$ or CN. In certain embodiments, the other one of $q_1$, $q_2$, $q_3$ and $q_4$ is halogen, $C_1$-$C_6$ alkyl or $C_1$-$C_6$ alkoxy. In certain embodiments, the other one of $q_1$, $q_2$, $q_3$ and $q_4$ is fluoro or methyl.

In certain embodiments, bicyclic nucleosides are provided having Formula VII wherein Z is $C[=C(q_1)(q_2)]-C(q_3)(q_4)$ or $C(q_1)(q_2)-C[=C(q_3)(q_3)]$ and two of $q_1$, $q_2$, $q_3$ and $q_4$ are H and the other two of $q_1$, $q_2$, $q_3$ and $q_4$ are other than H. In certain embodiments, the other two of $q_1$, $q_2$, $q_3$ and $q_4$ are independently, halogen, $C_1$-$C_6$ alkyl, substituted $C_1$-$C_6$ alkyl, $C_1$-$C_6$ alkoxy, substituted $C_1$-$C_6$ alkoxy, $OJ_1$, $SJ_1$, $NJ_1J_2$ or CN. In certain embodiments, the other two of $q_1$, $q_2$, $q_3$ and $q_4$ are independently, halogen, $C_1$-$C_6$ alkyl or $C_1$-$C_6$ alkoxy. In certain embodiments, the other two of $q_1$, $q_2$, $q_3$ and $q_4$ are independently, fluoro or methyl. In certain embodiments, $q_1$ and $q_2$ are each H. In certain embodiments, $q_3$ and $q_4$ are each H. In certain embodiments, one of $q_1$ and $q_2$ is H and one of $q_3$ and $q_4$ is H.

In certain embodiments, bicyclic nucleosides are provided having Formula VII wherein only one of $q_1$, $q_2$, $q_3$ and $q_4$ is H. In certain embodiments, three of $q_1$, $q_2$, $q_3$ and $q_4$ are each, independently, halogen, $OJ_1$, $C_1$-$C_6$ alkyl, substituted $C_1$-$C_6$ alkyl, $C_1$-$C_6$ alkoxy, substituted $C_1$-$C_6$ alkoxy, $OJ_1$, $SJ_1$, $NJ_1J_2$ or CN. In certain embodiments, three of $q_1$, $q_2$, $q_3$ and $q_4$ are each, independently, halogen, hydroxyl, $C_1$-$C_6$ alkyl or $C_1$-$C_6$ alkoxy. In certain embodiments, the other three of $q_1$, $q_2$, $q_3$ and $q_4$ are each, independently, fluoro or methyl.

In certain embodiments, bicyclic nucleosides are provided having Formula VII wherein Z is $C(q_1)=C(q_3)$ and one of $q_1$ and $q_3$ is H and the other of $q_1$ and $q_3$ is other than H. In certain embodiments, the other of $q_1$ and $q_3$ is halogen, $OJ_1$, $C_1$-$C_6$ alkyl, substituted $C_1$-$C_6$ alkyl, $C_1$-$C_6$ alkoxy, substituted $C_1$-$C_6$ alkoxy, $OJ_1$, $SJ_1$, $NJ_1J_2$ or CN. In certain embodiments, the other of $q_1$ and $q_3$ is halogen, $C_1$-$C_6$ alkyl or $C_1$-$C_6$ alkoxy. In certain embodiments, the other of $q_1$ and $q_3$ is fluoro or methyl.

In certain embodiments, bicyclic nucleosides are provided having Formula VII wherein Z is $C(q_1)=C(q_3)$ and $q_1$ and $q_3$ are both other than H. In certain embodiments, $q_1$ and $q_3$ are each, independently, halogen, $C_1$-$C_6$ alkyl, substituted $C_1$-$C_6$ alkyl, $C_1$-$C_6$ alkoxy, substituted $C_1$-$C_6$ alkoxy, $OJ_1$, $SJ_1$, $NJ_1J_2$ or CN. In certain embodiments, $q_1$ and $q_3$ are each, independently, halogen, $C_1$-$C_{12}$ alkyl or $C_1$-$C_6$ alkoxy. In certain embodiments, $q_1$ and $q_3$ are each, independently, fluoro or methyl.

In certain embodiments, bicyclic nucleosides are provided having Formula VII wherein $T_1$ and $T_2$ are each, independently, a hydroxyl protecting group. In certain embodiments, each of the hydroxyl protecting groups is, independently, selected from acetyl, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, benzoyl, p-phenylbenzoyl, 2,6-dichlorobenzyl, diphenylmethyl, p-nitrobenzyl, trimethylsilyl, triethylsilyl, t-butyldimethylsilyl, t-butyldiphenylsilyl, triphenylsilyl, tri-isopropylsilyl, benzoylformate, chloroacetyl, trichloroacetyl, trifluoroacetyl, pivaloyl, 9-fluorenylmethyl carbonate, mesylate, tosylate, triflate, trityl, monomethoxytrityl, dimethoxytrityl, trimethoxytrityl and substituted pixyl.

In certain embodiments, bicyclic nucleosides are provided having Formula VII wherein $T_1$ is acetyl, benzyl, t-butyldimethylsilyl, t-butyldiphenylsilyl or 4,4'-dimethoxytrityl. In certain embodiments, $T_2$ is a reactive phosphorus group. In certain embodiments, $T_2$ is diisopropyl-cyanoethoxy phosphoramidite or H-phosphonate. In certain embodiments, $T_2$ is diisopropyl-cyanoethoxy phosphoramidite. In certain embodiments, $T_2$ is diisopropylcyanoethoxy phosphoramidite and $T_1$ is 4,4'-dimethoxytrityl.

In certain embodiments, bicyclic nucleosides are provided having Formula VII wherein Bx is a pyrimidine, substituted pyrimidine, purine, or substituted purine. In certain embodiments, Bx is uracil, 5-methyluracil, 5-propynyl-uracil, 5-thiazolo-uracil, thymine, cytosine, 5-methylcytosine, 5-propynyl-cytosine, 5-thiazolo-cytosine, adenine, guanine or 2,6-diaminopurine.

In certain embodiments, bicyclic nucleosides are provided having Formula VII wherein each $J_1$ and $J_2$ is, independently, H or $C_1$-$C_3$ alkyl.

In certain embodiments, bicyclic nucleosides are provided having Formula VII wherein each bicyclic nucleoside of Formula VII further has the configuration of Formula VIII:

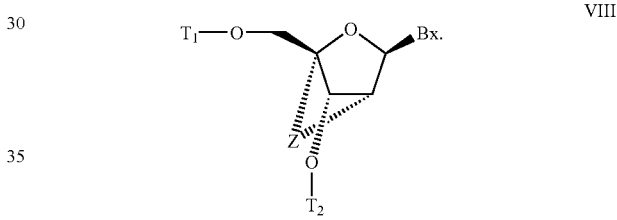

VIII

In certain embodiments, oligomeric compounds are provided comprising at least one bicyclic nucleoside having Formula IX:

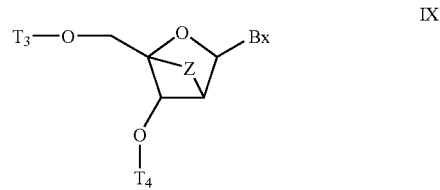

IX wherein independently for each of said at least one bicyclic nucleoside having Formula IX:

Bx is a heterocyclic base moiety;

$T_3$ and $T_4$ are each, independently, an internucleoside linking group linking the bicyclic nucleoside having Formula IX to the oligomeric compound or one of $T_3$ and $T_4$ is an internucleoside linking group linking the bicyclic nucleoside having Formula IX to the oligomeric compound and the other of $T_3$ and $T_4$ is H, a hydroxyl protecting group, a linked conjugate group or a 5' or 3'-terminal group;

Z is $C(q_1)=C(q_3)$, $C[=C(q_1)(q_2)]-C(q_3)(q_4)$ or $C(q_1)(q_2)-C[=C(q_3)(q_4)]$;

$q_1$, $q_2$, $q_3$ and $q_4$ are each, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_1$, $SJ_1$, $SO_2J_1$, $NJ_1J_2$, $N_3$, CN, C(=O)$OJ_1$, C(=O)$NJ_1J_2$, C(=O)$OJ_1$, O—C(=O)$NJ_1J_2$, N(H)C(=NH)$NJ_1J_2$, N(H)C(=O)$NJ_1J_2$ or N(H)C(=S)$NJ_1J_2$;

wherein each substituted group is, independently, mono or poly substituted with substituent groups independently selected from halogen, $C_1$-$C_6$ alkyl, $C_2$-$C_6$ alkenyl, $C_2$-$C_6$ alkynyl, $OJ_1$, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O)—$NJ_1J_2$ or N(H)C(=S)$NJ_1J_2$; and each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group.

In certain embodiments, oligomeric compounds are provided comprising at least one bicyclic nucleoside having Formula IX wherein Z is C($q_1$)=C($q_3$). In certain embodiments, oligomeric compounds are provided comprising at least one bicyclic nucleoside having Formula IX wherein Z is C[=($q_1$)($q_2$)]-C($q_3$)($q_4$). In certain embodiments, oligomeric compounds are provided comprising at least one bicyclic nucleoside having Formula IX wherein Z is C($q_1$)($q_2$)-C[=($q_3$)($q_4$)].

In certain embodiments, oligomeric compounds are provided comprising at least one bicyclic nucleoside having Formula IX wherein each $q_1$, $q_2$, $q_3$ and $q_4$ is H.

In certain embodiments, oligomeric compounds are provided comprising at least one bicyclic nucleoside having Formula IX wherein Z is C[=C($q_1$)($q_2$)]-C($q_3$)($q_4$) or C($q_1$)($q_2$)-C[=C($q_3$)($q_4$)] and three of $q_1$, $q_2$, $q_3$ and $q_4$ are H and the other one of $q_1$, $q_2$, $q_3$ and $q_4$ is other than H. In certain embodiments, the other one of $q_1$, $q_2$, $q_3$ and $q_4$ is halogen, $C_1$-$C_6$ alkyl, substituted $C_1$-$C_6$ alkyl, $C_1$-$C_6$ alkoxy, substituted $C_1$-$C_6$ alkoxy, $OJ_1$, $SJ_1$, $NJ_1J_2$ or CN. In certain embodiments, the other one of $q_1$, $q_2$, $q_3$ and $q_4$ is halogen, $C_1$-$C_{12}$ alkyl or $C_1$-$C_6$ alkoxy. In certain embodiments, the other one of $q_1$, $q_2$, $q_3$ and $q_4$ is fluoro or methyl.

In certain embodiments, oligomeric compounds are provided comprising at least one bicyclic nucleoside having Formula IX wherein Z is C[=C($q_1$)($q_2$)]-C($q_3$)($q_4$) or C($q_1$)($q_2$)-C[=C($q_3$)($q_4$)], two of $q_1$, $q_2$, $q_3$ and $q_4$ are H and the other two of $q_1$, $q_2$, $q_3$ and $q_4$ are other than H. In certain embodiments, the other two of $q_1$, $q_2$, $q_3$ and $q_4$ are each, independently, halogen, $C_1$-$C_6$ alkyl, substituted $C_1$-$C_6$ alkyl, $C_1$-$C_{12}$ alkoxy, substituted $C_1$-$C_{12}$ alkoxy, $OJ_1$, $SJ_1$, $NJ_1J_2$, or CN. In certain embodiments, the other two of $q_1$, $q_2$, $q_3$ and $q_4$ are each, independently, halogen, $C_1$-$C_{12}$ alkyl or $C_1$-$C_6$ alkoxy. In certain embodiments, the other two of $q_1$, $q_2$, $q_3$ and $q_4$ are each, independently, fluoro or methyl.

In certain embodiments, oligomeric compounds are provided comprising at least one bicyclic nucleoside having Formula IX wherein Z is C[=C($q_1$)($q_2$)]-C($q_3$)($q_4$) or C($q_1$)($q_2$)-C[=C($q_3$)($q_4$)], $q_1$ and $q_2$ are each H and $q_3$ and $q_4$ are other than H. In certain embodiments, oligomeric compounds are provided wherein Z is C[=C($q_1$)($q_2$)]-C($q_3$)($q_4$) or C($q_1$)($q_2$)-C[=C($q_3$)($q_4$)], $q_3$ and $q_4$ are each H and $q_1$ and $q_2$ are other than H. In certain embodiments, oligomeric compounds are provided wherein Z is C[=C($q_1$)($q_2$)]-C($q_3$)($q_4$) or C($q_1$)($q_2$)-C[=C($q_3$)($q_4$)], one of $q_1$ and $q_2$ is H, one of $q_3$ and $q_4$ is H and the other two of $q_1$, $q_2$, $q_3$ and $q_4$ are other than H.

In certain embodiments, oligomeric compounds are provided comprising at least one bicyclic nucleoside having Formula XI wherein one of $q_1$, $q_2$, $q_3$ and $q_4$ is H and the other three of $q_1$, $q_2$, $q_3$ and $q_4$ are other than H. In certain embodiments, the other three of $q_1$, $q_2$, $q_3$ and $q_4$ are each, independently, halogen, $C_1$-$C_6$ alkyl, substituted $C_1$-$C_6$ alkyl, $C_1$-$C_6$ alkoxy, substituted $C_1$-$C_6$ alkoxy, $OJ_1$, $SJ_1$, $NJ_1J_2$ or CN. In certain embodiments, the other three of $q_1$, $q_2$, $q_3$ and $q_4$ are each, independently, halogen, hydroxyl, $C_1$-$C_6$ alkyl or $C_1$-$C_6$ alkoxy. In certain embodiments, the other three of $q_1$, $q_2$, $q_3$ and $q_4$ are each, independently, fluoro or methyl.

In certain embodiments, oligomeric compounds are provided comprising at least one bicyclic nucleoside having Formula XI wherein Z is C($q_1$)=C($q_3$) and one of $q_1$ and $q_3$ is H and the other of $q_1$ and $q_3$ is other than H. In certain embodiments, the other of $q_1$ and $q_3$ is halogen, $C_1$-$C_6$ alkyl, substituted $C_1$-$C_6$ alkyl, $C_1$-$C_6$ alkoxy, substituted $C_1$-$C_6$ alkoxy, $OJ_1$, $SJ_1$, $NJ_1J_2$ or CN. In certain embodiments, the other of $q_1$ and $q_3$ is halogen, $C_1$-$C_6$ alkyl or $C_1$-$C_6$ alkoxy. In certain embodiments, the other of $q_1$ and $q_3$ is fluoro or methyl.

In certain embodiments, oligomeric compounds are provided comprising at least one bicyclic nucleoside having Formula XI wherein Z is C($q_1$)=C($q_3$) and $q_1$ and $q_3$ are both other than H. In certain embodiments, $q_1$ and $q_3$ are each, independently, halogen, $C_1$-$C_6$ alkyl, substituted $C_1$-$C_6$ alkyl, $C_1$-$C_{12}$ alkoxy, substituted $C_1$-$C_{12}$ alkoxy, $OJ_1$, $SJ_1$, $NJ_1J_2$, or CN. In certain embodiments, $q_1$ and $q_3$ are each, independently, halogen, $C_1$-$C_6$ alkyl or $C_1$-$C_{12}$ alkoxy.

In certain embodiments, oligomeric compounds are provided comprising at least one bicyclic nucleoside having Formula XI wherein one $T_3$ is H or a hydroxyl protecting group. In certain embodiments, at least one $T_3$ is an internucleoside linking group. In certain embodiments, one $T_4$ is H or a hydroxyl protecting group.

In certain embodiments, oligomeric compounds are provided comprising at least one bicyclic nucleoside having Formula XI wherein at least one $T_4$ is an internucleoside linking group. In certain embodiments, at least one of $T_3$ and $T_4$ is a 3' or 5'-terminal group.

In certain embodiments, oligomeric compounds are provided comprising at least one bicyclic nucleoside having Formula XI wherein each internucleoside linking group is, independently, a phosphodiester or phosphorothioate. In certain embodiments, oligomeric compounds are provided comprising at least one bicyclic nucleoside having Formula XI wherein each internucleoside linking group is a phosphorothioate.

In certain embodiments, oligomeric compounds are provided comprising at least one bicyclic nucleoside having Formula IX wherein each bicyclic nucleoside having Formula IX further has the configuration of Formula X:

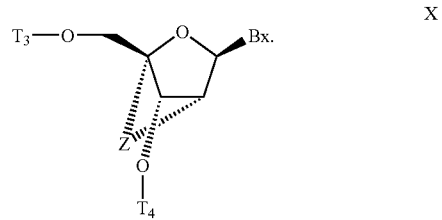

In certain embodiments, oligomeric compounds are provided comprising at least one region of at least two contiguous bicyclic nucleosides having Formula IX. In certain embodiments, the region of at least two contiguous bicyclic nucleosides having Formula IX is located at the 3' or the 5'-end of the oligomeric compound.

In certain embodiments, oligomeric compounds are provided comprising a gapped motif having an internal region of from about 6 to about 14 monomeric subunits separating two external regions independently comprising from 1 to about nucleoside, Compound 5 contiguous bicyclic nucleosides having Formula IX. In certain embodiments, essentially each monomeric subunit in the internal region is a β-D-2'-deoxyribonucleoside. In certain embodiments, the internal region comprises from about 8 to about 14 β-D-2'-deoxyribonucleosides. In certain embodiments, the internal region comprises from about 10 to about 14 β-D-2'-deoxyribonucleo-sides. In certain embodiments, the internal region comprises from about 10 to about 12 β-D-2'-deoxyribonucleosides. In certain embodiments, each external region independently comprises from 2 to about 3 bicyclic nucleosides having Formula IX. In certain embodiments, each external region independently comprises 2 bicyclic nucleosides having Formula XI. In certain embodiments, each external region independently comprises 2 bicyclic nucleosides having Formula IX and the internal region comprises 10 β-D-2'-deoxyribonucleosides. In certain embodiments, each external region independently comprises from 2 to about 3 bicyclic nucleosides having Formula IX and the internal region comprises 14 β-D-2'-deoxyribonucleo-sides. In certain embodiments, each external region independently comprises 2 bicyclic nucleosides having Formula IX and the internal region comprises 14 β-D-2'-deoxyribonucleo-sides.

In certain embodiments, oligomeric compounds are provided comprising a gapped motif having an internal region of from about 6 to about 14 monomeric subunits separating two external regions independently comprising from 1 to about 5 contiguous bicyclic nucleosides wherein each bicyclic nucleoside has Formula X:

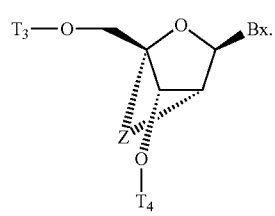

X

In certain embodiments, oligomeric compounds are provided comprising at least one bicyclic nucleoside of Formula IX from about 8 to about 40 monomer subunits in length. In certain embodiments, oligomeric compounds are provided comprising at least one bicyclic nucleoside of Formula IX from about 8 to about 20 monomer subunits in length. In certain embodiments, oligomeric compounds are provided comprising at least one bicyclic nucleoside of Formula IX from about 10 to about 16 monomer subunits in length. In certain embodiments, oligomeric compounds are provided comprising at least one bicyclic nucleoside of Formula IX from about 10 to about 14 monomer subunits in length.

In certain embodiments, methods of reducing target messenger RNA are provided comprising contacting one or more cells, a tissue or an animal with an oligomeric compound comprising at least one bicyclic nucleoside having Formula IX.

In certain embodiments, methods are provided comprising contacting a cell with an oligomeric compound, said oligomeric compound comprising at least one bicyclic nucleoside of Formula XI:

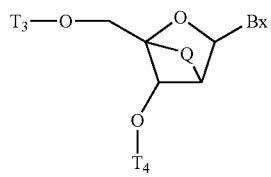

XI wherein independently for each of said at least one bicyclic nucleoside having Formula XI:

Bx is a heterocyclic base moiety;

$T_3$ and $T_4$ are each, independently, an internucleoside linking group linking the bicyclic nucleoside having Formula XI to the oligomeric compound or one of $T_3$ and $T_4$ is an internucleoside linking group linking the bicyclic nucleoside having Formula XI to the oligomeric compound and the other of $T_3$ and $T_4$ is H, a hydroxyl protecting group, a linked conjugate group or a 5' or 3'-terminal group;

Q is $C(q_1)(q_2)C(q_3)(q_4)$, $C(q_1)=C(q_3)$, $C[=C(q_1)(q_2)]$-$C(q_3)(q_4)$ or $C(q_1)(q_2)$-$C[=C(q_3)(q_4)]$;

$q_1$, $q_2$, $q_3$ and $q_4$ are each, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_1$, $SJ_1$, $SOJ_1$, $SO_2J_1$, $NJ_1J_2$, $N_3$, CN, $C(=O)OJ_1$, $C(=O)NJ_1J_2$, $C(=O)J_1$, $O-C(=O)NJ_1J_2$, $N(H)C(=NH)NJ_1J_2$, $N(H)C(=O)NJ_1J_2$ or $N(H)C(=S)NJ_1J_2$;

wherein each substituted group is, independently, mono or poly substituted with substituent groups independently selected from halogen, $C_1$-$C_6$ alkyl, $C_2$-$C_6$ alkenyl, $C_2$-$C_6$ alkynyl, $OJ_1$, $SJ_1$, $NJ_1J_2$, $N_3$, CN, $C(=O)OJ_1$, $C(=O)NJ_1J_2$, $C(=O)J_1$, $O-C(=O)NJ_1J_2$, $N(H)C(=O)-NJ_1J_2$ or $N(H)C(=S)NJ_1J_2$; and each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group.

In certain embodiments, methods are provided comprising contacting a cell with an oligomeric compound having at least one bicyclic nucleoside of Formula XI wherein the cell is in an animal. In certain embodiments, the cell is in a human.

In certain embodiments, methods are provided comprising contacting a cell with an oligomeric compound having at least one bicyclic nucleoside of Formula XI wherein the target RNA is selected from mRNA, pre-mRNA and micro RNA. In certain embodiments, the target RNA is mRNA. In certain embodiments, the target RNA is human mRNA.

In certain embodiments, methods are provided comprising contacting a cell with an oligomeric compound having at least one bicyclic nucleoside of Formula XI wherein the target RNA is cleaved thereby inhibiting its function.

In certain embodiments, methods are provided comprising contacting a cell with an oligomeric compound having at least one bicyclic nucleoside of Formula XI comprising evaluating the antisense activity of the oligomeric compound on said cell. In certain embodiments, the evaluating comprises detecting the levels of target RNA. In certain embodiments, the evaluating comprises detecting the levels of a protein. In certain embodiments, the evaluating comprises detection of one or more phenotypic effects.

In certain embodiments, bicyclic nucleoside are provided having Formula XII:

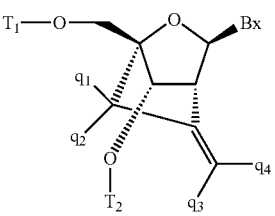

XII wherein:

Bx is a heterocyclic base moiety;

one of $T_1$ and $T_2$ is H or a hydroxyl protecting group and the other of $T_1$ and $T_2$ is H, a hydroxyl protecting group or a reactive phosphorus group;

$q_1$, $q_2$, $q_3$ and $q_4$ are each, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_1$, $SJ_1$, $SOJ_1$, $SO_2J_1$, $NJ_1J_2$, $N_3$, CN, C(=O)$OJ_1$, C(=O)$NJ_1J_2$, C(=O)$J_1$, O—C(=O)$NJ_1J_2$, N(H)C(=NH)$NJ_1J_2$, N(H)C(=O)$NJ_1J_2$ or N(H)C(=S)$NJ_1J_2$;

wherein each substituted group is, independently, mono or poly substituted with substituent groups independently selected from halogen, $C_1$-$C_6$ alkyl, $C_2$-$C_6$ alkenyl, $C_2$-$C_6$ alkynyl, $OJ_1$, $SJ_1$, $NJ_1J_2$, $N_3$, CN, C(=O)$J_1$, C(=O)$NJ_1J_2$, C(=O)$J_1$, O—C(=O)$NJ_1J_2$, N(H)C(=O)—$NJ_1J_2$ or N(H)C(=S)$NJ_1J_2$; and each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group.

In certain embodiments, bicyclic nucleosides are provided having Formula XII wherein $q_1$, $q_2$, $q_3$ and $q_4$ are each H.

In certain embodiments, oligomeric compounds are provided comprising at least one bicyclic nucleoside wherein each of said at least one bicyclic nucleoside has Formula XIII:

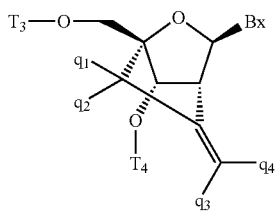

XIII wherein independently for each of said at least one bicyclic nucleoside having Formula XIII:

Bx is a heterocyclic base moiety;

$T_3$ and $T_4$ are each, independently, an internucleoside linking group linking the bicyclic nucleoside having Formula IX to the oligomeric compound or one of $T_3$ and $T_4$ is an internucleoside linking group linking the bicyclic nucleoside having Formula IX to the oligomeric compound and the other of $T_3$ and $T_4$ is H, a hydroxyl protecting group, a linked conjugate group or a 5' or 3'-terminal group;

$q_1$, $q_2$, $q_3$ and $q_4$ are each, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_1$, $SJ_1$, $SOJ_1$, $SO_2J_1$, $NJ_1J_2$, $N_3$, CN, C(=O)$OJ_1$, C(=O)$NJ_1J_2$, C(=O)$J_1$, O—C(=O)$NJ_1J_2$, N(H)C(=NH)$NJ_1J_2$, N(H)C(=O)$NJ_1J_2$ or N(H)C(=S)$NJ_1J_2$ wherein each substituted group is, independently, mono or poly substituted with substituent groups independently selected from halogen, $C_1$-$C_6$ alkyl, $C_2$-$C_6$ alkenyl, $C_2$-$C_6$ alkynyl, $OJ_1$, $SJ_1$, $NJ_1J_2$, $N_3$, CN, C(=O)$OJ_1$, C(=O)$NJ_1J_2$, C(=O)$OJ_1$, O—C(=O)$NJ_1J_2$, N(H)C(=O)—$NJ_1J_2$ or N(H)C(=S)$NJ_1J_2$; and each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group.

In certain embodiments, oligomeric compounds are provided having at least one bicyclic nucleoside of Formula XIII wherein each $q_1$, $q_2$, $q_3$ and $q_4$ of each of said at least one bicyclic nucleoside of Formula XIII is H.

In certain embodiments, carbocyclic bicyclic nucleosides are provided having the formula:

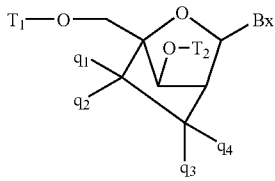

wherein:

Bx is a heterocyclic base moiety;

one of $T_1$ and $T_2$ is H or a hydroxyl protecting group and the other of $T_1$ and $T_2$ is H, a hydroxyl protecting group or a reactive phosphorus group;

each $q_1$, $q_2$, $q_3$ and $q_4$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_1$, $SJ_1$, $SOJ_1$, $SO_2J_1$, $NJ_1J_2$, $N_3$, CN, C(=O)$OJ_1$, C(=O)$NJ_1J_2$, C(=O)$J_1$, O—C(=O)$NJ_1J_2$, N(H)C(=NH)$NJ_1J_2$, N(H)C(=O)$NJ_1J_2$ or N(H)C(=S)$NJ_1J_2$;

wherein each substituted group is, independently, mono or poly substituted with substituent groups independently selected from halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $OJ_1$, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O)$NJ_1J_2$ or N(H)C(=S)$NJ_1J_2$;

each $J_1$ and $J_2$ is, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ aminoalkyl, substituted $C_1$-$C_6$ aminoalkyl or a protecting group; and wherein when one of $q_3$ or $q_4$ is $CH_3$ then at least one of the other of $q_3$ or $q_4$ or one of $q_1$ and $q_2$ is other than H.

In one embodiment, each of $q_1$, $q_2$, $q_3$ and $q_4$ is, independently, H. In certain embodiments, three of $q_1$, $q_2$, $q_3$ and $q_4$ are, independently, H and the other one of $q_1$, $q_2$, $q_3$ and $q_4$ is other than H. In a further embodiment, three of $q_1$, $q_2$, $q_3$ and $q_4$ are, independently, H and the other one of $q_1$, $q_2$, $q_3$ and $q_4$ is halogen, $C_1$-$C_6$ alkyl or substituted $C_1$-$C_6$ alkyl, $C_1$-$C_{12}$ alkoxy, substituted $C_1$-$C_{12}$ alkoxy, $OJ_1$, $SJ_1$, $NJ_1J_2$, or CN. In certain embodiments, the other one of $q_1$, $q_2$, $q_3$ and $q_4$ is substituted $C_1$-$C_6$ alkyl, $C_1$-$C_{12}$ alkoxy, substituted $C_1$-$C_{12}$ alkoxy, $OJ_1$, $SJ_1$, $NJ_1J_2$, or CN. In a further embodiment, the other one of $q_1$, $q_2$, $q_3$ and $q_4$ is F.

In one embodiment, two of $q_1$, $q_2$, $q_3$ and $q_4$ are, independently, H and the other two of $q_1$, $q_2$, $q_3$ and $q_4$ are, independently, halogen, $C_1$-$C_6$ alkyl or substituted $C_1$-$C_6$ alkyl, $C_1$-$C_{12}$ alkoxy, substituted $C_1$-$C_{12}$ alkoxy, $OJ_1$, $SJ_1$, $NJ_1J_2$, or CN. In a further embodiment, the other two of $q_1$, $q_2$, $q_3$ and $q_4$ are, independently, $C_1$-$C_6$ alkyl or substituted $C_1$-$C_6$ alkyl, $C_1$-$C_{12}$ alkoxy, substituted $C_1$-$C_{12}$ alkoxy, $OJ_1$, $SJ_1$, $NJ_1J_2$, or CN. In certain embodiments, the other two of $q_1$, $q_2$, $q_3$ and $q_4$ are, independently, $OJ_1$, $C_1$-$C_6$ alkyl or substituted $C_1$-$C_6$ alkyl, $C_1$-$C_{12}$ alkoxy or substituted $C_1$-$C_{12}$ alkoxy. In a further embodiment, the other two of $q_1$, $q_2$, $q_3$ and $q_4$ are, independently, F.

In one embodiment, one of $q_1$ and $q_2$ is H and one of $q_3$ and $q_4$ is H or both of $q_1$ and $q_2$ are H or both of $q_3$ and $q_4$ are H and the other two of $q_1$, $q_2$, $q_3$ and $q_4$ are other than H. In certain embodiments, the other two of $q_1$, $q_2$, $q_3$ and $q_4$ are other than H and are different one from the other. In a further embodiment, one of $q_1$ and $q_2$ and one of $q_3$ and $q_4$ is H and the other two of $q_1$, $q_2$, $q_3$ and $q_4$ are, independently, $C_1$-$C_6$ alkyl.

In one embodiment, $T_1$ and $T_2$ are each, independently, a hydroxyl protecting group wherein preferred hydroxyl protecting groups include, acetyl, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, benzoyl, p-phenylbenzoyl, 2,6-dichlorobenzyl, diphenylmethyl, p-nitrobenzyl, diphenylmethyl (trityl), 4,4'-dimethoxytrityl, trimethylsilyl, triethylsilyl, t-butyldimethylsilyl, t-butyldiphenylsilyl, triphenylsilyl, triisopropyl-silyl, benzoylformate, chloroacetyl, trichloroacetyl, trifluoroacetyl, pivaloyl, 9-fluorenylmethyl carbonate, mesylate, tosylate, triflate, trityl, monomethoxytrityl, dimethoxytrityl, trimethoxytrityl, 9-phenylxanthine-9-yl (Pixyl) and 9-(p-methoxyphenyl)xanthine-9-yl (MOX).

In one embodiment, $T_1$ is acetyl, benzyl, t-butyldimethylsilyl, t-butyldiphenylsilyl or dimethoxytrityl. In certain embodiments, $T_1$ is 4,4'-dimethoxytrityl.

In one embodiment, $T_2$ is a reactive phosphorus group wherein preferred reactive phosphorus groups include diisopropylcyanoethoxy phosphoramidite and H-phosphonate.

In certain embodiments, $T_1$ is 4,4'-dimethoxytrityl and $T_2$ is diisopropylcyanoethoxy phosphoramidite.

In one embodiment, Bx is pyrimidine, substituted pyrimidine, purine, or substituted purine. In certain embodiments, Bx is uracil, 5-methyluracil, 5-methylcytosine, 5-thiazolouracil, 5-thiazolo-cytosine, adenine, guanine, or 2,6-diaminopurine.

In one embodiment, each $J_1$ and $J_2$ is, independently, H or $C_1$-$C_3$ alkyl.

Also provided herein are carbocyclic bicyclic nucleosides having the formula shown above and further having the configuration shown in the formula below:

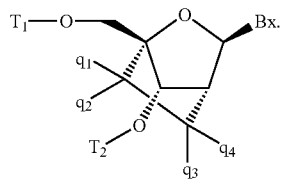

The Also provided herein are oligomeric compounds comprising at least one bicyclic nucleoside having the formula:

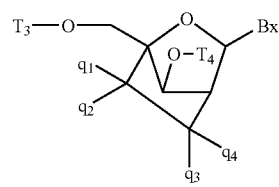

wherein:

Bx is a heterocyclic base moiety;

$T_3$ is hydroxyl, a protected hydroxyl, a linked conjugate group or an internucleoside linking group attached to a nucleoside, a nucleotide, an oligonucleoside, an oligonucleotide, a monomeric subunit or an oligomeric compound;

$T_4$ is hydroxyl, a protected hydroxyl, a linked conjugate group or an internucleoside linking group attached to a nucleoside, a nucleotide, an oligonucleoside, an oligonucleotide, a monomeric subunit or an oligomeric compound;

wherein at least one of $T_3$ and $T_4$ is an internucleoside linking group attached to a nucleoside, a nucleotide, an oligonucleoside, an oligonucleotide, a monomeric subunit or an oligomeric compound;

each $q_1$, $q_2$, $q_3$ and $q_4$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_1$, $SJ_1$, $SOJ_1$, $SO_2J_1$, $NJ_1J_2$, $N_3$, CN, C(=O)$OJ_1$, C(=O)$NJ_1J_2$, C(=O)$J_1$, O—C(=O)$NJ_1J_2$, N(H)C(=NH)$NJ_1J_2$, N(H)C(=O)$NJ_1J_2$ or N(H)C(=S)$NJ_1J_2$;

wherein each substituted group is, independently, mono or poly substituted with substituent groups independently selected from halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $OJ_1$, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O)$NJ_1J_2$ or N(H)C(=S)$NJ_1J_2$;

each $J_1$ and $J_2$ is, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ aminoalkyl, substituted $C_1$-$C_6$ aminoalkyl or a protecting group; and wherein when one of $q_3$ or $q_4$ is $CH_3$ then at least one of the other of $q_3$ or $q_4$ or one of $q_1$ and $q_2$ is other than H.

In one embodiment, each of $q_1$, $q_2$, $q_3$ and $q_4$ is, independently, H. In certain embodiments, three of $q_1$, $q_2$, $q_3$ and $q_4$ are, independently, H and the other one of $q_1$, $q_2$, $q_3$ and $q_4$ is other than H. In a further embodiment, the other one of $q_1$, $q_2$, $q_3$ and $q_4$ is halogen, $C_1$-$C_6$ alkyl or substituted $C_1$-$C_6$ alkyl, $C_1$-$C_{12}$ alkoxy, substituted $C_1$-$C_{12}$ alkoxy, $OJ_1$, $SJ_1$, $NJ_1J_2$, or CN.

In certain embodiments, the other one of $q_1$, $q_2$, $q_3$ and $q_4$ is substituted $C_1$-$C_6$ alkyl, $C_1$-$C_{12}$ alkoxy, substituted $C_1$-$C_{12}$ alkoxy, $OJ_1$, $SJ_1$, $NJ_1J_2$, or CN. In a further embodiment, the other one of $q_1$, $q_2$, $q_3$ and $q_4$ is F.

In one embodiment, two of $q_1$, $q_2$, $q_3$ and $q_4$ are, independently, H and the other two of $q_1$, $q_2$, $q_3$ and $q_4$ are, independently, halogen, $C_1$-$C_6$ alkyl or substituted $C_1$-$C_6$ alkyl, $C_1$-$C_{12}$ alkoxy, substituted $C_1$-$C_{12}$ alkoxy, $OJ_1$, $SJ_1$, $NJ_1J_2$, or CN. In a further embodiment, the other two of $q_1$, $q_2$, $q_3$ and $q_4$ are, independently, halogen, $C_1$-$C_6$ alkyl or substituted $C_1$-$C_6$ alkyl, $C_1$-$C_{12}$ alkoxy, substituted $C_1$-$C_{12}$ alkoxy, $OJ_1$, $SJ_1$, $NJ_1J_2$, or CN. In certain embodiments, the other two of $q_1$, $q_2$, $q_3$ and $q_4$ are, independently, $OJ_1$, $C_1$-$C_6$ alkyl or substituted $C_1$-$C_6$ alkyl, $C_1$-$C_{12}$ alkoxy or substituted $C_1$-$C_{12}$ alkoxy. In certain embodiments, the other two of q1, $q_2$, $q_3$ and $q_4$ are, independently, F.

In one embodiment, one of $q_1$ and $q_2$ is H and one of $q_3$ and $q_4$ is H or both of $q_1$ and $q_2$ are H or both of $q_3$ and $q_4$ are H and the other two of $q_1$, $q_2$, $q_3$ and $q_4$ are other than H. In certain embodiments, the other two of $q_1$, $q_2$, $q_3$ and $q_4$ are other than H and are different one from the other. In a further embodiment, one of $q_1$ and $q_2$ and one of $q_3$ and $q_4$ is H and the other two of $q_1$, $q_2$, $q_3$ and $q_4$ are, independently, $C_1$-$C_6$ alkyl.

In one embodiment, $T_3$ is hydroxyl or a protected hydroxyl. In certain embodiments, $T_3$ is an internucleoside linking group attached to a nucleoside, a nucleotide or a monomeric subunit. In a further embodiment, $T_3$ is an internucleoside linking group attached to an oligonucleoside or an oligonucleotide. In certain embodiments, $T_3$ is an internucleoside linking group attached to an oligomeric compound.

In one embodiment, $T_4$ is hydroxyl or a protected hydroxyl. In certain embodiments, $T_4$ is an internucleoside linking group attached to a nucleoside, a nucleotide or a monomeric subunit. In a further embodiment, $T_4$ is an internucleoside linking group attached to an oligonucleoside or an oligonucleotide. In certain embodiments, $T_4$ is an internucleoside linking group attached to an oligomeric compound.

In certain embodiments, at least one of $T_3$ and $T_4$ comprises an internucleoside linking group selected from phosphodiester or phosphorothioate.

Also provided herein are oligomeric compounds having at least one carbocyclic bicyclic nucleoside having the formula shown above and further having the configuration shown in the formula below:

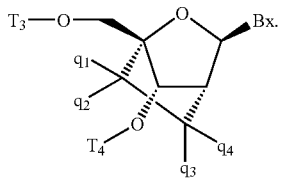

In one embodiment, each internucleoside linking group is, independently, a phosphodiester or a phosphorothioate.

In one embodiment, oligomeric compounds are provided comprising at least one region of at least two contiguous bicyclic nucleosides having the formula. In certain embodiments, the region of at least two contiguous bicyclic nucleosides having the formula is located at the 3' or the 5'-end of the oligomeric compound. In a further embodiment, the region of at least two contiguous bicyclic nucleosides having the formula is located at the 3' or the 5'-end of the oligomeric compound and the oligomeric compound further comprises at least one bicyclic nucleoside having the formula located at the other of the 3' or the 5'-end of the oligomeric compound.

In one embodiment, oligomeric compounds are provided having a gapped motif.

In one embodiment, oligomeric compound are provided comprising from about 8 to about 40 nucleosides and/or modified nucleosides or mimetics in length. In certain embodiments, oligomeric compound are provided comprising from about 8 to about 20 nuclesides and/or modified nucleosides or mimetics in length. In a further embodiment, oligomeric compound are provided comprising from about 10 to about 16 nuclesides and/or modified nucleosides or mimetics in length. In certain embodiments, oligomeric compound are provided comprising from about 10 to about 14 nuclesides and/or modified nucleosides or mimetics in length.

Also provided are methods of reducing target messenger RNA comprising contacting one or more cells, a tissue or an animal with an oligomeric compound of the invention.

In certain embodiments, bicyclic nucleoside analogs are provided having the formula:

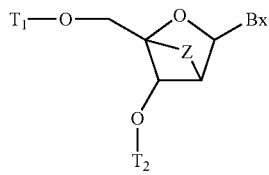

wherein:
Bx is a heterocyclic base moiety;
one of $T_1$ and $T_2$ is H or a hydroxyl protecting group and the other of $T_1$ and $T_2$ is H, a hydroxyl protecting group or a reactive phosphorus group;

Z is $C(q_1)=C(q_2)$, $C[=C(q_1)(q_2)]-C(q_3)(q_4)$ or $C(q_3)(q_4)-C[=C(q_1)(q_2)]$;

$q_1$, $q_2$, $q_3$ and $q_4$ are each, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_1$, $SJ_1$, $SOJ_1$, $SO_2J_1$, $NJ_1J_2$, $N_3$, CN, $C(=O)OJ_1$, $C(=O)NJ_1J_2$, $O-C(=O)NJ_1J_2$, $N(H)C(=NH)NJ_1J_2$, $N(H)C(=O)NJ_1J_2$ or $N(H)C(=S)NJ_1J_2$;

wherein each substituted group is, independently, mono or poly substituted with substituent groups independently selected from halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $OJ_1$, $SJ_1$, $NJ_1J_2$, $N_3$, CN, $C(=O)OJ_1$, $C(=O)NJ_1J_2$, $C(=O)J_1$, $O-C(=O)NJ_1J_2$, $N(H)C(=O)NJ_1J_2$ or $N(H)C(=S)NJ_1J_2$; and each $J_1$ and $J_2$ is, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ aminoalkyl, substituted $C_1$-$C_6$ aminoalkyl or a protecting group.

In one embodiment, Z is $C(q_1)=C(q_2)$. In certain embodiments, Z is $C[=(q_1)(q_2)]-C(q_3)(q_4)$. In a further embodiment, Z is $C(q_3)(q_4)-C[=(q_1)(q_2)]$.

In one embodiment, Z is $C[=C(q_1)(q_2)]-C(q_3)(q_4)$ or $C(q_3)(q_4)-C[=C(q_1)(q_2)]$ and $q_1$, $q_2$, $q_3$ and $q_4$ are each, independently H.

In one embodiment, Z is $C[=C(q_1)(q_2)]-C(q_3)(q_4)$ or $C(q_3)(q_4)-C[=C(q_1)(q_2)]$, three of $q_1$, $q_2$, $q_3$ and $q_4$ are, independently, H and one of $q_1$, $q_2$, $q_3$ and $q_4$ is other than H. In certain embodiments, the one of $q_1$, $q_2$, $q_3$ and $q_4$ that is not H is halogen, $OJ_1$, $C_1$-$C_6$ alkyl, substituted $C_1$-$C_6$ alkyl, $C_1$-$C_{12}$ alkoxy, substituted $C_1$-$C_{12}$ alkoxy, $OJ_1$, $SJ_1$, $NJ_1J_2$, or CN. In a further embodiment, the one of $q_1$, $q_2$, $q_3$ and $q_4$ that is not H is halogen, $C_1$-$C_{12}$ alkyl or substituted $C_1$-$C_{12}$ alkyl.

In one embodiment, Z is $C[=C(q_1)(q_2)]-C(q_3)(q_4)$ or $C(q_3)(q_4)-C[=C(q_1)(q_2)]$, two of $q_1$, $q_2$, $q_3$ and $q_4$ are, independently, H and the other two of $q_1$, $q_2$, $q_3$ and $q_4$ are other than H. In a further embodiment, the two of $q_1$, $q_2$, $q_3$ and $q_4$ that are not H are each, independently, halogen, $OJ_1$, $C_1$-$C_6$ alkyl, substituted $C_1$-$C_6$ alkyl, $C_1$-$C_{12}$ alkoxy, substituted $C_1$-$C_{12}$ alkoxy, $OJ_1$, $SJ_1$, $NJ_1J_2$, or CN. In certain embodiments, the two of $q_1$, $q_2$, $q_3$ and $q_4$ that are not H are each, independently, halogen, $C_1$-$C_{12}$ alkyl or substituted $C_1$-$C_{12}$ alkyl. In a further embodiment, $q_1$ and $q_2$ are each, independently, H. In certain embodiments, $q_3$ and $q_4$ are each, independently, H. In certain embodiments, one of $q_1$ and $q_2$ is H and one of $q_3$ and $q_4$ is H.

In one embodiment, Z is $C[=C(q_1)(q_2)]-C(q_3)(q_4)$ or $C(q_3)(q_4)-C[=C(q_1)(q_2)]$ and only one of $q_1$, $q_2$, $q_3$ and $q_4$ is H. In certain embodiments, each of the three of $q_1$, $q_2$, $q_3$ and $q_4$ that are not H are each, independently, halogen, $OJ_1$, $C_1$-$C_6$ alkyl, substituted $C_1$-$C_6$ alkyl, $C_1$-$C_{12}$ alkoxy, substituted $C_1$-$C_{12}$ alkoxy, $OJ_1$, $SJ_1$, $NJ_1J_2$, or CN. In a further embodiment, each of the three of $q_1$, $q_2$, $q_3$ and $q_4$ that are not H are each, independently, halogen, hydroxyl, $C_1$-$C_{12}$ alkyl or substituted $C_1$-$C_{12}$ alkyl.

In one embodiment, Z is $C(q_1)=C(q_2)$ and $q_1$ and $q_2$ are each, independently, H. In certain embodiments, Z is $C(q_1)=C(q_2)$ and one of $q_1$ and $q_2$ is H and the other of $q_1$ and $q_2$ is other than H. In a further embodiment, one of $q_1$ and $q_2$ is H and the other is halogen, $OJ_1$, $C_1$-$C_6$ alkyl, substituted $C_1$-$C_6$ alkyl, $C_1$-$C_{12}$ alkoxy, substituted $C_1$-$C_{12}$ alkoxy, $OJ_1$, $SJ_1$, $NJ_1J_2$, or CN. In certain embodiments, one of $q_1$ and $q_2$ is H and the other is halogen, $C_1$-$C_{12}$ alkyl or substituted $C_1$-$C_{12}$ alkyl.

In one embodiment, Z is $C(q_1)=C(q_2)$ and $q_1$ and $q_2$ are both other than H. In certain embodiments, $q_1$ and $q_2$ are each, independently, halogen, $OJ_1$, $C_1$-$C_6$ alkyl, substituted $C_1$-$C_6$ alkyl, $C_1$-$C_6$ alkoxy, substituted $C_1$-$C_{12}$ alkoxy, $OJ_1$, $SJ_1$, $NJ_1J_2$, or CN. In a further embodiment, $q_1$ and $q_2$ are each, independently, halogen, $C_1$-$C_{12}$ alkyl or substituted $C_1$-$C_{12}$ alkyl.

In one embodiment, $T_1$ and $T_2$ are each, independently, a hydroxyl protecting group. In certain embodiments, each of the hydroxyl protecting groups is, independently, selected from acetyl, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, benzoyl, p-phenylbenzoyl, 2,6-dichlorobenzyl, diphenylmethyl, p-nitrobenzyl, triphenylmethyl (trityl), 4,4'-dimethoxytrityl, trimethylsilyl, triethylsilyl, t-butyldimethylsilyl, t-butyldiphenylsilyl, triphenylsilyl, triisopropylsilyl, benzoylformate, chloroacetyl, trichloroacetyl, trifluoroacetyl, pivaloyl, 9-fluorenylmethyl carbonate, mesylate, tosylate, triflate, trityl, monomethoxytrityl, dimethoxytrityl, trimethoxytrityl, 9-phenylxanthine-9-yl (Pixyl) and 9-(p-methoxy-phenyl)xanthine-9-yl (MOX).

In one embodiment, $T_1$ is acetyl, benzyl, t-butyldimethylsilyl, t-butyldiphenylsilyl or 4,4'-dimethoxytrityl. In certain embodiments, $T_1$ is 4,4'-dimethoxytrityl. In a further embodiment, $T_1$ is 4,4'-dimethoxytrityl and $T_2$ is diisopropylcyanoethoxy phosphoramidite.

In one embodiment, $T_2$ is a reactive phosphorus group. In certain embodiments, the reactive phosphorus group is diisopropylcyanoethoxy phosphoramidite or H-phosphonate.

In one embodiment, Bx is a pyrimidine, substituted pyrimidine, purine, or substituted purine. In certain embodiments, Bx is uracil, 5-methyluracil, 5-methylcytosine, 5-thiazolo-uracil, 5-thiazolo-cytosine, adenine, guanine, or 2,6-diaminopurine.

In one embodiment, each $J_1$ and $J_2$ is, independently, H or $C_1$-$C_3$ alkyl.

In one embodiment, bicyclic nucleoside are provided having the configuration:

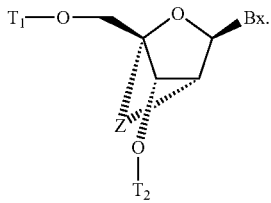

In certain embodiments, oligomeric compounds are provided comprising at least one bicyclic nucleoside having the formula:

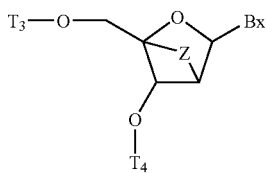

wherein:

Bx is a heterocyclic base moiety;

$T_3$ is hydroxyl, a protected hydroxyl, a linked conjugate group or an internucleoside linking group attached to a nucleoside, a nucleotide, an oligonucleoside, an oligonucleotide, a monomeric subunit or an oligomeric compound;

$T_4$ is hydroxyl, a protected hydroxyl, a linked conjugate group or an internucleoside linking group attached to a nucleoside, a nucleotide, an oligonucleoside, an oligonucleotide, a monomeric subunit or an oligomeric compound;

wherein at least one of $T_3$ and $T_4$ is an internucleoside linking group attached to a nucleoside, a nucleotide, an oligonucleoside, an oligonucleotide, a monomeric subunit or an oligomeric compound;

Z is $C(q_1)=C(q_2)$, $C[=C(q_1)(q_2)]-C(q_3)(q_4)$ or $C(q_3)(q_4)-C[=C(q_1)(q_2)]$;

$q_1$, $q_2$, $q_3$ and $q_4$ are each, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_1$, $SJ_1$, $SOJ_1$, $SO_2J_1$, $NJ_1J_2$, $N_3$, CN, $C(=O)OJ_1$, $C(=O)NJ_1J_2$, $C(=O)J_1$, $O-C(=O)NJ_1J_2$, $N(H)C(=NH)NJ_1J_2$, $N(H)C(=O)NJ_1J_2$ or $N(H)C(=S)NJ_1J_2$;

wherein each substituted group is, independently, mono or poly substituted with substituent groups independently selected from halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $OJ_1$, $SJ_1$, $NJ_1J_2$, $N_3$, CN, $C(=O)OJ_1$, $C(=O)NJ_1J_2$, $C(=O)J_1$, $O-C(=O)NJ_1J_2$, $N(H)C(=O)NJ_1J_2$ or $N(H)C(=S)NJ_1J_2$; and each $J_1$ and $J_2$ is, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ aminoalkyl, substituted $C_1$-$C_6$ aminoalkyl or a protecting group.

In one embodiment, Z is $C(q_1)=C(q_2)$. In certain embodiments, Z is $C[=(q_1)(q_2)]-C(q_3)(q_4)$. In a further embodiment, Z is $C(q_3)(q_4)-C[=(q_1)(q_2)]$.

In one embodiment, Z is $C[=C(q_1)(q_2)]-C(q_3)(q_4)$ or $C(q_3)(q_4)-C[=C(q_1)(q_2)]$ and $q_1$, $q_2$, $q_3$ and $q_4$ are each, independently H.

In one embodiment, Z is $C[=C(q_1)(q_2)]-C(q_3)(q_4)$ or $C(q_3)(q_4)-C[=C(q_1)(q_2)]$, three of $q_1$, $q_2$, $q_3$ and $q_4$ are, independently, H and one of $q_1$, $q_2$, $q_3$ and $q_4$ is other than H. In certain embodiments, the one of $q_1$, $q_2$, $q_3$ and $q_4$ that is not H is halogen, $OJ_1$, $C_1$-$C_6$ alkyl, substituted $C_1$-$C_6$ alkyl, $C_1$-$C_{12}$ alkoxy, substituted $C_1$-$C_{12}$ alkoxy, $OJ_1$, $SJ_1$, $NJ_1J_2$, or CN. In a further embodiment, the one of $q_1$, $q_2$, $q_3$ and $q_4$ that is not H is halogen, $C_1$-$C_{12}$ alkyl or substituted $C_1$-$C_{12}$ alkyl.

In one embodiment, Z is $C[=C(q_1)(q_2)]-C(q_3)(q_4)$ or $C(q_3)(q_4)-C[=C(q_1)(q_2)]$, two of $q_1$, $q_2$, $q_3$ and $q_4$ are, independently, H and the other two of $q_1$, $q_2$, $q_3$ and $q_4$ are other than H. In a further embodiment, the two of $q_1$, $q_2$, $q_3$ and $q_4$ that are not H are each, independently, halogen, $OJ_1$, $C_1$-$C_6$ alkyl, substituted $C_1$-$C_6$ alkyl, $C_1$-$C_{12}$ alkoxy, substituted $C_1$-$C_{12}$ alkoxy, $OJ_1$, $SJ_1$, $NJ_1J_2$, or CN. In certain embodiments, the two of $q_1$, $q_2$, $q_3$ and $q_4$ that are not H are each, independently, halogen, $C_1$-$C_{12}$ alkyl or substituted $C_1$-$C_{12}$ alkyl. In a further embodiment, $q_1$ and $q_2$ are each, independently, H. In certain embodiments, $q_3$ and $q_4$ are each, independently, H. In certain embodiments, one of $q_1$ and $q_2$ is H and one of $q_3$ and $q_4$ is H.

In one embodiment, Z is $C[=C(q_1)(q_2)]-C(q_3)(q_4)$ or $C(q_3)(q_4)-C[=C(q_1)(q_2)]$ and only one of $q_1$, $q_2$, $q_3$ and $q_4$ is H. In certain embodiments, each of the three of $q_1$, $q_2$, $q_3$ and $q_4$ that are not H are each, independently, halogen, $OJ_1$, $C_1$-$C_6$ alkyl, substituted $C_1$-$C_6$ alkyl, $C_1$-$C_{12}$ alkoxy, substituted $C_1$-$C_{12}$ alkoxy, $OJ_1$, $SJ_1$, $NJ_1J_2$, or CN. In a further embodiment, each of the three of $q_1$, $q_2$, $q_3$ and $q_4$ that are not H are each, independently, halogen, hydroxyl, $C_1$-$C_{12}$ alkyl or substituted $C_1$-$C_{12}$ alkyl.

In one embodiment, Z is $C(q_1)=C(q_2)$ and $q_1$ and $q_2$ are each, independently, H. In certain embodiments, Z is $C(q_1)=C(q_2)$ and one of $q_1$ and $q_2$ is H and the other of $q_1$ and $q_2$ is other than H. In a further embodiment, one of $q_1$ and $q_2$ is H and the other is halogen, $OJ_1$, $C_1$-$C_6$ alkyl, substituted $C_1$-$C_6$ alkyl, $C_1$-$C_{12}$ alkoxy, substituted $C_1$-$C_{12}$ alkoxy, $OJ_1$, $SJ_1$, $NJ_1J_2$, or CN.

In certain embodiments, one of $q_1$ and $q_2$ is H and the other is halogen, $C_1$-$C_{12}$ alkyl or substituted $C_1$-$C_{12}$ alkyl.

In one embodiment, Z is $C(q_1)=C(q_2)$ and $q_1$ and $q_2$ are both other than H. In certain embodiments, $q_1$ and $q_2$ are each, independently, halogen, $OJ_1$, $C_1$-$C_6$ alkyl, substituted $C_1$-$C_6$ alkyl, $C_1$-$C_{12}$ alkoxy, substituted $C_1$-$C_{12}$ alkoxy, $OJ_1$, $SJ_1$, $NJ_1J_2$, or CN. In a further embodiment, $q_1$ and $q_2$ are each, independently, halogen, $C_1$-$C_{12}$ alkyl or substituted $C_1$-$C_{12}$ alkyl.

In one embodiment, Bx is pyrimidine, substituted pyrimidine, purine, or substituted purine. In certain embodiments, Bx is uracil, 5-methyluracil, 5-methylcytosine, 5-thiazolo-uracil, 5-thiazolo-cytosine, adenine, guanine, or 2,6-diaminopurine.

In one embodiment, each $J_1$ and $J_2$ is, independently, H or $C_1$-$C_3$ alkyl.

In one embodiment, $T_3$ is hydroxyl or a protected hydroxyl. In certain embodiments, $T_3$ is an internucleoside linking group attached to a nucleoside, a nucleotide or a monomeric subunit. In a further embodiment, $T_3$ is an internucleoside linking group attached to an oligonucleoside or an oligonucleotide. In certain embodiments, $T_3$ is an internucleoside linking group attached to an oligomeric compound.

In one embodiment, $T_4$ is hydroxyl or a protected hydroxyl. In certain embodiments, $T_4$ is an internucleoside linking group attached to a nucleoside, a nucleotide or a monomeric subunit. In a further embodiment, $T_4$ is an internucleoside linking group attached to an oligonucleoside or an oligonucleotide. In certain embodiments, $T_4$ is an internucleoside linking group attached to an oligomeric compound.

In one embodiment, at least one of $T_3$ and $T_4$ comprises an internucleoside linking group selected from phosphodiester or phosphorothioate.

In one embodiment, oligomeric compounds are provided having at least one bicyclic nucleoside having the configuration:

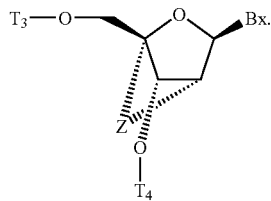

In one embodiment each internucleoside linking group is, independently, a phosphodiester or a phosphorothioate.

In one embodiment, oligomeric compounds are provided comprising at least one region of at least two contiguous bicyclic nucleosides having the formula. In certain embodiments, oligomeric compounds are provided comprising at least two contiguous bicyclic nucleosides having the formula located at the 3' or the 5'-end of the oligomeric compound. In a further embodiment, oligomeric compounds are provided comprising at least two contiguous bicyclic nucleosides having the formula located at the 3' or the 5'-end of the oligomeric compound and at least one bicyclic nucleoside having the formula located at the other of the 3' or the 5'-end of the oligomeric compound. In one embodiment, gapped oligomeric compounds are provided comprising at least two contiguous bicyclic nucleosides having the formula located at the 3' or the 5'-end of the oligomeric compound and at least one bicyclic nucleoside having the formula located at the other of the 3' or the 5'-end of the oligomeric compound.

In one embodiment, a gapped oligomeric compound is provided comprising one or two bicyclic nucleosides having said formula at the 5'-end and two or three bicyclic nucleosides having said formula at the 3'-end. In certain embodiments, the gapped oligomeric compound comprises an internal region of from about 10 to about 16 β-D-deoxyribonucleosides. In a further embodiment, the gapped oligomeric compound comprises an internal region of from about 10 to about 14 β-D-deoxyribonucleosides. In certain embodiments, the gapped oligomeric compound comprises from 10 to 16 nucleosides and/or modified nucleosides or mimetics in length.

In one embodiment, oligomeric compounds are provided comprising from about 8 to about 40 nucleosides and/or modified nucleosides or mimetics in length. In certain embodiments, oligomeric compounds are provided comprising from about 8 to about 20 nuclesides and/or modified nucleosides or mimetics in length. In a further embodiment, oligomeric compounds are provided comprising from about 10 to about 16 nuclesides and/or modified nucleosides or mimetics in length. In certain embodiments, oligomeric compounds are provided comprising from about 10 to about 14 nuclesides and/or modified nucleosides or mimetics in length.

Also provided are methods of inhibiting gene expression comprising contacting one or more cells, a tissue or an animal with an oligomeric compound of the invention.

DETAILED DESCRIPTION OF THE INVENTION

Provided herein are carbocyclic bicyclic nucleosides (also referred to herein as bicyclic nucleosides), oligomeric compounds comprising the carbocyclic bicyclic nucleosides and methods of using the oligomeric compounds. The carbocyclic bicyclic nucleosides impart enhanced properties to oligomeric compounds they are incorporated into. In certain embodiments, the oligomeric compounds and compositions are designed to hybridize to a portion of a target RNA. The oligomers provided herein may also be useful as primers and probes in diagnostic applications. In certain embodiments, the carbocyclic bicyclic nucleosides provided herein are represented by formulas Ia, Ib, Ic and Id:

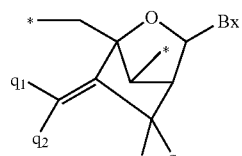

Ia

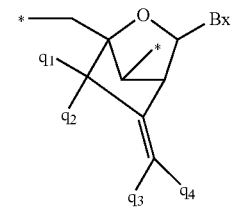

Ib

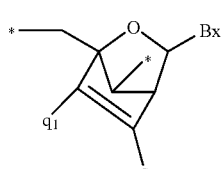

Ic

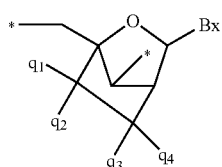

Id

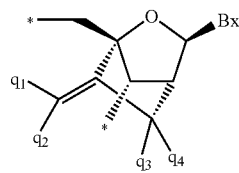

Ie

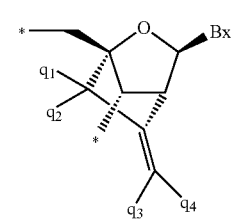

If

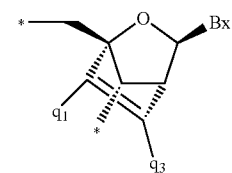

Ig

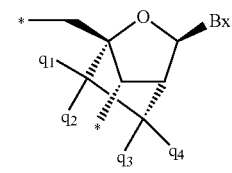

Ih as monomers the asterisks are representative of various groups that are present during monomer synthesis up to the amidite stage. Functional groups can also be attached at the monomer stage that will enhance or otherwise be useful after incorporation of the monomer into an oligomer. Representative groups useful at the monomer stage include but are not limited to hydroxyl, protected hydroxyl, an optionally linked conjugate group, a reporter group or a reactive phosphorus group. After incorporation into an oligomeric compound the asterisks will be representative of internucleoside linking groups such as a phosphodiester or phosphorothioate internucleoside linking groups connecting the monomers within the oligomeric compound except for terminally located monomers at the 5' and 3' ends. The terminal monomers can have terminal hydroxyl or protected hydroxyl groups or can have a variety of other groups attached that are routinely added to the termini of oligomeric compounds to enhance a desired property such as for example conjugate or reporter groups. Especially useful terminal groups include those that enhance the antisense activity of the oligomeric compounds.

Bx is a heterocyclic base moiety that can be modified but is preferably a purine or pyrimidine nucleobase.

Each $q_1$, $q_2$, $q_3$ and $q_4$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_1$, $SJ_1$, $SOJ_1$, $SO_2J_1$, $NJ_1J_2$, $N_3$, CN, $C(=O)OJ_1$, $C(=O)-NJ_1J_2$, $C(=O)J_1$, $O-C(=O)NJ_1J_2$, $N(H)C(=NH)NJ_1J_2$, $N(H)C(=O)NJ_1J_2$ or $N(H)C(=S)NJ_1J_2$; wherein each substituted group is, independently, mono or poly substituted with substituent groups independently selected from halogen, $OJ_1$, $SJ_1$, $NJ_1J_2$, $N_3$, CN, $C(=O)OJ_1$, $C(=O)NJ_1J_2$, $C(=O)J_1$, $O-C(=O)NJ_1J_2$, $N(H)C(=O)NJ_1J_2$ or $N(H)C(=S)NJ_1J_2$; and each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group.

In certain embodiments, each $q_1$, $q_2$, $q_3$ and $q_4$ is H. In certain embodiments, one of $q_1$, $q_2$, $q_3$ and $q_4$ is other than H. In certain embodiments, two of $q_1$, $q_2$, $q_3$ and $q_4$ are other than H.

In certain embodiments, three of $q_1$, $q_2$, $q_3$ and $q_4$ are other than H. In certain embodiments, each of $q_1$, $q_2$, $q_3$ and $q_4$ is other than H. In certain embodiments, $q_1$, $q_2$, $q_3$ and $q_4$ are independently, halogen, $C_1$-$C_6$ alkyl, substituted $C_1$-$C_6$ alkyl, $C_1$-$C_6$ alkoxy, substituted $C_1$-$C_6$ alkoxy, $OJ_1$, $SJ_1$, $NJ_1J_2$ or CN. In certain embodiments, $q_1$, $q_2$, $q_3$ and $q_4$ are independently, halogen, $C_1$-$C_6$ alkyl or $C_1$-$C_6$ alkoxy. In certain embodiments, $q_1$, $q_2$, $q_3$ and $q_4$ are independently, fluoro or methyl.

In certain embodiments, carbocyclic bicyclic nucleosides represented by formulas Ia, Ib, Ic and Id are provided having the configuration represented by formulas Ie, If, Ig and Ih:

wherein the variables are as defined above.

Oligomeric compounds comprising carbocyclic bicyclic nucleosides were tested for in vivo activity (Example 56). Oligomeric compounds were prepared having a 2/14/2 gapped motif wherein for each oligomeric compound the 14 nucleosides in the gap were β-D-2'-deoxyribonucleosides and the 4 nucleosides in the wings for each oligomeric compound were selected from one of the formulas shown below:

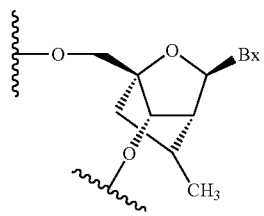

VIa

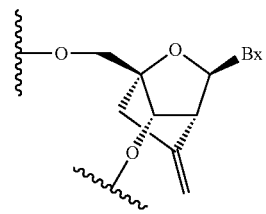

Xa

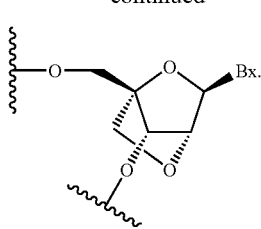
XIIa

Each of the oligomeric compounds showed good activity at the high dose with the oligomeric compounds having formulas Xa and XIIa showing comparable activity (95 and 96% inhibition at the 60 µmol/kg dose). The oligomeric compounds having formulas Xa and XIIa also showed comparable $ED_{50}$s. The oligomeric compounds having formulas VIa and Xa did not exhibit significant hepatotoxicity whereas the oligomeric compound having nucleosides with Formula XIIa did exhibit significant hepatotoxicity at the higher dose.

Methods of using the oligomeric compounds are also provided. In certain embodiments, methods are provided wherein a cell is contacted with an oligomeric compound of the invention that is complementary to a target RNA. The cell can be in an animal preferably a human. The target RNA is selected from any RNA that would result in some benefit but preferably mRNA, pre-mRNA and micro RNA. In certain embodiments, the target RNA is cleaved as a result of interaction with an oligomeric compound thereby inhibiting its function. The efficiency of the methods can be evaluated by looking at a variety of criteria or end points such as evaluating the antisense activity by detecting the levels of a target RNA, detecting the level of a protein or by detecting one or more phenotypic effects.

The bicyclic nucleosides provided herein are useful for modifying otherwise unmodified oligomeric compounds at one or more positions. Such modified oligomeric compounds can be described as having a particular motif. The term "motif" refers to the pattern of modified nucleosides relative to unmodified or differentially modified nucleosides in an oligomeric compound. Certain motifs that can be prepared using the carbocyclic bicyclic nucleosides provided herein include but are not limited to a gapped motif, a hemimer motif, a blockmer motif, a fully modified motif, a positionally modified motif and an alternating motif. In conjunction with these motifs a wide variety of internucleoside linkages can also be used including but not limited to phosphodiester and phosphorothioate linkages used uniformly or in combinations. The positioning of carbocyclic bicyclic nucleosides and the use of linkage strategies can be easily optimized for the best activity for a particular target.

Representative U.S. patents that teach the preparation of representative motifs include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety. Motifs are also disclosed in International Applications PCT/US2005/019219, filed Jun. 2, 2005 and published as WO 2005/121371 on Dec. 22, 2005 and PCT/US2005/019220, filed Jun. 2, 2005 and published as WO 2005/121372 on Dec. 22, 2005; each of which is incorporated by reference herein in its entirety.

In certain embodiments, gapped oligomeric compounds are provided having one or more bicyclic nucleosides of one of formulas Ia, Ib, Ic and or Id located at each of the 3' and 5'-terminal positions flanking an internal region of nucleosides. The internal nucleosides, in certain embodiments, are β-D-2'-deoxyribonucleosides. In a further embodiment they are β-D-2'-deoxyribonucleosides in combination with one or more other sugar modified nucleosides or β-D-ribonucleosides.

In one embodiment, the term "gapmer" or "gapped oligomeric compound" refers to a chimeric oligomeric compound comprising a central or internal region (a "gap") and an external region on either side of the central or internal region (the "wings"), wherein the gap comprises at least one modification that is different from that of each wing. Such modifications include nucleobase, monomeric linkage, and sugar modifications as well as the absence of modification (unmodified). Thus, in certain embodiments, the nucleotide linkages in each of the wings are different than the nucleotide linkages in the gap. In certain embodiments, each wing comprises nucleotides with high affinity modifications and the gap comprises nucleotides that do not comprise that modification. In certain embodiments, the nucleotides in the gap and the nucleotides in the wings all comprise high affinity modifications, but the high affinity modifications in the gap are different than the high affinity modifications in the wings. In certain embodiments, the modifications in the wings are the same as one another. In certain embodiments, the modifications in the wings are different from each other. In certain embodiments, nucleotides in the gap are unmodified and nucleotides in the wings are modified. In preferred embodiments, the modifications are N-alkoxyamino bicyclic nucleosides.

In one embodiment the term "gapmer" or "gapped oligomeric compound" is meant to include a contiguous sequence of nucleosides that is divided into 3 regions, an internal region having an external region on each of the 5' and 3' ends. The regions are differentiated from each other at least by having different sugar groups that comprise the nucleosides. The types of nucleosides that are generally used to differentiate the regions of a gapped oligomeric compound include β-D-ribonucleosides, β-D-deoxyribonucleosides, 2'-modified nucleosides, 4'-thio modified nucleosides, 4'-thio-2'-modified nucleosides, and bicyclic sugar modified nucleosides. Each of the regions of a gapped oligomeric compound are essentially uniformly modified e.g. the sugar groups are essentially identical with the internal region having different sugar groups than each of the external regions. The internal region or the gap generally comprises β-D-deoxyribonucleosides but can be a sequence of sugar modified nucleosides. In certain embodiments, the gapped oligomeric compounds comprise an internal region of β-D-deoxyribonucleosides with both of the external regions comprising modified nucleosides. Examples of gapped oligomeric compounds are illustrated in the example section.

In certain embodiments, gapped oligomeric compounds are provided comprising one or two bicyclic nucleosides at the 5'-end, two or three bicyclic nucleosides at the 3'-end and an internal region of from 10 to 16 nucleosides. In certain embodiments, gapped oligomeric compounds are provided comprising one bicyclic nucleoside at the 5'-end, two bicyclic nucleosides at the 3'-end and an internal region of from 10 to 16 nucleosides. In certain embodiments, gapped oligomeric compounds are provided comprising one bicyclic nucleoside analog at the 5'-end, two bicyclic nucleosides at the 3'-end and an internal region of from 10 to 14 nucleosides. In certain embodiments, the internal region is essentially a contiguous sequence of β-D-deoxyribonucleosides. In another embodiment, oligomeric compounds are provided that further include one or more 5' or 3'-terminal groups such as a conjugate group that include but are not limited to further modified or unmodified nucleosides, linked conjugate groups and other groups known to the art skilled. In one aspect, oligomeric compounds are provided comprising bicyclic nucleosides selected from formulas Ia, Ib, Ic and Id.

In certain embodiments, gapped oligomeric compounds are provided that are from about 10 to about 21 nucleosides in length. In another embodiment, gapped oligomeric compounds are provided that are from about 10 to about 16 nucleosides in length. In another embodiment, gapped oligomeric compounds are provided that are from about 12 to about 16 nucleosides in length. In a further embodiment, gapped oligomeric compounds are provided that are from about 12 to about 14 nucleosides in length. In a further embodiment, gapped oligomeric compounds are provided that are from about 10 to about 14 nucleosides in length.

The terms "substituent" and "substituent group," as used herein, are meant to include groups that are typically added to other groups or parent compounds to enhance desired properties or give desired effects. Substituent groups can be protected or unprotected and can be added to one available site or to many available sites in a parent compound. Substituent groups may also be further substituted with other substituent groups and may be attached directly or via a linking group such as an alkyl or hydrocarbyl group to a parent compound. Such groups include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxy (—O—$R_{aa}$), aryl, aralkyl, heterocyclic, heteroaryl, heteroarylalkyl, amino (—$NR_{bb}R_{cc}$), imino(=$NR_{bb}$), amido (—C(O)N—$R_{bb}R_{cc}$ or —N($R_{bb}$)C(O)$R_{aa}$), azido (—$N_3$), nitro (—$NO_2$), cyano (—CN), carbamido (—OC(O)$NR_{bb}R_{cc}$ or —N($R_{bb}$)C(O)O$R_{aa}$), ureido (—N($R_{bb}$)C(O)$NR_{bb}R_{cc}$), thioureido (—N($R_{bb}$)C(S)$NR_{bb}R_{cc}$), guanidinyl (—N($R_{bb}$)C(=$NR_{bb}$)$NR_{bb}R_{cc}$), amidinyl (—C(=$NR_{bb}$)$NR_{bb}R_{cc}$ or —N($R_{bb}$)C($NR_{bb}$)$R_{aa}$), thiol (—$SR_{bb}$), sulfinyl (—S(O)$R_{bb}$), sulfonyl (—S(O)$_2R_{bb}$), sulfonamidyl (—S(O)$_2NR_{bb}R_{cc}$ or —N($R_{bb}$)—S(O)$_2R_{bb}$) and conjugate groups. Wherein each $R_{aa}$, $R_{bb}$ and $R_{cc}$ is, independently, H, an optionally linked chemical functional group or a further substituent group with a preferred list including, without limitation H, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by way of example and not limitation, physical properties such as molecular weight, solubility or log P, application properties such as activity against the intended target, and practical properties such as ease of synthesis.

Recursive substituents are an intended aspect of the invention. One of ordinary skill in the art of medicinal and organic chemistry understands the versatility of such substituents. To the degree that recursive substituents are present in a claim of the invention, the total number will be determined as set forth above.

The term "acyl," as used herein, refers to a radical formed by removal of a hydroxyl group from an organic acid and has the general formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substitutent groups.

The term "alicyclic" or "alicyclyl" refers to a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substitutent groups.

The term "aliphatic," as used herein, refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation polyalkoxys, such as polyalkylene glycols, polyamines, and polyimines. Aliphatic groups as used herein may optionally include further substitutent groups.

The term "alkenyl," as used herein, refers to a straight or branched hydrocarbon chain radical containing up to twenty four carbon atoms and having at least one carbon-carbon double bond. Examples of alkenyl groups include, but are not limited to, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substitutent groups.

The term "alkoxy," as used herein, refers to a radical formed between an alkyl group and an oxygen atom wherein the oxygen atom is used to attach the alkoxy group to a parent molecule. Examples of alkoxy groups include, but are not limited to, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substitutent groups.

The term "alkyl," as used herein, refers to a saturated straight or branched hydrocarbon radical containing up to twenty four carbon atoms. Examples of alkyl groups include, but are not limited to, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred. The term "lower alkyl" as used herein includes from 1 to about 6 carbon atoms. Alkyl groups as used herein may optionally include one or more further substitutent groups.

The term "alkynyl," as used herein, refers to a straight or branched hydrocarbon radical containing up to twenty four carbon atoms and having at least one carbon-carbon triple bond. Examples of alkynyl groups include, but are not limited to, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substitutent groups.

The term "aminoalkyl" as used herein, refers to an amino substituted alkyl radical. This term is meant to include $C_1$-$C_{12}$ alkyl groups having an amino substituent at any position and wherein the alkyl group attaches the aminoalkyl group to the parent molecule. The alkyl and/or amino portions of the aminoalkyl group can be further substituted with substituent groups.

The terms "aralkyl" and "arylalkyl," as used herein, refer to a radical formed between an alkyl group and an aryl group wherein the alkyl group is used to attach the aralkyl group to a parent molecule. Examples include, but are not limited to, benzyl, phenethyl and the like. Aralkyl groups as used herein may optionally include further substituent groups attached to the alkyl, the aryl or both groups that form the radical group.

The terms "aryl" and "aromatic," as used herein, refer to a mono- or polycyclic carbocyclic ring system radicals having one or more aromatic rings. Examples of aryl groups include, but are not limited to, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups. The terms "halo" and "halogen," as used herein, refer to an atom selected from fluorine, chlorine, bromine and iodine.

The terms "heteroaryl," and "heteroaromatic," as used herein, refer to a radical comprising a mono- or poly-cyclic aromatic ring, ring system or fused ring system wherein at least one of the rings is aromatic and includes one or more heteroatom. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include, but are not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. Heteroaryl radicals can be attached to a parent molecule directly or through a linking moiety such as an aliphatic group or hetero atom. Heteroaryl groups as used herein may optionally include further substituent groups.

The term "heteroarylalkyl," as used herein, refers to a heteroaryl group as previously defined having an alky radical that can attach the heteroarylalkyl group to a parent molecule. Examples include, but are not limited to, pyridinylmethyl, pyrimidinylethyl, napthyridinylpropyl and the like. Heteroarylalkyl groups as used herein may optionally include further substituent groups on one or both of the heteroaryl or alkyl portions.

The term "heterocyclic radical" as used herein, refers to a radical mono-, or poly-cyclic ring system that includes at least one heteroatom and is unsaturated, partially saturated or fully saturated, thereby including heteroaryl groups. Heterocyclic is also meant to include fused ring systems wherein one or more of the fused rings contain at least one heteroatom and the other rings can contain one or more heteroatoms or optionally contain no heteroatoms. A heterocyclic group typically includes at least one atom selected from sulfur, nitrogen or oxygen. Examples of heterocyclic groups include, [1,3] dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl and the like. Heterocyclic groups as used herein may optionally include further substituent groups.

The term "hydrocarbyl" includes groups comprising C, O and H. Included are straight, branched and cyclic groups having any degree of saturation. Such hydrocarbyl groups can include one or more heteroatoms selected from N, O and S and can be further mono or poly substituted with one or more substituent groups.

The term "mono or poly cyclic structure" as used herein includes all ring systems that are single or polycyclic having rings that are fused or linked and is meant to be inclusive of single and mixed ring systems individually selected from aliphatic, alicyclic, aryl, heteroaryl, aralkyl, arylalkyl, heterocyclic, heteroaryl, heteroaromatic, heteroarylalkyl. Such mono and poly cyclic structures can contain rings that are uniform or have varying degrees of saturation including fully saturated, partially saturated or fully unsaturated. Each ring can comprise ring atoms selected from C, N, O and S to give rise to heterocyclic rings as well as rings comprising only C ring atoms which can be present in a mixed motif such as for example benzimidazole wherein one ring has only carbon ring atoms and the fused ring has two nitrogen atoms. The mono or poly cyclic structures can be further substituted with substituent groups such as for example phthalimide which has two =O groups attached to one of the rings. In another aspect, mono or poly cyclic structures can be attached to a parent molecule directly through a ring atom, through a substituent group or a bifunctional linking moiety.

The term "oxo" refers to the group (=O).

The term "bicyclic nucleic acid" or "BNA" or "bicyclic nucleoside" or "bicyclic nucleotide" refers to a nucleoside or nucleotide wherein the furanose portion of the nucleoside includes a bridge connecting two carbon atoms on the furanose ring, thereby forming a bicyclic ring system.

The term "chimeric oligomeric compound" or "chimeric oligonucleotide" refers to an oligomeric compound or an oligonucleotide having at least one sugar, nucleobase or internucleoside linkage that is modified relative to naturally occurring linked nucleosides. The remainder of the sugars, nucleobases and internucleoside linkages can be independently modified or unmodified wherein each nucleoside and linkage can be the same or different.

The terms "stable compound" and "stable structure" are meant to indicate a compound that is sufficiently robust to survive isolation to a useful degree of purity from a reaction mixture, and formulation into an efficacious therapeutic agent. Only stable compounds are contemplated herein.

Linking groups or bifunctional linking moieties such as those known in the art can be used with the oligomeric compounds provided herein. Linking groups are useful for attachment of chemical functional groups, conjugate groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as a chemical functional group or a conjugate group. In certain embodiments, the linker comprises a chain structure or an oligomer of repeating units such as ethylene glycol or amino acid units. Examples of functional groups that are routinely used in bifunctional linking moieties include, but are not limited to, electrophiles for reacting with nucleophilic groups and nucleophiles for reacting with electrophilic groups. In certain embodiments, bifunctional linking moieties include amino, hydroxyl, carboxylic acid, thiol, unsaturations (e.g., double or triple bonds), and the like. Some nonlimiting examples of bifunctional linking moieties include 8-amino-3,6-dioxaoctanoic acid (ADO), succinimidyl 4-(N-maleimidomethyl)cyclohexane-1-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, oligomeric compounds are modified by covalent attachment of one or more 3' or 5'-terminal groups. The term "terminal group" as used herein is meant to include useful groups known to the art skilled that can be placed on one or both of the 3' and 5'-ends of an oligomeric compound for various purposes such as enabling the tracking of the oligomeric compound (a fluorescent label or other reporter group), improving the pharmacokinetics or pharmacodynamics of the oligomeric compound (a group for enhancing uptake and delivery) or enhancing one or more other desirable properties of the oligomeric compound (group for improving nuclease stability or binding affinity). In certain embodiments, 3' and 5'-terminal groups include without limitation, one or more modified or unmodified nucleosides, conjugate groups, capping groups, phosphate moieties and protecting groups.

In certain embodiments, oligomeric compounds are modified by covalent attachment of one or more conjugate groups. In general, conjugate groups modify one or more properties of the attached oligomeric compound including but not limited to pharmakodynamic, pharmacokinetic, binding, absorption, cellular distribution, cellular uptake, charge and clearance. Conjugate groups are routinely used in the chemical arts and are linked directly or via an optional linking moiety or linking group to a parent compound such as an oligomeric compound. A preferred list of conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes.

The term "protecting group," as used herein, refers to a labile chemical moiety which is known in the art to protect reactive groups including without limitation, hydroxyl, amino and thiol groups, against undesired reactions during synthetic procedures. Protecting groups are typically used selectively and/or orthogonally to protect sites during reactions at other reactive sites and can then be removed to leave the unprotected group as is or available for further reactions. Protecting groups as known in the art are described generally in Greene and Wuts, Protective Groups in Organic Synthesis, 3rd edition, John Wiley & Sons, New York (1999).

Groups can be selectively incorporated into oligomeric compounds of the invention as precursors. For example an amino group can be placed into a compound of the invention as an azido group that can be chemically converted to the amino group at a desired point in the synthesis. Generally, groups are protected or present as precursors that will be inert to reactions that modify other areas of the parent molecule for conversion into their final groups at an appropriate time. Further representative protecting or precursor groups are discussed in Agrawal, et al., Protocols for Oligonucleotide Conjugates, Eds, Humana Press; New Jersey, 1994; Vol. 26 pp. 1-72.

Examples of hydroxyl protecting groups include, but are not limited to, acetyl, t-butyl, t-butoxymethyl, methoxymethyl, tetrahydropyranyl, 1-ethoxyethyl, 1-(2-chloroethoxy)ethyl, p-chlorophenyl, 2,4-dinitrophenyl, benzyl, 2,6-dichlorobenzyl, diphenylmethyl, p-nitrobenzyl, bis(2-acetoxyethoxy)methyl (ACE), 2-trimethylsilylethyl, trimethylsilyl, triethylsilyl, t-butyldimethylsilyl, t-butyldiphenylsilyl, triphenylsilyl, [(triisopropylsilyl)oxy]methyl (TOM), benzoylformate, chloroacetyl, trichloroacetyl, trifluoroacetyl, pivaloyl, benzoyl, p-phenylbenzoyl, 9-fluorenylmethyl carbonate, mesylate, tosylate, triphenylmethyl (trityl), monomethoxytrityl, dimethoxytrityl (DMT), trimethoxytrityl, 1(2-fluorophenyl)-4-methoxypiperidin-4-yl (FPMP), 9-phenylxanthine-9-yl (Pixyl) and 9-(p-methoxyphenyl)xanthine-9-yl (MOX). Where more preferred hydroxyl protecting groups include, but are not limited to, benzyl, 2,6-dichlorobenzyl, t-butyldimethylsilyl, t-butyldiphenylsilyl, benzoyl, mesylate, tosylate, dimethoxytrityl (DMT), 9-phenylxanthine-9-yl (Pixyl) and 9-(p-methoxyphenyl)xanthine-9-yl (MOX).

Examples of amino protecting groups include, but are not limited to, carbamate-protecting groups, such as 2-trimethylsilylethoxycarbonyl (Teoc), 1-methyl-1-(4-biphenyl)-1)-ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide-protecting groups, such as formyl, acetyl, trihaloacetyl, benzoyl, and nitrophenylacetyl; sulfonamide-protecting groups, such as 2-nitrobenzenesulfonyl; and imine- and cyclic imide-protecting groups, such as phthalimido and dithiasuccinoyl.

Examples of thiol protecting groups include, but are not limited to, triphenylmethyl (trityl), benzyl (Bn), and the like.

In certain embodiments, oligomeric compounds are prepared by connecting nucleosides with optionally protected phosphorus containing internucleoside linkages. Representative protecting groups for phosphorus containing internucleoside linkages such as phosphodiester and phosphorothioate linkages include β-cyanoethyl, diphenylsilylethyl, δ-cyanobutenyl, cyano p-xylyl (CPX), N-methyl-N-trifluoroacetyl ethyl (META), acetoxy phenoxy ethyl (APE) and butene-4-yl groups. See for example U.S. Pat. Nos. 4,725,677 and Re. 34,069 (β-cyanoethyl); Beaucage, S. L. and Iyer, R. P., Tetrahedron, 49 No. 10, pp. 1925-1963 (1993); Beaucage, S. L. and Iyer, R. P., Tetrahedron, 49 No. 46, pp. 10441-10488 (1993); Beaucage, S. L. and Iyer, R. P., Tetrahedron, 48 No. 12, pp. 2223-2311 (1992).

The term "orthogonally protected" refers to functional groups which are protected with different classes of protecting groups, wherein each class of protecting group can be removed in any order and in the presence of all other classes (see, Barany, G. and Merrifield, R. B., *J. Am. Chem. Soc.*, 1977, 99, 7363; idem, 1980, 102, 3084.) Orthogonal protection is widely used in for example automated oligonucleotide synthesis. A functional group is deblocked in the presence of one or more other protected functional groups which is not affected by the deblocking procedure. This deblocked functional group is reacted in some manner and at some point a further orthogonal protecting group is removed under a different set of reaction conditions. This allows for selective chemistry to arrive at a desired compound or oligomeric compound.

In certain embodiments, compounds having reactive phosphorus groups useful for forming internucleoside linkages are provided including for example phosphodiester and phosphorothioate internucleoside linkages. Such reactive phosphorus groups are known in the art and contain phosphorus atoms in $P^{III}$ or $P^V$ valence state including, but not limited to, phosphoramidite, H-phosphonate, phosphate triesters and phosphorus containing chiral auxiliaries. A preferred synthetic solid phase synthesis utilizes phosphoramidites ($P^{III}$ chemistry) as reactive phosphites. The intermediate phosphite compounds are subsequently oxidized to the $P^V$ state using known methods to yield, in certain embodiments, phosphodiester or phosphorothioate internucleotide linkages. Additional reactive phosphates and phosphites are disclosed in Tetrahedron Report Number 309 (Beaucage and Iyer, Tetrahedron, 1992, 48, 2223-2311).

As used herein the term "internucleoside linkage or internucleoside linking group" is meant to include all manner of internucleoside linking groups known in the art including but not limited to, phosphorus containing internucleoside linking groups such as phosphodiester and phosphorothioate, non-phosphorus containing internucleoside linking groups such as formacetyl and methyleneimino, and neutral non-ionic internucleoside linking groups such as amide-3 (3'-CH$_2$—C(=O)—N(H)-5), amide-4 (3'-CH$_2$—N(H)—C(=O)-5').

Specific examples of oligomeric compounds useful in this invention include oligonucleotides containing modified e.g. non-naturally occurring internucleoside linkages. Two main classes of internucleoside linkages are defined by the presence or absence of a phosphorus atom. Modified internucleoside linkages having a phosphorus atom include, but are not limited to, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity can comprise a single 3' to 3' linkage at the 3'-most internucleotide linkage, i.e. a single inverted nucleoside residue which may be abasic (the nucleobase is missing or has a hydroxyl group in place thereof). Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Modified internucleoside linkages not having a phosphorus atom include, but are not limited to, those that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH$_2$ component parts. In the context of this invention, the term "oligonucleoside" refers to a sequence of two or more nucleosides that are joined by internucleoside linkages that do not have phosphorus atoms.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

Internucleoside linking groups also include neutral internucleoside linking groups which can include a phosphorus atom or not. As used herein the phrase "neutral internucleoside linkage" is intended to include internucleoside linkages that are non-ionic. Neutral internucleoside linkages include but are not limited to phosphotriesters, methylphosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetal (3'-O—CH$_2$—O-5'), and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook Eds. ACS Symposium Series 580; Chapters 3 and 4, (pp. 40-65)). Further neutral internucleoside linkages include nonionic linkages comprising mixed N, O, S and CH$_2$ component parts.

The compounds described herein contain one or more asymmetric centers and thus give rise to enantiomers, diastereomers, and other stereoisomeric forms that may be defined, in terms of absolute stereochemistry, as (R)- or (S)-, α or β, or as (D)- or (L)- such as for amino acids. All such possible isomers, as well as their racemic and optically pure forms are applicable to the oligomeric compounds provided herein. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., Enantiomers, Racemates, and Resolutions (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

As used herein the term "oligomeric compound" refers to a polymer having at least a region that is capable of hybridizing to a nucleic acid molecule. The term "oligomeric compound" includes oligonucleotides, oligonucleotide analogs and oligonucleosides as well as nucleotide mimetics and/or mixed polymers comprising nucleic acid and non-nucleic acid components. The term "oligomeric compound" also includes polymers comprising linked monomeric subunits wherein the monomeric subunits include nucleosides, modified nucleosides, nucleoside analogs, nucleoside mimetics as well as non-nucleic acid components such as conjugate groups. In certain embodiments, mixtures of monomeric subunits such as but not limited to those listed provide oligomeric compounds having enhanced properties for uses such as therapeutics and diagnostics. The bicyclic nucleosides provided herein are classified as a modified nucleosides as the base and ribose sugar are still present. The monomeric subunits can be linked by naturally occurring phosphodiester internucleoside linkages or alternatively by any of a plurality of internucleoside linkages disclosed herein such as but not limited to phosphoro-thioate internucleoside linkages or mixtures thereof.

In general, an oligomeric compound comprises a backbone of linked monomeric subunits wherein each linked monomeric subunit is directly or indirectly attached to a heterocyclic base moiety. Oligomeric compounds may also include monomeric subunits that are not linked to a heterocyclic base moiety thereby providing abasic sites. The linkages joining the monomeric subunits, the sugar moieties or surrogates and the heterocyclic base moieties can be independently modified. The linkage-sugar unit, which may or may not include a heterocyclic base, may be substituted with a mimetic such as the monomers in peptide nucleic acids. The ability to modify or substitute portions or entire monomers at each position of an oligomeric compound gives rise to a large number of possible motifs.

Oligomeric compounds are routinely prepared linearly but can be joined or otherwise prepared to be circular and may also include branching. Oligomeric compounds can combined to form double stranded constructs such as for example two strands hybridized to form double stranded compositions. The double stranded compositions can be linked or separate and can include overhangs on the ends.

As is known in the art, a nucleoside is a base-sugar combination. The base portion of the nucleoside is normally a heterocyclic base moiety. The two most common classes of such heterocyclic bases are purines and pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. The respective ends of this linear polymeric structure can be joined to form a circular structure by hybridization or by formation of a covalent bond. However, open linear structures are generally desired. Within the oligonucleotide structure, the phosphate groups are commonly referred to as forming the internucleoside linkages of the oligonucleotide. The normal internucleoside linkage of RNA and DNA is a 3' to 5' phosphodiester linkage.

In the context of this invention, the term "oligonucleotide" refers to an oligomer or polymer of ribonucleic acid (RNA) or deoxyribonucleic acid (DNA). This term includes oligonucleotides composed of naturally-occurring nucleobases, sugars and covalent internucleoside linkages. The term "oligonucleotide analog" refers to oligonucleotides that have one or more non-naturally occurring portions. Such non-naturally occurring oligonucleotides are often desired over naturally occurring forms because of desirable properties such as, for example, enhanced cellular uptake, enhanced affinity for nucleic acid target and increased stability in the presence of nucleases.

In the context of this invention, the term "oligonucleoside" refers to a sequence of nucleosides that are joined by internucleoside linkages that do not have phosphorus atoms.

Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include, but are not limited to, siloxane, sulfide, sulfoxide, sulfone, acetyl, formacetyl, thioformacetyl, methylene formacetyl, thioformacetyl, alkenyl, sulfamate, methyleneimino, methylenehydrazino, sulfonate, sulfonamide, amide and others having mixed N, O, S and $CH_2$ component parts.

Representative U.S. patents that teach the preparation of the above oligonucleotides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

The term "nucleobase" or "heterocyclic base moiety" as used herein, is intended to by synonymous with "nucleic acid base or mimetic thereof." In general, a nucleobase is any substructure that contains one or more atoms or groups of atoms capable of hydrogen bonding to a base of a nucleic acid.

As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($-C\equiv C-CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido [5,4-b][1,4]benzoxazin-2(3H)-one), carbazole cytidine (2H-pyrimido[4,5-b]indol-2-one), pyridoindole cytidine (H-pyrido[3',2': 4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993.

Modified nucleobases include, but are not limited to, universal bases, hydrophobic bases, promiscuous bases, size-expanded bases, and fluorinated bases as defined herein. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

The oligomeric compounds provided herein may also contain one or more nucleosides having modified sugar moieties. The furanosyl sugar ring can be modified in a number of ways including substitution with a substituent group (2', 3', 4' or 5'), bridging to form a BNA and substitution of the 4'-0 with a heteroatom such as S or N(R). Some representative U.S. patents that teach the preparation of such modified sugars include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; 5,700,920; 6,600,032 and International Application PCT/US2005/019219, filed Jun. 2, 2005 and published as WO 2005/121371 on Dec. 22, 2005 certain of which are commonly owned with the instant application, and each of which is herein incorporated by reference in its entirety. A representative list of preferred modified sugars includes but is not limited to substituted sugars having a 2'-F, 2'-OCH$_2$ or a 2'-O(CH$_2$)$_2$-OCH$_3$ (2'-MOE or simply MOE) substituent group; 4'-thio modified sugars and bicyclic modified sugars.

As used herein the term "nucleoside mimetic" is intended to include those structures used to replace the sugar or the sugar and the base not the linkage at one or more positions of an oligomeric compound such as for example nucleoside mimetics having morpholino or bicyclo[3.1.0]iexyl sugar mimetics e.g. non furanose sugar units with a phosphodiester linkage. The term "sugar surrogate" overlaps with the slightly broader term "nucleoside mimetic" but is intended to indicate replacement of the sugar unit (furanose ring) only. The term "nucleotide mimetic" is intended to include those structures used to replace the nucleoside and the linkage at one or more positions of an oligomeric compound such as for example peptide nucleic acids or morpholinos (morpholinos linked by —N(H)—C(═O)—O— or other non-phosphodiester linkage).

In certain embodiments, the oligomeric compounds provided herein can comprise from about 8 to about 80 nucleosides and/or modified nucleosides or mimetics in length. One of ordinary skill in the art will appreciate that the invention embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleosides and/or modified nucleosides or mimetics in length, or any range therewithin.

In certain embodiments, the oligomeric compounds provided herein are 8 to 40 nucleosides and/or modified nucleosides or mimetics in length. One having ordinary skill in the art will appreciate that this embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleosides and/or modified nucleosides or mimetics in length, or any range therewithin.

In certain embodiments, the oligomeric compounds of the invention are 8 to 20 nucleosides and/or modified nucleosides or mimetics in length. One having ordinary skill in the art will appreciate that this embodies oligomeric compounds of 8, 9, 10, 11, 12, 13, 14, 15, 16, 17, 18, 19 or 20 nucleosides and/or modified nucleosides or mimetics in length, or any range therewithin.

In certain embodiments, the oligomeric compounds of the invention are 10 to 16 nucleosides and/or modified nucleosides or mimetics in length. One having ordinary skill in the art will appreciate that this embodies oligomeric compounds of 10, 11, 12, 13, 14, 15 or 16 nucleosides and/or modified nucleosides or mimetics in length, or any range therewithin.

In certain embodiments, the oligomeric compounds of the invention are 12 to 16 nucleosides and/or modified nucleosides or mimetics in length. One having ordinary skill in the art will appreciate that this embodies oligomeric compounds of 12, 13, 14, 15 or 16 nucleosides and/or modified nucleosides or mimetics in length, or any range therewithin.

In certain embodiments, the oligomeric compounds of the invention are 10 to 14 nucleosides and/or modified nucleosides or mimetics in length. One having ordinary skill in the art will appreciate that this embodies oligomeric compounds of 10, 11, 12, 13 or 14 nucleosides and/or modified nucleosides or mimetics in length, or any range therewithin.

In certain embodiments, the oligomeric compounds are provided having of any of a variety of ranges of lengths of linked monomer subunits. In certain embodiments, the invention provides oligomeric compounds consisting of X-Y linked monomer subunits, where X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X<Y. For example, in certain embodiments, the invention provides oligomeric compounds comprising: 8-9, 8-10, 8-11, 8-12, 8-13, 8-14, 8-15, 8-16, 8-17, 8-18, 8-19, 8-20, 8-21, 8-22, 8-23, 8-24, 8-25, 8-26, 8-27, 8-28, 8-29, 8-30, 9-10, 9-11, 9-12, 9-13, 9-14, 9-15, 9-16, 9-17, 9-18, 9-19, 9-20, 9-21, 9-22, 9-23, 9-24, 9-25, 9-26, 9-27, 9-28, 9-29, 9-30, 10-11, 10-12, 10-13, 10-14, 10-15, 10-16, 10-17, 10-18, 10-19, 10-20, 10-21, 10-22, 10-23, 10-24, 10-25, 10-26, 10-27, 10-28, 10-29, 10-30, 11-12, 11-13, 11-14, 11-15, 11-16, 11-17, 11-18, 11-19, 11-20, 11-21, 11-22, 11-23, 11-24, 11-25, 11-26, 11-27, 11-28, 11-29, 11-30, 12-13, 12-14, 12-15, 12-16, 12-17, 12-18, 12-19, 12-20, 12-21, 12-22, 12-23, 12-24, 12-25, 12-26, 12-27, 12-28, 12-29, 12-30, 13-14, 13-15, 13-16, 13-17, 13-18, 13-19, 13-20, 13-21, 13-22, 13-23, 13-24, 13-25, 13-26, 13-27, 13-28, 13-29, 13-30, 14-15, 14-16, 14-17, 14-18, 14-19, 14-20, 14-21, 14-22, 14-23, 14-24, 14-25, 14-26, 14-27, 14-28, 14-29, 14-30, 15-16, 15-17, 15-18, 15-19, 15-20, 15-21, 15-22, 15-23, 15-24, 15-25, 15-26, 15-27, 15-28, 15-29, 15-30, 16-17, 16-18, 16-19, 16-20, 16-21, 16-22, 16-23, 16-24, 16-25, 16-26, 16-27, 16-28, 16-29, 16-30, 17-18, 17-19, 17-20, 17-21, 17-22, 17-23, 17-24, 17-25, 17-26, 17-27, 17-28, 17-29, 17-30, 18-19, 18-20, 18-21, 18-22, 18-23, 18-24, 18-25, 18-26, 18-27, 18-28, 18-29, 18-30, 19-20, 19-21, 19-22, 19-23, 19-24, 19-25, 19-26, 19-29, 19-28, 19-29, 19-30, 20-21, 20-22, 20-23, 20-24, 20-25, 20-26, 20-27, 20-28, 20-29, 20-30, 21-22, 21-23, 21-24, 21-25, 21-26, 21-27, 21-28, 21-29, 21-30, 22-23, 22-24, 22-25, 22-26, 22-27, 22-28, 22-29, 22-30, 23-24, 23-25, 23-26, 23-27, 23-28, 23-29, 23-30, 24-25, 24-26, 24-27, 24-28, 24-29, 24-30, 25-26, 25-27, 25-28, 25-29, 25-30, 26-27, 26-28, 26-29, 26-30, 27-28, 27-29, 27-30, 28-29, 28-30, or 29-30 linked monomer subunits.

In certain embodiments, ranges for the length of the oligomeric compounds include 8-16, 8-20, 8-40, 10-12, 10-14, 10-16, 10-18, 10-20, 10-21, 12-14, 12-16, 12-18, 12-20 and 12-24 linked monomer subunits.

In certain embodiments, oligomerization of modified and unmodified nucleosides and mimetics thereof, can be performed according to literature procedures for DNA (Protocols for Oligonucleotides and Analogs, Ed. Agrawal (1993), Humana Press) and/or RNA (Scaringe, Methods (2001), 23, 206-217; Gait et al., Applications of Chemically synthesized RNA in RNA:Protein Interactions, Ed. Smith (1998), 1-36; Gallo et al., Tetrahedron (2001), 57, 5707-5713) synthesis as appropriate. Additional methods for solid-phase synthesis may be found in Caruthers U.S. Pat. Nos. 4,415,732; 4,458, 066; 4,500,707; 4,668,777; 4,973,679; and 5,132,418; and Koster U.S. Pat. Nos. 4,725,677 and Re. 34,069.

Commercially available equipment routinely used for the support medium based synthesis of oligomeric compounds and related compounds is sold by several vendors including, for example, Applied Biosystems (Foster City, Calif.). Any other means for such synthesis known in the art may additionally or alternatively be employed. Suitable solid phase techniques, including automated synthesis techniques, are described in F. Eckstein (ed.), Oligonucleotides and Analogues, a Practical Approach, Oxford University Press, New York (1991).

The synthesis of RNA and related analogs relative to the synthesis of DNA and related analogs has been increasing as efforts in RNAi increase. The primary RNA synthesis strategies that are presently being used commercially include 5'-O-DMT-2'-O-t-butyldimethylsilyl (TBDMS), 5'-O-DMT-2'-O-[1(2-fluorophenyl)-4-methoxypiperidin-4-yl] (FPMP), 2'-O-[(triisopropylsilypoxy]methyl (2'-O—$CH_2$—O—$Si(iPr)_3$ (TOM), and the 5'-O-silyl ether-2'-ACE (5'-O-bis(trimethylsiloxy)cyclododecyloxysilyl ether (DOD)-2'-O-bis(2-acetoxyethoxy)methyl (ACE). A current list of some of the major companies currently offering RNA products include Pierce Nucleic Acid Technologies, Dharmacon Research Inc., Amen Biotechnologies Inc., and Integrated DNA Technologies, Inc. One company, Princeton Separations, is marketing an RNA synthesis activator advertised to reduce coupling times especially with TOM and TBDMS chemistries.

The primary groups being used for commercial RNA synthesis are:

| | |
|---|---|
| TBDMS = | 5'-O-DMT-2'-O-t-butyldimethylsilyl; |
| TOM = | 2'-O-[(triisopropylsilyl)oxy]methyl; |
| DOD/ACE = | (5'-O-bis(trimethylsiloxy)cyclododecyloxysilyl ether-2'-O-bis(2-acetoxyethoxy)methyl |
| FPMP = | 5'-O-DMT-2'-O-[1(2-fluorophenyl)-4-methoxypiperidin-4-yl]. |

In certain embodiments, the aforementioned RNA synthesis strategies and strategies that would be a hybrid of the above e.g. using a 5'-protecting group from one strategy with a 2'-O-protecting from another strategy are included as methods of making oligomers applicable herein.

In the context of this invention, "hybridization" means the pairing of complementary strands of oligomeric compounds.

In certain embodiments, one mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An oligomeric compound is specifically hybridizable when binding of the compound to the target nucleic acid interferes with the normal function of the target nucleic acid to cause a loss of activity, and there is a sufficient degree of complementarity to avoid non-specific binding of the oligomeric compound to non-target nucleic acid sequences under conditions in which specific binding is desired, i.e., under physiological conditions in the case of in vivo assays or therapeutic treatment, and under conditions in which assays are performed in the case of in vitro assays.

"Complementary," as used herein, refers to the capacity for precise pairing of two nucleobases regardless of where the two are located. For example, if a nucleobase at a certain position of an oligomeric compound is capable of hydrogen bonding with a nucleobase at a certain position of a target nucleic acid, the target nucleic acid being a DNA, RNA, or oligonucleotide molecule, then the position of hydrogen bonding between the oligonucleotide and the target nucleic acid is considered to be a complementary position. The oligomeric compound and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

It is understood in the art that the sequence of an oligomeric compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). The oligomeric compounds provided herein can comprise at least about 70%, at least about 80%, at least about 90%, at least about 95%, or at least about 99% sequence complementarity to a target region within the target nucleic acid sequence to which they are targeted. For example, an oligomeric compound in which 18 of 20 nucleobases of the oligomeric compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an oligomeric compound which is 18 nucleobases in length having 4 (four) noncomplementary nucleobases which are flanked by two regions of complete complementarity with the target nucleic acid would have 77.8% overall complementarity with the target nucleic acid and would thus fall within the scope as disclosed herein. Percent complementarity of an oligomeric compound with a region of a target nucleic acid can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656).

Oligomeric compounds provided herein also include without limitation antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these oligomeric compounds may be introduced in the form of single-stranded, double-stranded, circular or hairpin oligomeric compounds and may contain structural elements such as internal or terminal bulges or loops. Once introduced to a system, the oligomeric compounds of the invention may elicit the action of one or more enzymes or structural proteins to effect modification of the target nucleic acid.

One non-limiting example of such an enzyme is RNAse H, a cellular endonuclease which cleaves the RNA strand of an RNA:DNA duplex. It is known in the art that single-stranded oligomeric compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While one form of oligomeric compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

In certain embodiments, "suitable target segments" may be employed in a screen for additional oligomeric compounds that modulate the expression of a selected protein. "Modulators" are those oligomeric compounds that decrease or increase the expression of a nucleic acid molecule encoding a protein and which comprise at least an 8-nucleobase portion which is complementary to a suitable target segment. The screening method comprises the steps of contacting a suitable target segment of a nucleic acid molecule encoding a protein with one or more candidate modulators, and selecting for one or more candidate modulators which decrease or increase the expression of a nucleic acid molecule encoding a protein. In certain embodiments, once it is shown that the candidate modulator or modulators are capable of modulating (e.g. either decreasing or increasing) the expression of a nucleic acid molecule encoding a peptide, the modulator may then be employed in further investigative studies of the function of the peptide, or used as a research, diagnostic, or therapeutic agent.

In certain embodiments, suitable target segments may be combined with their respective complementary antisense oligomeric compounds to form stabilized double-stranded (duplexed) oligonucleotides. Such double stranded oligonucleotide moieties have been shown in the art to modulate target expression and regulate translation as well as RNA processing via an antisense mechanism. Moreover, the double-stranded moieties may be subject to chemical modifications (Fire et al., Nature, 1998, 391, 806-811; Timmons and Fire, Nature 1998, 395, 854; Timmons et al., Gene, 2001, 263, 103-112; Tabara et al., Science, 1998, 282, 430-431; Montgomery et al., Proc. Natl. Acad. Sci. USA, 1998, 95, 15502-15507; Tuschl et al., Genes Dev., 1999, 13, 3191-3197; Elbashir et al., Nature, 2001, 411, 494-498; Elbashir et al., Genes Dev. 2001, 15, 188-200). For example, such double-stranded moieties have been shown to inhibit the target by the classical hybridization of antisense strand of the duplex to the target, thereby triggering enzymatic degradation of the target (Tijsterman et al., Science, 2002, 295, 694-697).

In certain embodiments, the oligomeric compounds provided herein can also be applied in the areas of drug discovery and target validation. The oligomeric compounds can also be used in conjunction with the targets identified herein in drug discovery efforts to elucidate relationships that exist between proteins and a disease state, phenotype, or condition. These methods include detecting or modulating a target peptide comprising contacting a sample, tissue, cell, or organism with the oligomeric compounds, measuring the nucleic acid or protein level of the target and/or a related phenotypic or chemical endpoint at some time after treatment, and optionally comparing the measured value to a non-treated sample or sample treated with a further oligomeric compound of the invention. These methods can also be performed in parallel or in combination with other experiments to determine the function of unknown genes for the process of target validation or to determine the validity of a particular gene product as a target for treatment or prevention of a particular disease, condition, or phenotype.

As used herein, the term "dose" refers to a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual.

In certain embodiments, chemically-modified oligomeric compounds of the invention have a higher affinity for target RNAs than does non-modified DNA. In certain such embodiments, that higher affinity in turn provides increased potency allowing for the administration of lower doses of such compounds, reduced potential for toxicity and improvement in therapeutic index and decreased overall cost of therapy.

Effect of nucleoside modifications on RNAi activity is evaluated according to existing literature (Elbashir et al., Nature (2001), 411, 494-498; Nishikura et al., Cell (2001), 107, 415-416; and Bass et al., Cell (2000), 101, 235-238.)

The oligomeric compounds provided herein can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway. The oligomeric compounds provided herein, either alone or in combination with other oligomeric compounds or therapeutics, can be used as tools in differential and/or combinatorial analyses to elucidate expression patterns of a portion or the entire complement of genes expressed within cells and tissues. Oligomeric compounds can also be effectively used as primers and probes under conditions favoring gene amplification or detection, respectively. These primers and probes are useful in methods requiring the specific detection of nucleic acid molecules encoding proteins and in the amplification of the nucleic acid molecules for detection or for use in further studies. Hybridization of the antisense oligonucleotides, particularly the primers and probes, of the invention with a nucleic acid can be detected by means known in the art. Such means may include conjugation of an enzyme to the oligonucleotide, radiolabelling of the oligonucleotide or any other suitable detection means. Kits using such detection means for detecting the level of selected proteins in a sample may also be prepared.

As one nonlimiting example, expression patterns within cells or tissues treated with one or more oligomeric compounds are compared to control cells or tissues not treated with oligomeric compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds and or oligomeric compounds which affect expression patterns. Examples of methods of gene expression analysis known in the art include DNA arrays or microarrays (Brazma and Vilo, FEBS Lett., 2000, 480, 17-24; Celis, et al., FEBS Lett., 2000, 480, 2-16), SAGE (serial analysis of gene expression)(Madden, et al., Drug Discov. Today, 2000, 5, 415-425), READS (restriction enzyme amplification of digested cDNAs) (Prashar and Weissman, Methods Enzymol., 1999, 303, 258-72), TOGA (total gene expression analysis) (Sutcliffe, et al., Proc. Natl. Acad. Sci. U.S.A., 2000, 97, 1976-81), protein arrays and proteomics (Celis, et al., FEBS Lett., 2000, 480, 2-16; Jung-blut, et al., Electrophoresis, 1999, 20, 2100-10), expressed sequence tag (EST) sequencing (Celis, et al., FEBS Lett., 2000, 480, 2-16; Larsson, et al., J. Biotechnol., 2000, 80, 143-57), subtractive RNA fingerprinting (SuRF) (Fuchs, et al., Anal. Biochem., 2000, 286, 91-98; Larson, et al., Cytometry, 2000, 41, 203-208), subtractive cloning, differential display (DD) (Jurecic and Belmont, Curr. Opin. Microbiol., 2000, 3, 316-21), comparative genomic hybridization (Carulli, et al., J. Cell Biochem. Suppl., 1998, 31, 286-96), FISH (fluorescent in situ hybridization) techniques (Going and Gusterson, Eur. J. Cancer, 1999, 35, 1895-904) and mass spectrometry methods (To, Comb. Chem. High Throughput Screen, 2000, 3, 235-41).

While the monomers, oligomers and methods provided herein have been described with specificity in accordance with certain of their embodiments, the following examples serve only to illustrate the invention and are not intended to limit the same.

EXAMPLE 1

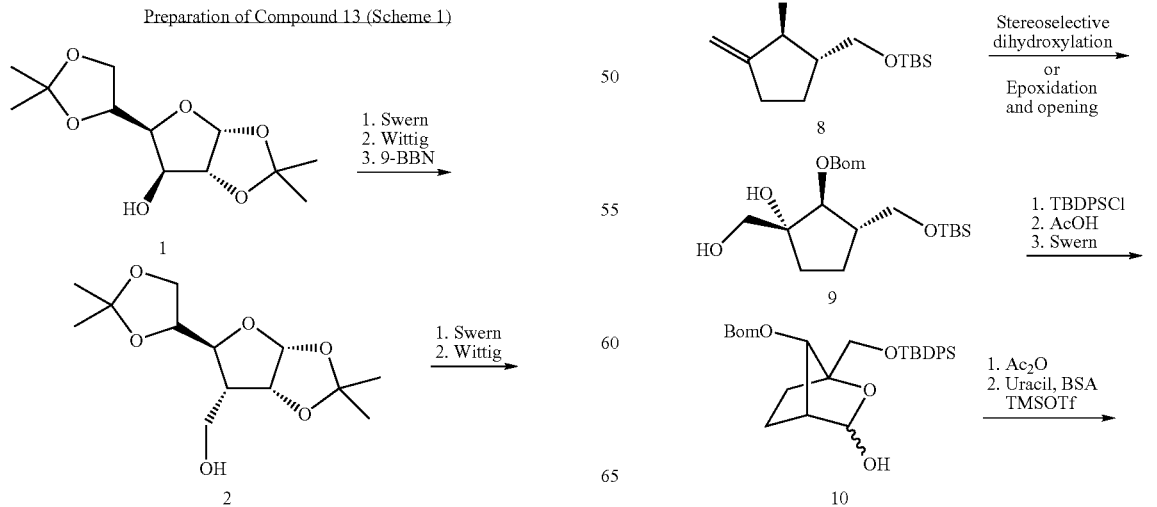

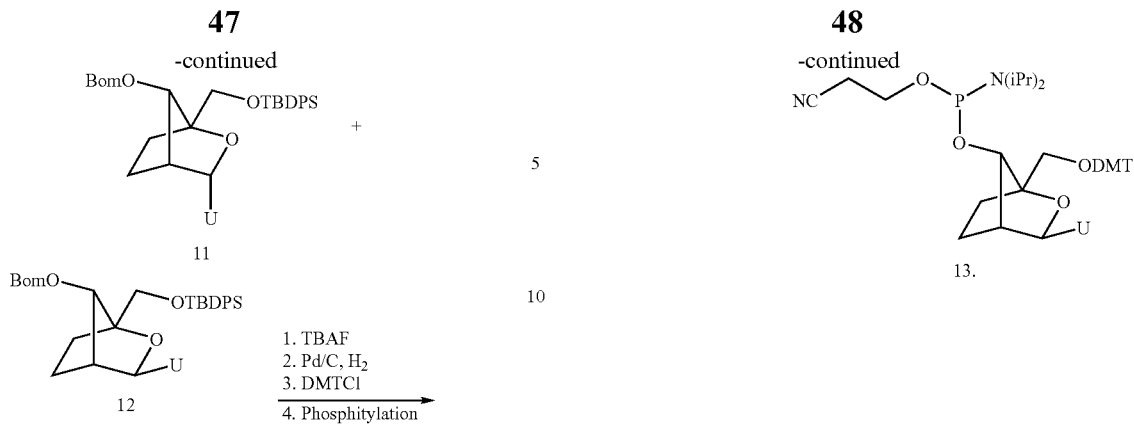
EXAMPLE 2
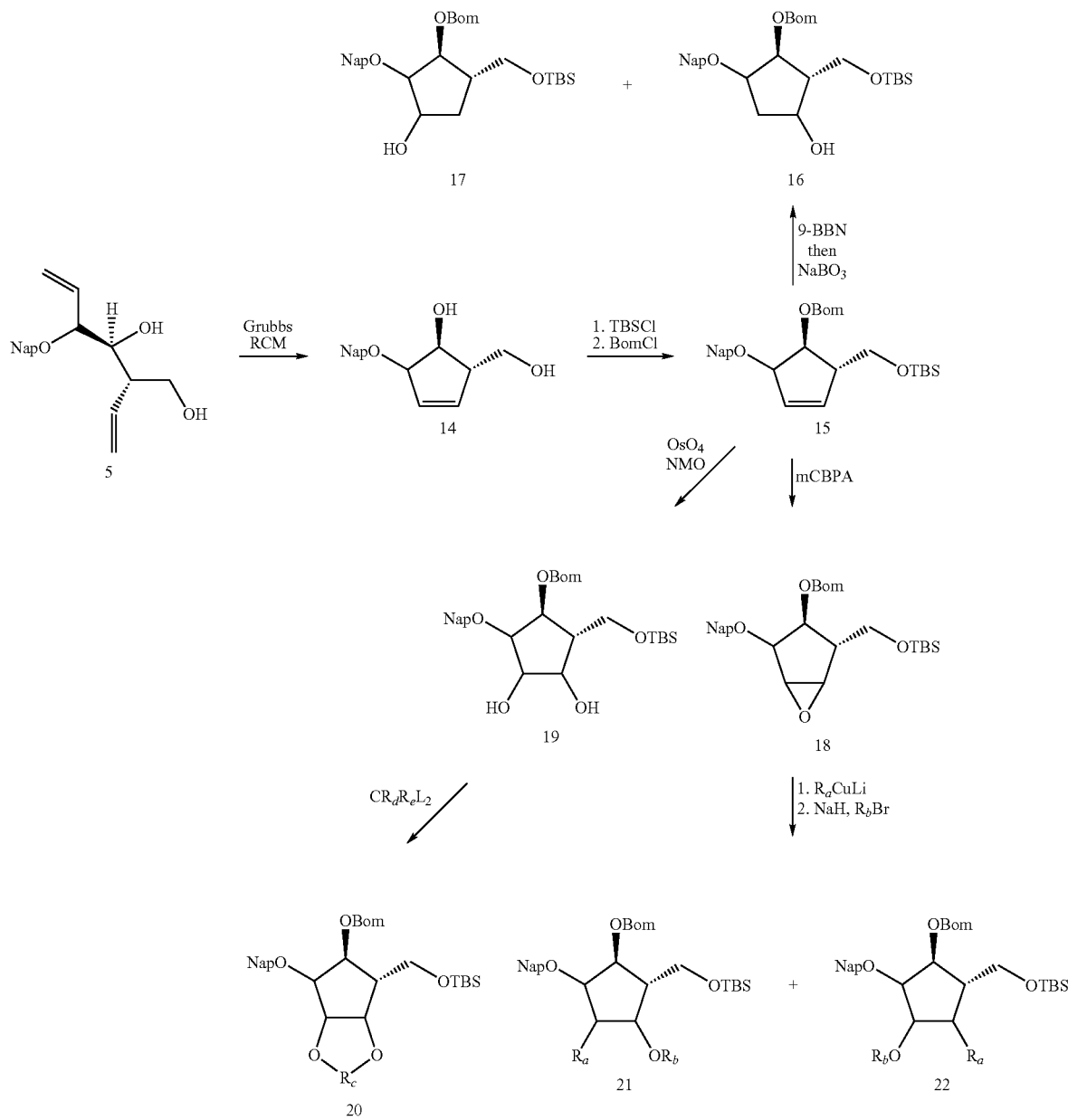

$R_a$ and $R_b$ are, independently, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl or substituted $C_2$-$C_{12}$ alkynyl; and $R_c$ is —$(CR_dR_e)_n$— wherein each $R_d$ and $R_e$ is, independently, H, halogen, $C_1$-$C_{12}$ alkyl, substituted $C_1$-$C_{12}$ alkyl, or a substituent group or $R_d$ and $R_e$ together are a double bonded O or S, n is from 1 to about 4 and each L is independently, Br, I or a leaving group.

EXAMPLE 3

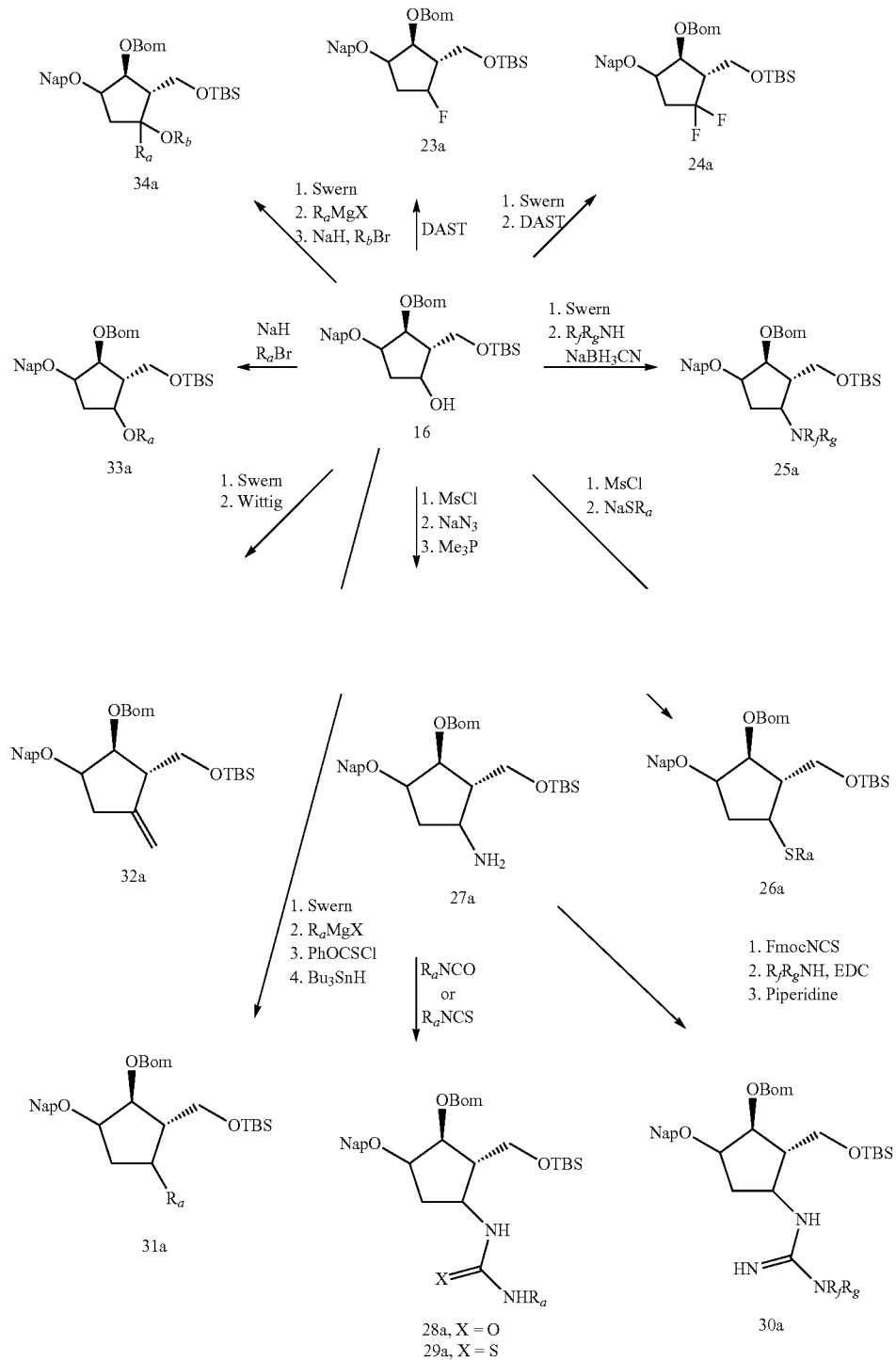

Preparation of Compounds 23a-34a (Scheme 3)

$R_a$ and $R_b$ are, independently, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl or substituted $C_2$-$C_{12}$ alkynyl.

$R_f$ and $R_g$ are, independently, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, O—$C_1$-$C_{12}$ alkyl, substituted O—$C_1$-$C_{12}$ alkyl, S—$C_1$-$C_{12}$ alkyl or substituted S—$C_1$-$C_{12}$ alkyl.

EXAMPLE 4

Preparation of Compounds 23b-34b (Scheme 4)

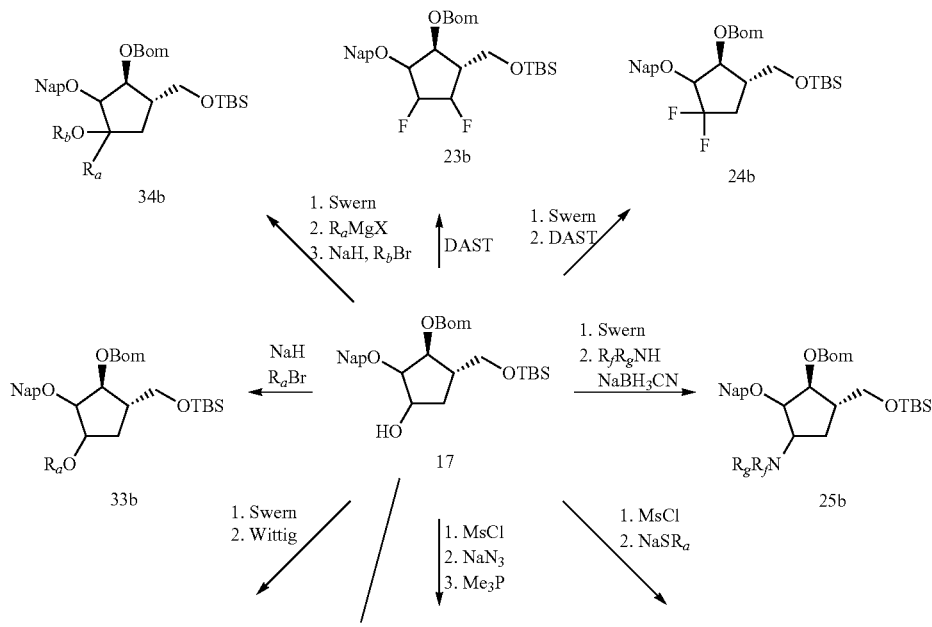

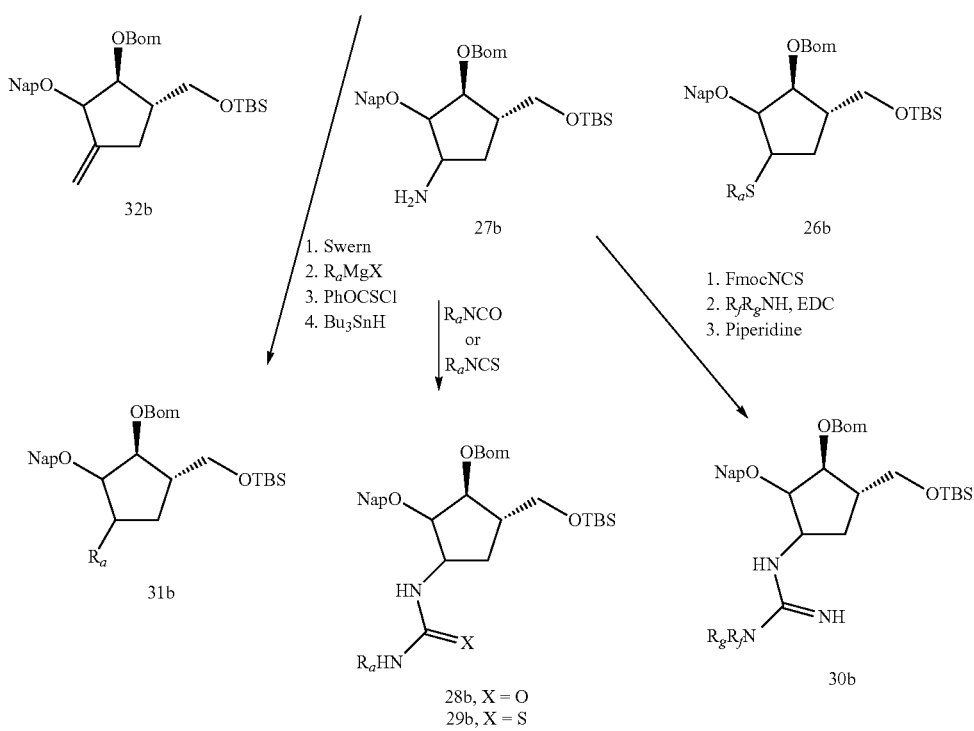

$R_a$ and $R_b$ are, independently, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl or substituted $C_2$-$C_{12}$ alkynyl.

$R_f$ and $R_g$ are, independently, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, O—$C_1$-$C_{12}$ alkyl, substituted O—$C_1$-$C_{12}$ alkyl, S—$C_1$-$C_{12}$ alkyl or substituted S—$C_1$-$C_{12}$ alkyl.

EXAMPLE 5

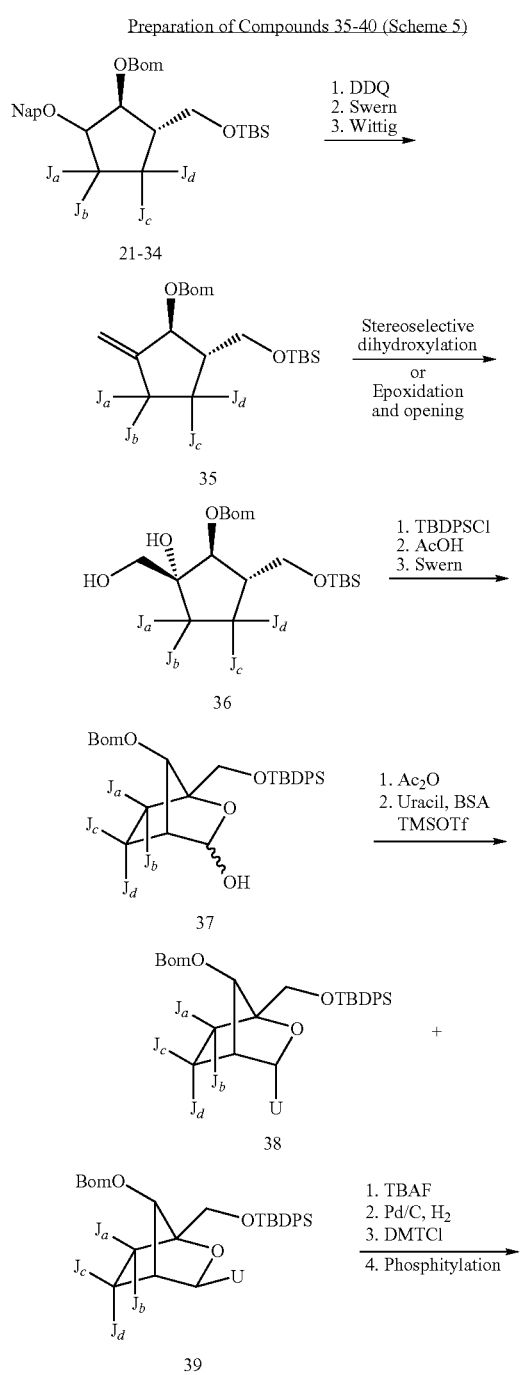

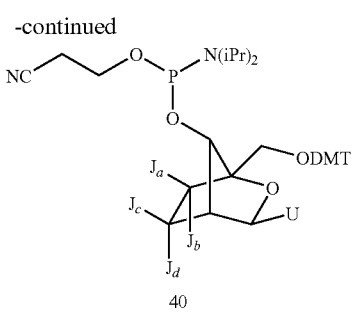

Each $J_a$, $J_b$, $J_c$ and $J_d$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_1$, $SJ_1$, $SOJ_1$, $SO_2J_1$, $NJ_1J_2$, $N_3$, CN, C(=O)$OJ_1$, C(=O)$NJ_1J_2$, C(=O)$J_1$, O—C(=O)NJ J2, N(H)C(=NH)$NJ_1J_2$, N(H)C(=O)$NJ_1J_2$ or N(H)C(=S)$NJ_1J_2$.

EXAMPLE 6

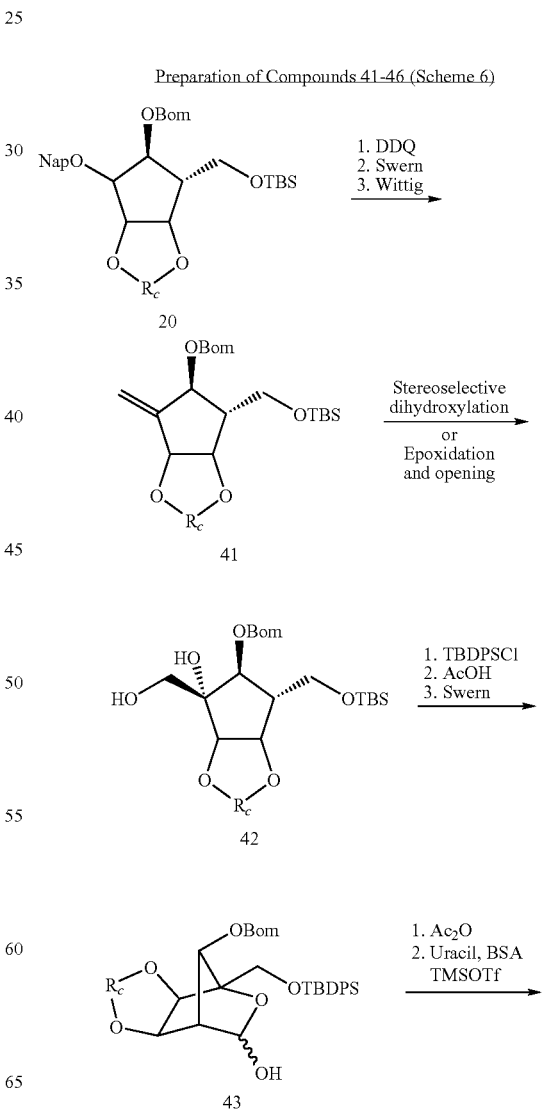

-continued

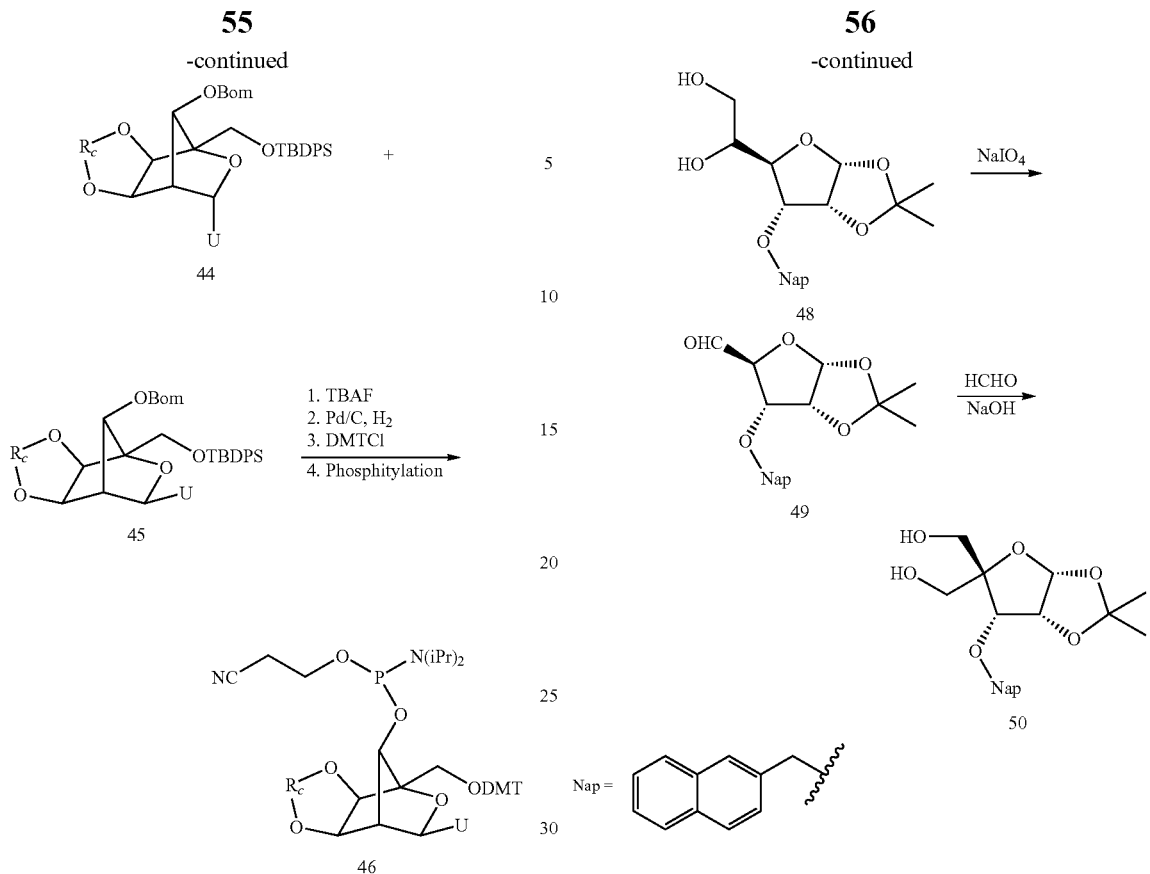

$R_c$ is —$(CR_dR_e)_n$ wherein each $R_d$ and $R_e$ is, independently, H, halogen, $C_1$-$C_{12}$ alkyl, substituted $C_1$-$C_{12}$ alkyl, or a substituent group or $R_d$ and $R_e$ together are a double bonded O or S, n is from 1 to about 4 and each L is independently, Br, I or a leaving group.

EXAMPLE 7

Preparation of 3-O-Naphthylmethyl-4-(hydroxymethyl)-1,2-O-isopropylidene-α-D-erythro-pentofuranose (Compound 50, Scheme 7)

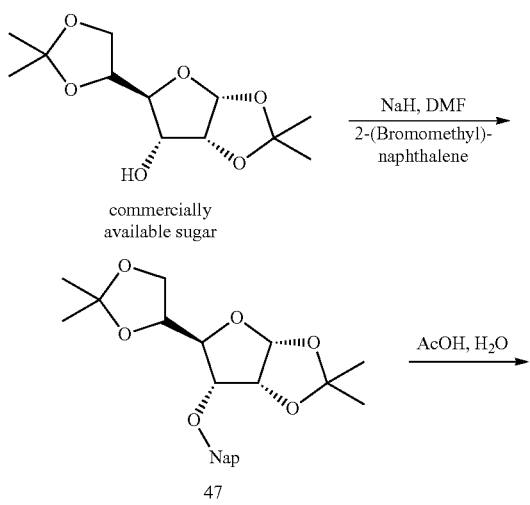

A) Compound 47

Commercially available sugar 1,2:5,6-Di-O-isopropylidene-α-D-allofuranose (135 g, 519.0 mmol, commercially available from Pfanstiehl Laboratories, Inc.; order # D-126) Commercially available sugar 2 (135 g, 519.0 mmol) and 2-(bromomethyl)-naphthalene (126 g, 570.0 mmol) were dissolved in DMF (500 mL) in a three-necked flask (500 mL) and the reaction was cooled in an ice bath. Sodium hydride (60% w/w, 29 g, 727.0 mmol) was carefully added (6 g portions every 10 minutes) to the reaction and the stirring was continued for another 60 minutes after the addition was complete. At this time TLC analysis showed no more starting sugar 2. The reaction was carefully poured onto crushed ice (ca. 500 g) and the resulting slurry was stirred vigorously until all the ice melted. The resulting off-white solid was collected by filtration and suspended in water. The suspension was stirred vigorously using a mechanical stirrer for 30 minutes after which the solid was collected by filtration and suspended in hexanes. The suspension was stirred vigorously for 30 minutes after which the solid was collected by filtration and air dried for 4-6 hours and then dried under high vacuum over $P_2O_5$ for 16 hours to provide Compound 47 (206.0 g, 99%) as an off-white solid. $^1$H NMR (300 MHz, CDCl$_3$) δ: 7.85 (m, 4H), 7.48 (m, 3H), 5.74 (s, 1H), 4.92 (d, 1H, J=11.7), 4.75 (d, 1H, J=11.6), 4.58 (m, 1H), 4.36 (m, 1H), 4.15 (m, 1H), 4.03-3.86 (m, 3H), 1.61 (s, 3H), 1.36 (s, 9H).

B) Compound 48

Compound 47 (200.0 g, 0.5 moles) was added in small portions to a solution of acetic acid (2.2 L) and water (740 mL). The reaction was stirred at room temperature for 16 h after which, TLC analysis (30% EtOAc/hexanes) indicated complete consumption of Compound 47. The reaction was then concentrated under reduced pressure until most of the acetic acid was removed. The remaining solution was poured into a stirred mixture of EtOAc (1 L) and water (1 L). Solid KOH was then added to the above mixture until the aqueous layer was strongly basic (pH>12). The organic layer was then separated, washed with saturated sodium bicarbonate solution, brine, dried (Na$_2$SO$_4$), filtered and concentrated under reduced pressure to provide Compound 48 as a yellow foam, which was used without any further purification.

C) Compound 49

A solution of NaIO$_4$ (107.0 g) in water (3 L) was added over 40 minutes to a stirred (mechanical stirrer) solution of Compound 48 (crude from Step B, above) in dioxane (1.5 L). After 60 minutes the reaction mixture was poured into EtOAc (1.5 L) and the organic layer was separated, washed with water (1 L), brine (1 L), dried (Na$_2$SO$_4$) and concentrated to provide Compound 49 as a yellow oil, which was used without any further purification.

D) Compound 50

Compound 49 (crude from above) was dissolved in a mixture of THF (500) and water (500 mL) and the reaction was cooled in an ice bath. 2N NaOH (600 mL) and formaldehyde (250 mL of a 37% aqueous solution) were added to the reaction and the stirring was continued at room temperature for 3 days. The reaction was then poured into EtOAc (1 L) and washed with water (1 L), brine (1 L) and evaporated under reduced pressure until approximately 200 mL of EtOAc was left (a white precipitate was formed in the process). Hexanes (300 mL) was added to the precipitate and the mixture was allowed to stand for 16 hours after which the white solid was collected by filtration, washed with hexanes and dried under high vacuum over P$_2$O$_5$ to provide Compound 50 as a white solid (124 g, 66% from Compound 47). $^1$H NMR (300 MHz, CDCl$_3$) δ: 7.85 (m, 4H), 7.48 (m, 3H), 5.75 (d, 1H, J=3.9), 4.96 (d, 1H, J=11.8), 4.75 (d, 1H, J=11.8), 4.66 (m, 1H), 4.26 (d, 1H, J=5.2), 3.95 (m, 2H), 3.79 (m, 1H), 3.63 (m, 1H), 2.39 (m, 1H, OH), 1.66 (s, 3H), 1.34 (s, 3H).

EXAMPLE 8

A) Preparation of Compound 51 tert-Butyldiphenylchlorosilane (305.0 mmol, 84.0 mL) was added to a cold (0° C.) stirring solution of diol, Compound 50 (278.0 mmol, 100.0 g) and triethylamine (305 mmol, 43.0 mL) in dichloromethane (600 mL). After the addition was complete, the reaction was warmed to room temperature and the stirring was continued for 16 hours. MeOH (50 mL) was added (to quench the excess TBDPSCl) to the reaction and the stirring was continued for another 2 hours at room temperature. The reaction was then diluted with chloroform and the organic layer was washed with 10% HCl, saturated NaHCO$_3$, brine, dried (Na$_2$SO$_4$) and concentrated to provide a thick oil. Hexanes (150 mL) was added to the oil and the mixture was sonicated until a solution resulted.

The solution was now seeded with a small amount of Compound 51 (previously isolated by column chromatography). After standing for 16 hours additional hexanes was added to the thick slurry and the solid was collected by filtration. The solid was then resuspended in hexanes and stirred vigorously for 30 minutes. The solid was collected by filtration to provide Compound 51 (80.5, 48% g) after drying under high vacuum for 16 hours. The filtrates were combined and concentrated under reduced pressure. The resulting oil was redissolved in minimum amount of hexanes and passed through a plug of silica gel (eluting with 20% EtOAc in hexanes). Fractions containing Compound 51 were combined, concentrated and crystallized as described above to provide a second crop of Compound 51 (20 g, 12%) as a white solid. Further elution of the silica gel plug with 50% EtOAc in hexanes provided pure 51a (40.0 g, 24%) as a thick oil. In addition a mixture of Compound 51 and Compound 51a (ca 15 g, 9%) was also isolated as a thick oil. Compound 51; $^1$H NMR (300 MHz, CDCl$_3$) δ: 7.83 (m, 4H), 7.56 (m, 7H), 7.30 (m, 6H), 5.80 (s, 1H), 4.97 (d, 1H, J=11.4), 4.70 (m, 2H), 4.46 (m, 1H), 3.92-3.66 (m, 4H), 2.39 (m, 1H, OH), 1.67 (s, 3H), 1.37 (s, 3H), 0.92 (s, 9H). Diol 7; $^1$H NMR (300 MHz, CDCl$_3$) □: 7.9-7.3 (m, 17H), 5.71 (d, 1H, J=3.9), 4.86 (d, 1H, J=12.2), 4.74 (d, 1H, J=12.2), 4.56 (m, 1H), 4.22 (d, 1H, J=11.1), 4.18 (m, 1H), 4.07 (d, 1H, J=11.1), 4.02 (dd, 1H, J=4.2, 12.0), 3.64 (dd, 1H, J=9.4, 11.9), 1.89 (m, 1H), 1.25 (s, 6H), 1.05 (s, 9H).

EXAMPLE 9

Preparation of Compound 51 (Scheme 8)

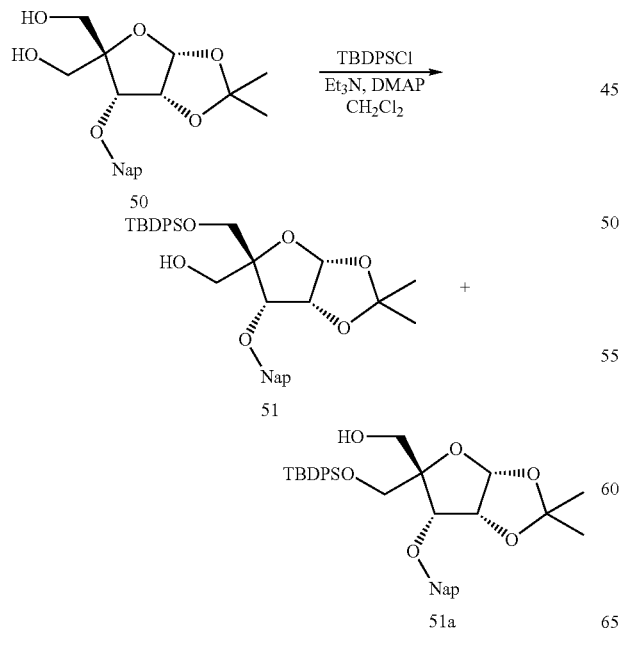

Preparation of Compound 55 (Scheme 9)

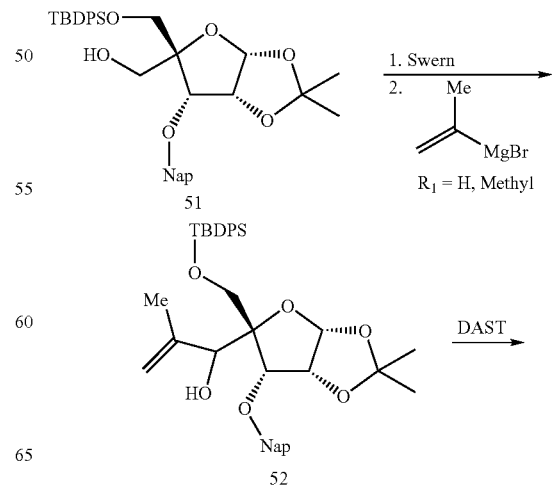

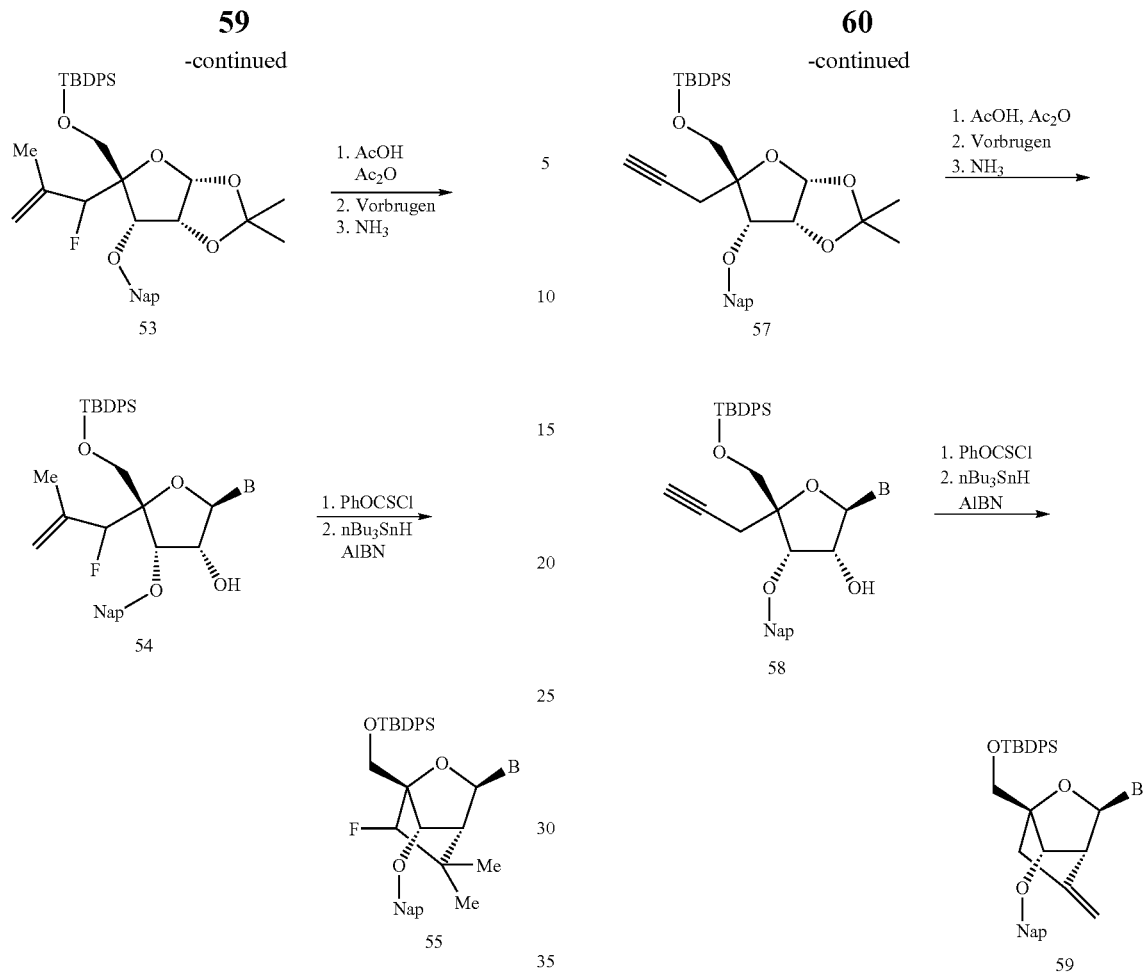
Compound 51 is prepared as per the procedures illustrated in Example 8.
Compound 51 is prepared as per the procedures illustrated in Example 8.
EXAMPLE 10
EXAMPLE 11
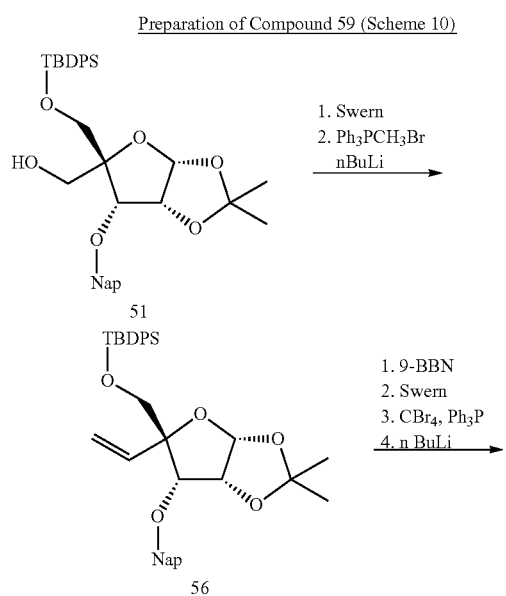
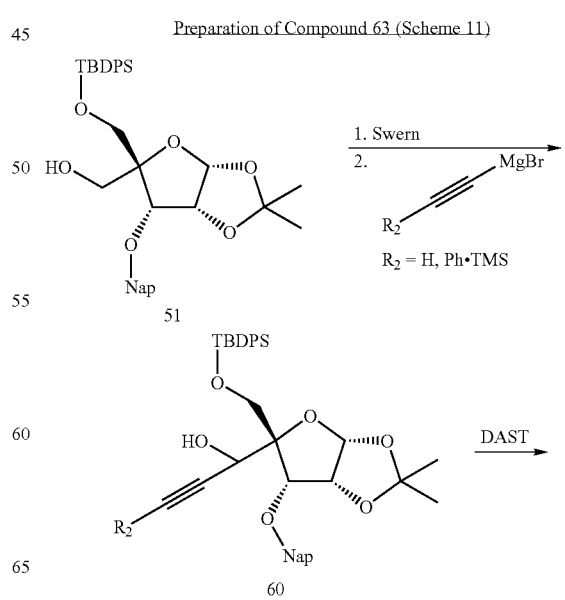

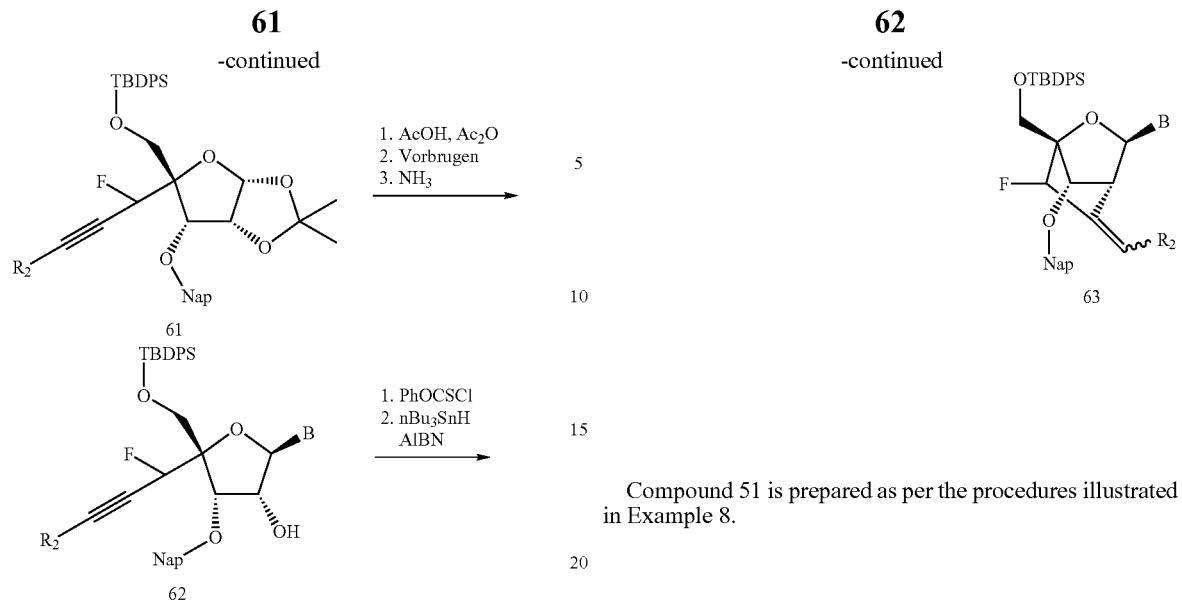
Compound 51 is prepared as per the procedures illustrated in Example 8.
EXAMPLE 12
Preparation of Compounds 65-70 (Scheme 12)
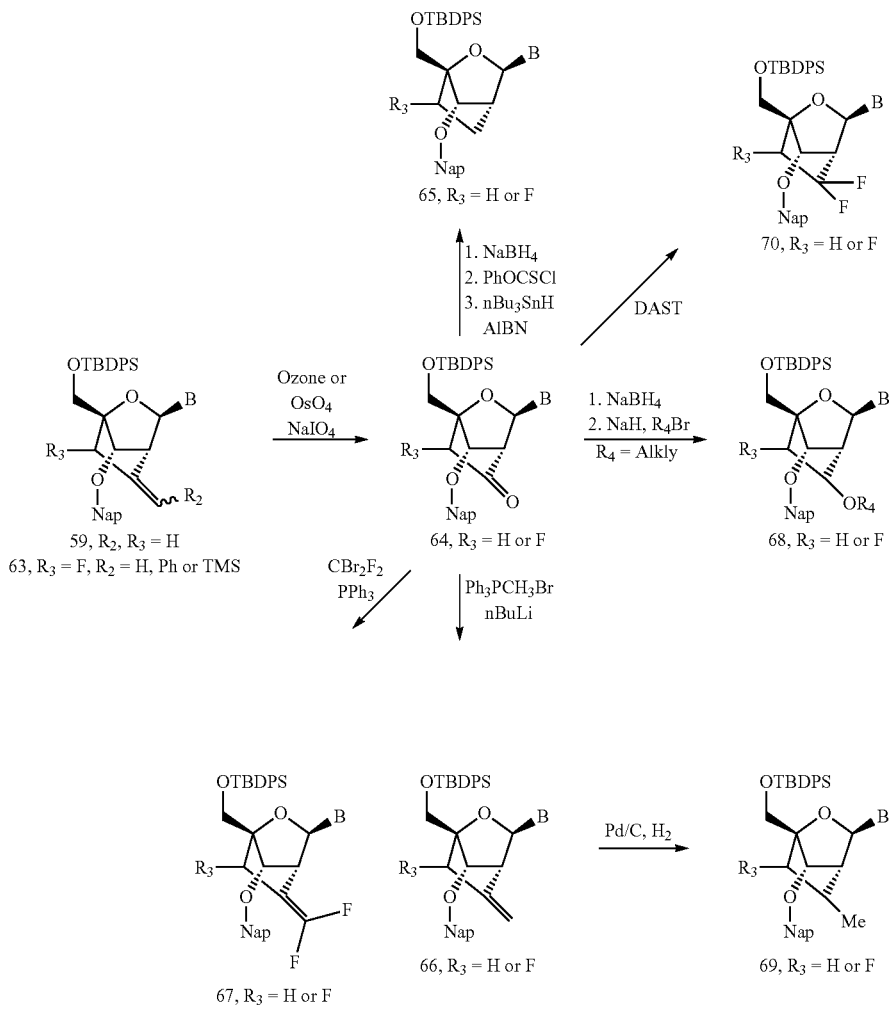

Compounds 59 and 63 are prepared following the procedures illustrated in examples 10 and 11 respectively.
Compound 56 is prepared as per the procedures illustrated in Example 10.
EXAMPLE 13
Preparation of Compound 74 (Scheme 13)
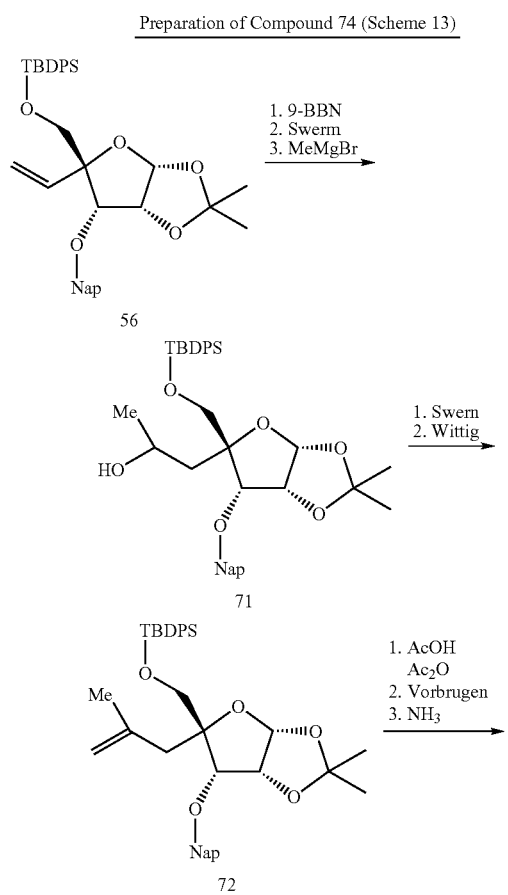
EXAMPLE 14
Preparation of Compound 78 (Scheme 14)
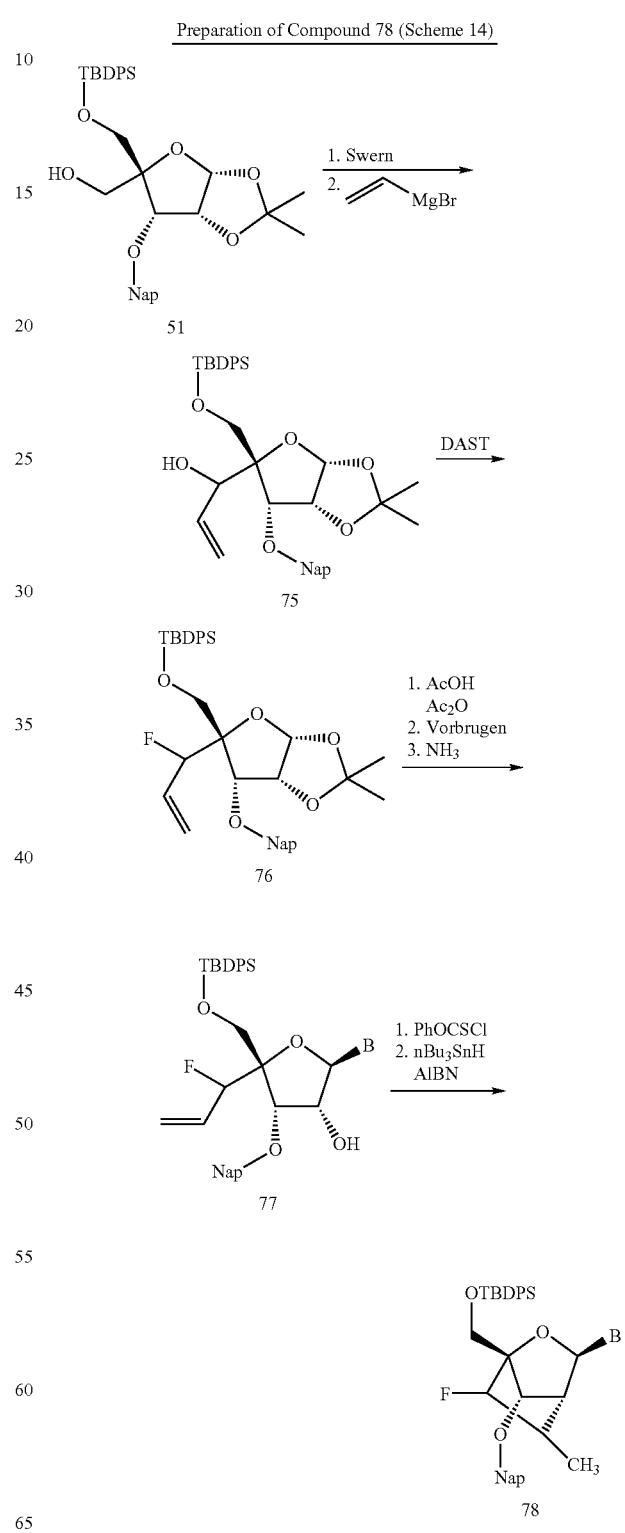

Compound 51 is prepared as per the procedures illustrated in Example 8.
EXAMPLE 15
Preparation of Compound 81 (Scheme 15)
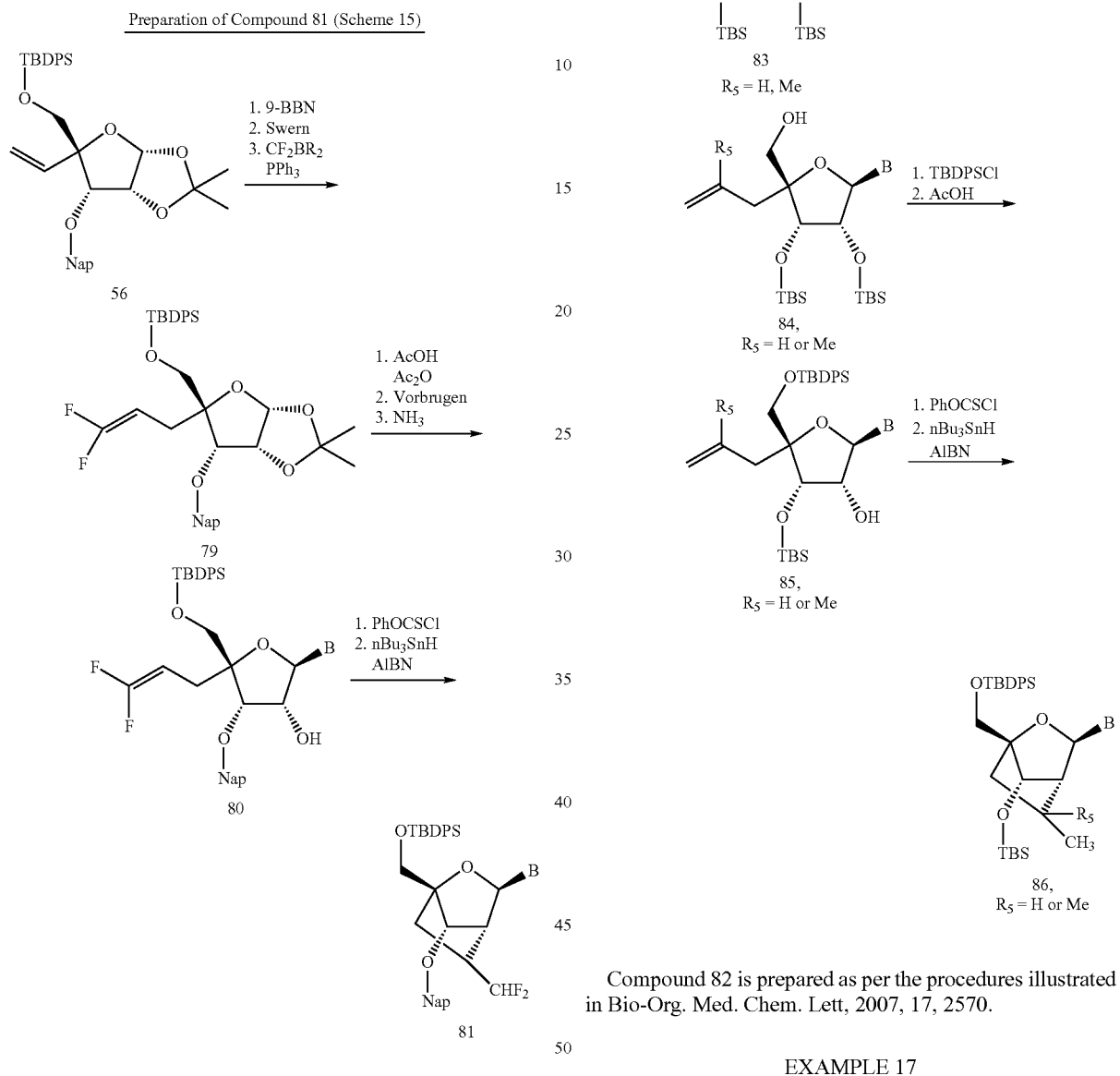
Compound 56 is prepared as per the procedures illustrated in Example 10.
EXAMPLE 16
Preparation of Compound 86 (Scheme 16)
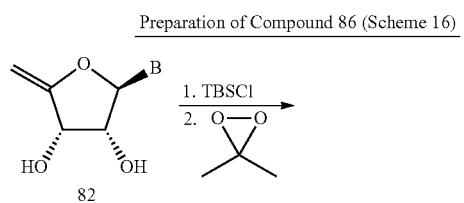
Compound 82 is prepared as per the procedures illustrated in Bio-Org. Med. Chem. Lett, 2007, 17, 2570.
EXAMPLE 17
Preparation of Compound 91 (Scheme 17)

EXAMPLE 18
Preparation of various Compounds represented by Compound 95
(Scheme 18)
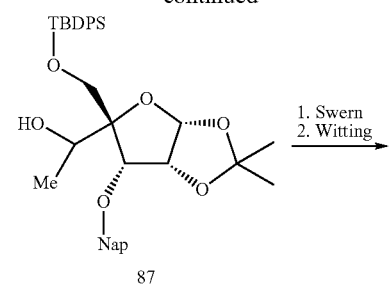
87
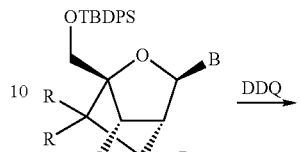
55, 59, 63, 64-70
74, 78, 81, 86, 91
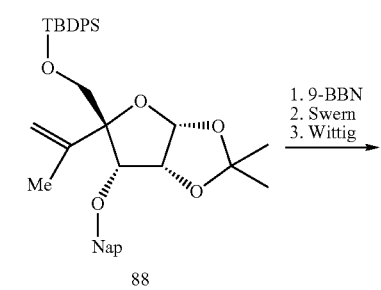
88
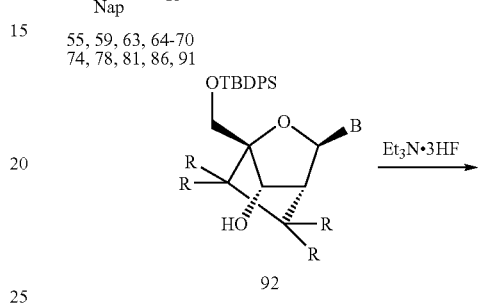
92
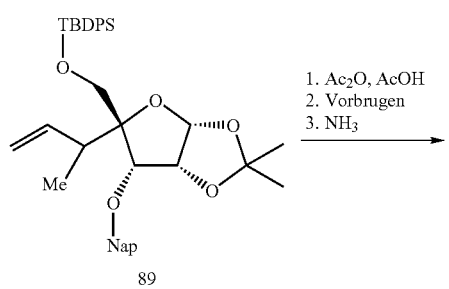
89
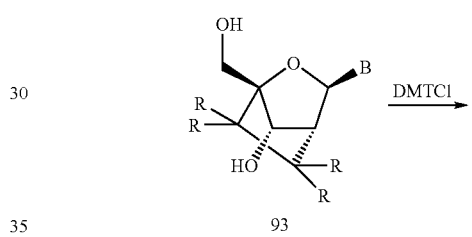
93
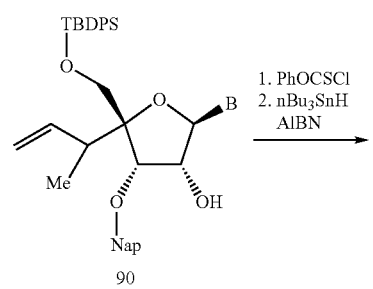
90
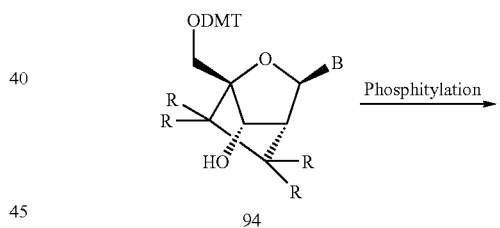
94
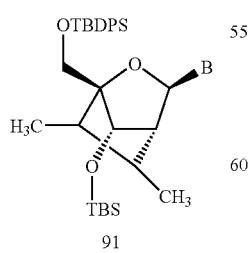
91
95
Compound 51 is prepared as per the procedures illustrated in Example 8.
Compounds 55, 59, 63, 64-70, 74, 78, 81, 86, 91 and 56 are prepared as per the procedures illustrated in examples 9-17 respectively. The final phosphoramidite can incorporate various R groups independently at the 4 indicated positions.

Following the procedures illustrated in examples 9-17 a wide variety of substitutions are possible on the carbocyclic bridge.

EXAMPLE 19

Preparation of 5-methyl DMT phosphoramidite BNA, (1R,3R,4R,7S)-7-[2-cyanoethoxy(diisopropylamino)phosphin oxy]-1-(4,4'-dimethoxytrityloxymethyl)-3-(nucleobase, pyrimidien-1-yl or purine-9-yl)-5-methynyl-2-oxa-bicyclo[2.2.1]heptane (Compound 107, Scheme 19)

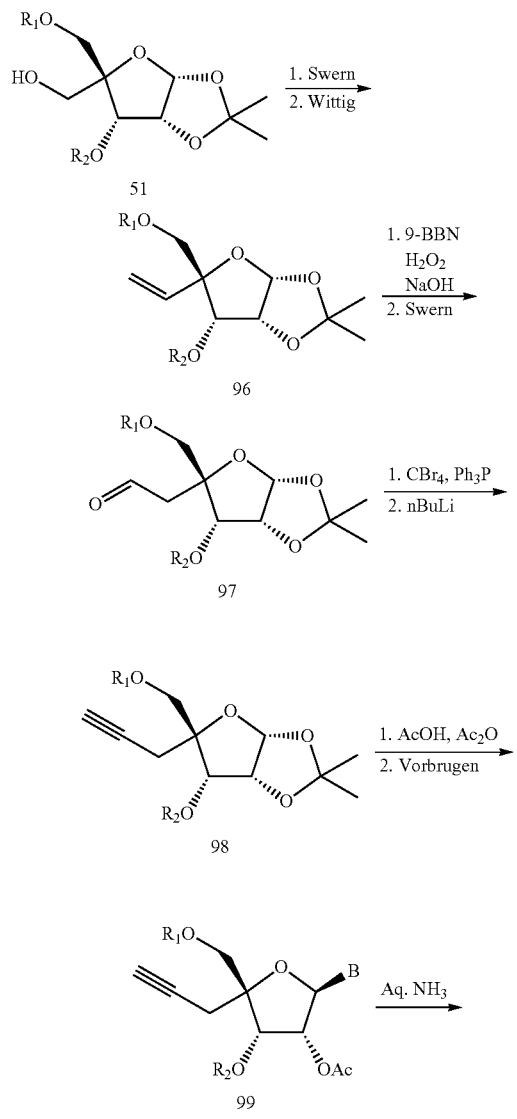

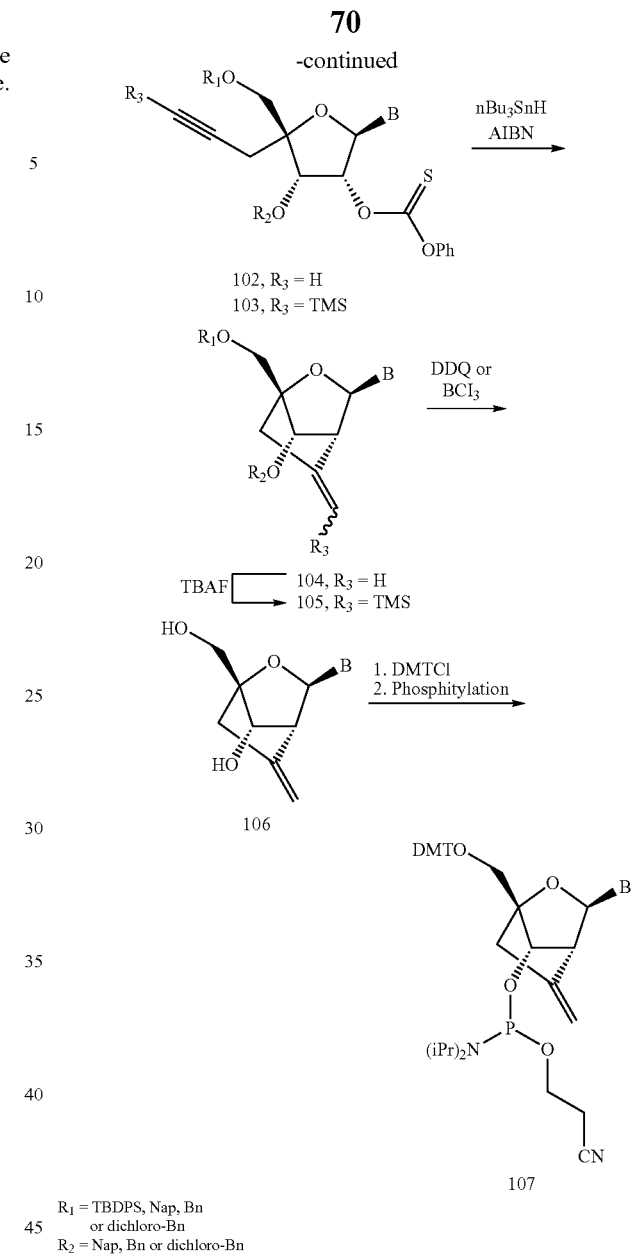

$R_1$ = TBDPS, Nap, Bn or dichloro-Bn
$R_2$ = Nap, Bn or dichloro-Bn

Compound 51 can be prepared as per the procedures illustrated in examples 7 and 8 with $R_1$ TBDPS and $R_2$ as napthyl. Alternate groups for $R_1$ and $R_2$ can easily be prepared using alternate protecting groups.

EXAMPLE 20

Alternate route for the preparation of Compound 107 (Scheme 20)

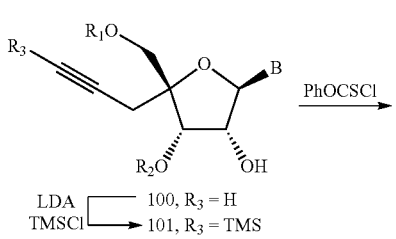

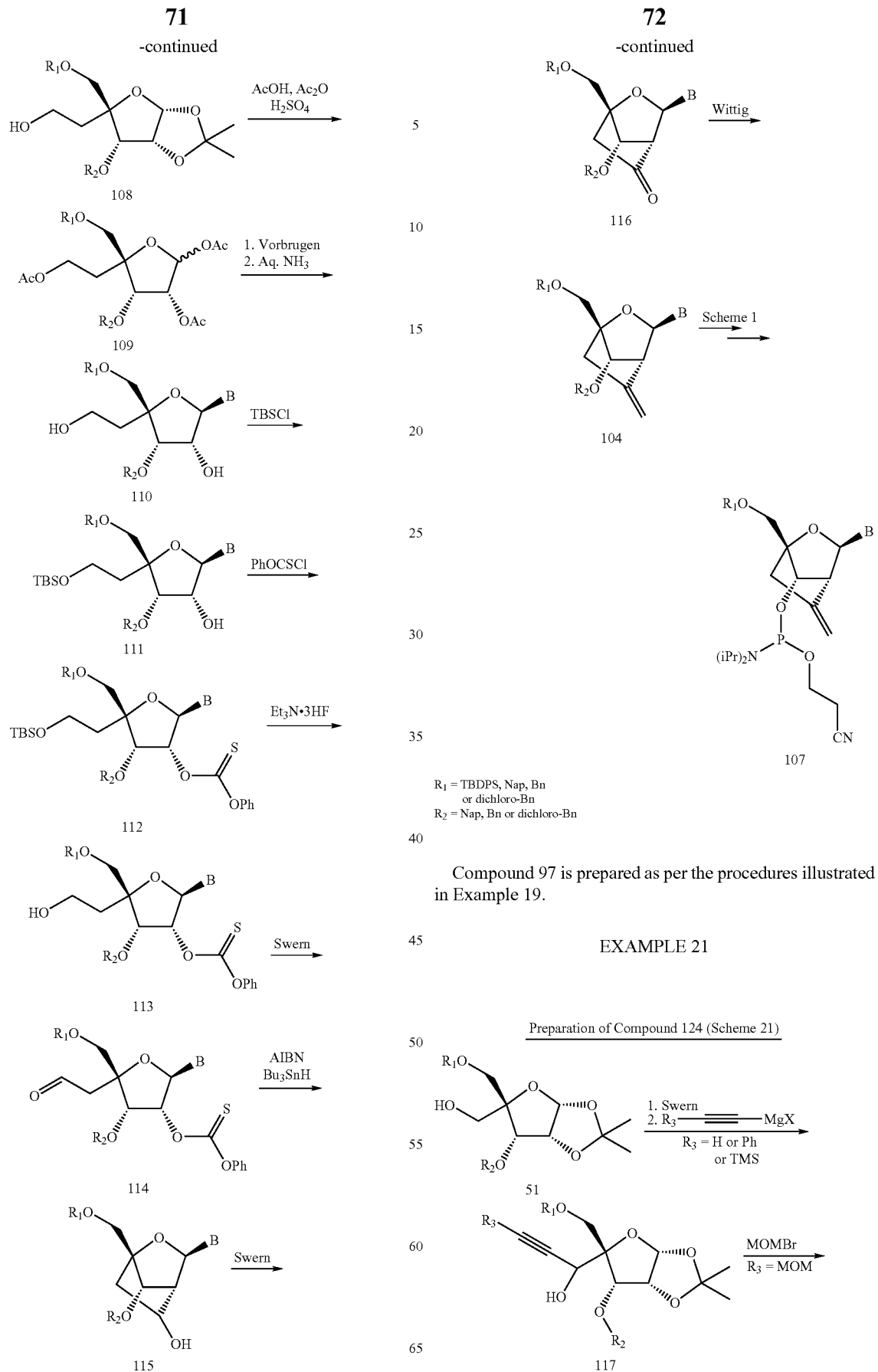
$R_1$ = TBDPS, Nap, Bn or dichloro-Bn
$R_2$ = Nap, Bn or dichloro-Bn
Compound 97 is prepared as per the procedures illustrated in Example 19.
EXAMPLE 21

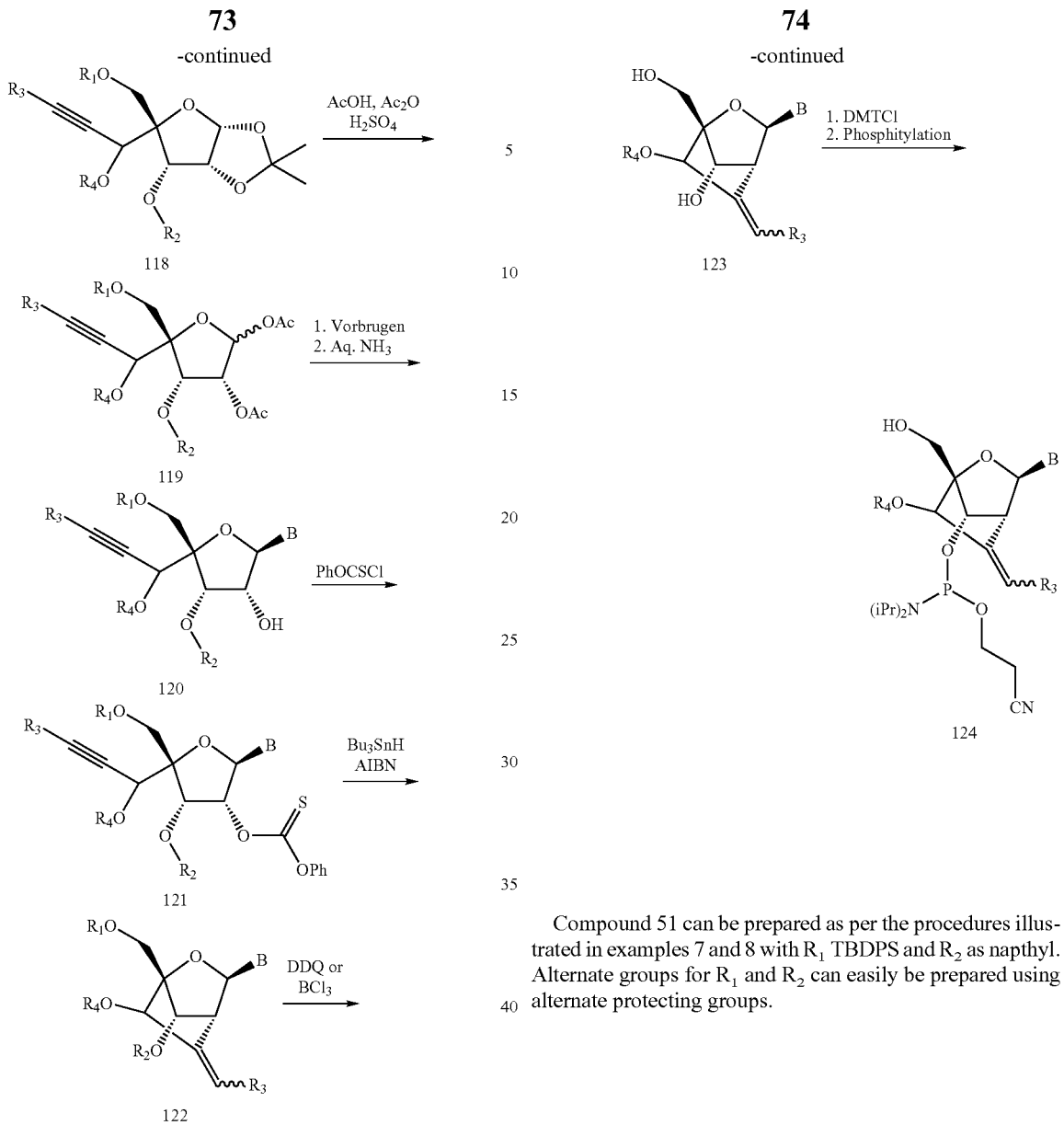
Compound 51 can be prepared as per the procedures illustrated in examples 7 and 8 with $R_1$ TBDPS and $R_2$ as napthyl. Alternate groups for $R_1$ and $R_2$ can easily be prepared using alternate protecting groups.
EXAMPLE 22
Preparation of Compounds 129 and 130 (Scheme 22)
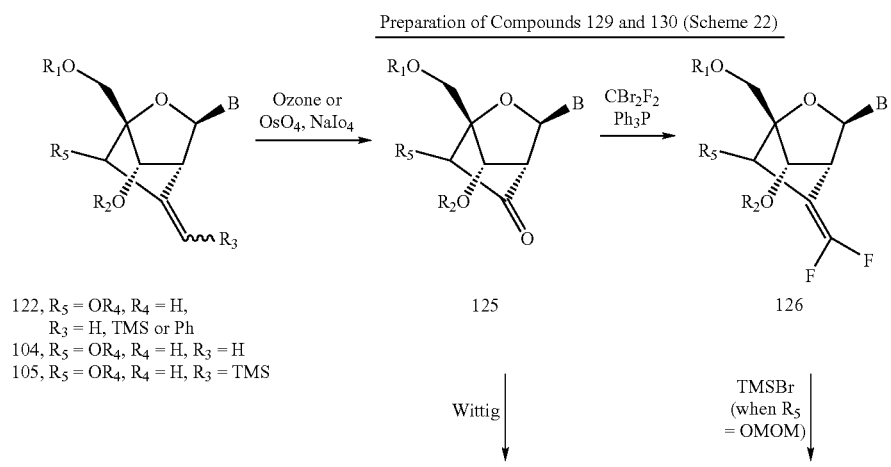

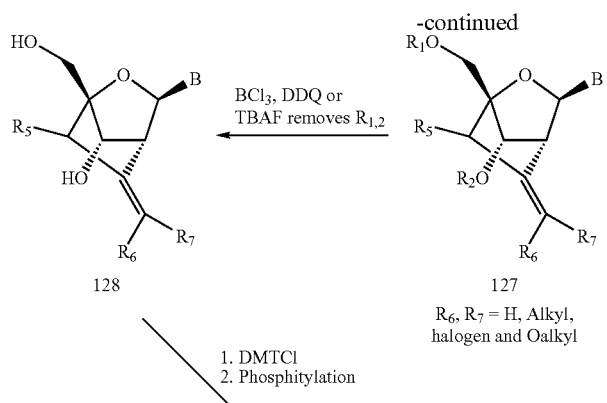
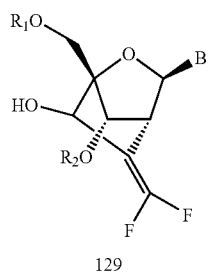
$R_6, R_7$ = H, Alkyl, halogen and Oalkyl
1. DMTCl
2. Phosphitylation
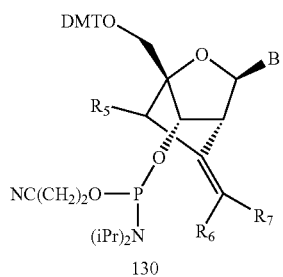
$R_1$ = TBDPS, Nap, Bn or dichloro-Bn
$R_2$ = Nap, Bn or dichloro-Bn
Compounds 122, 104 and 105 are prepared as per the procedures illustrated in examples 19 and 20.
EXAMPLE 23
Preparation of Compound 134 (Scheme 23)
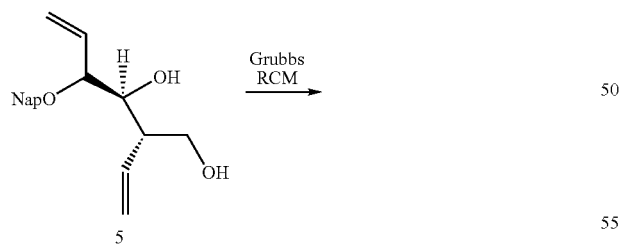
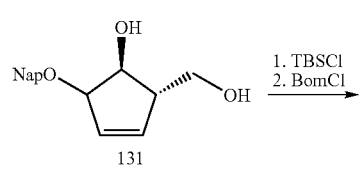
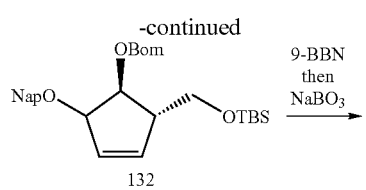
Compound 5 is prepared as per the procedures illustrated in example 1.

EXAMPLE 24
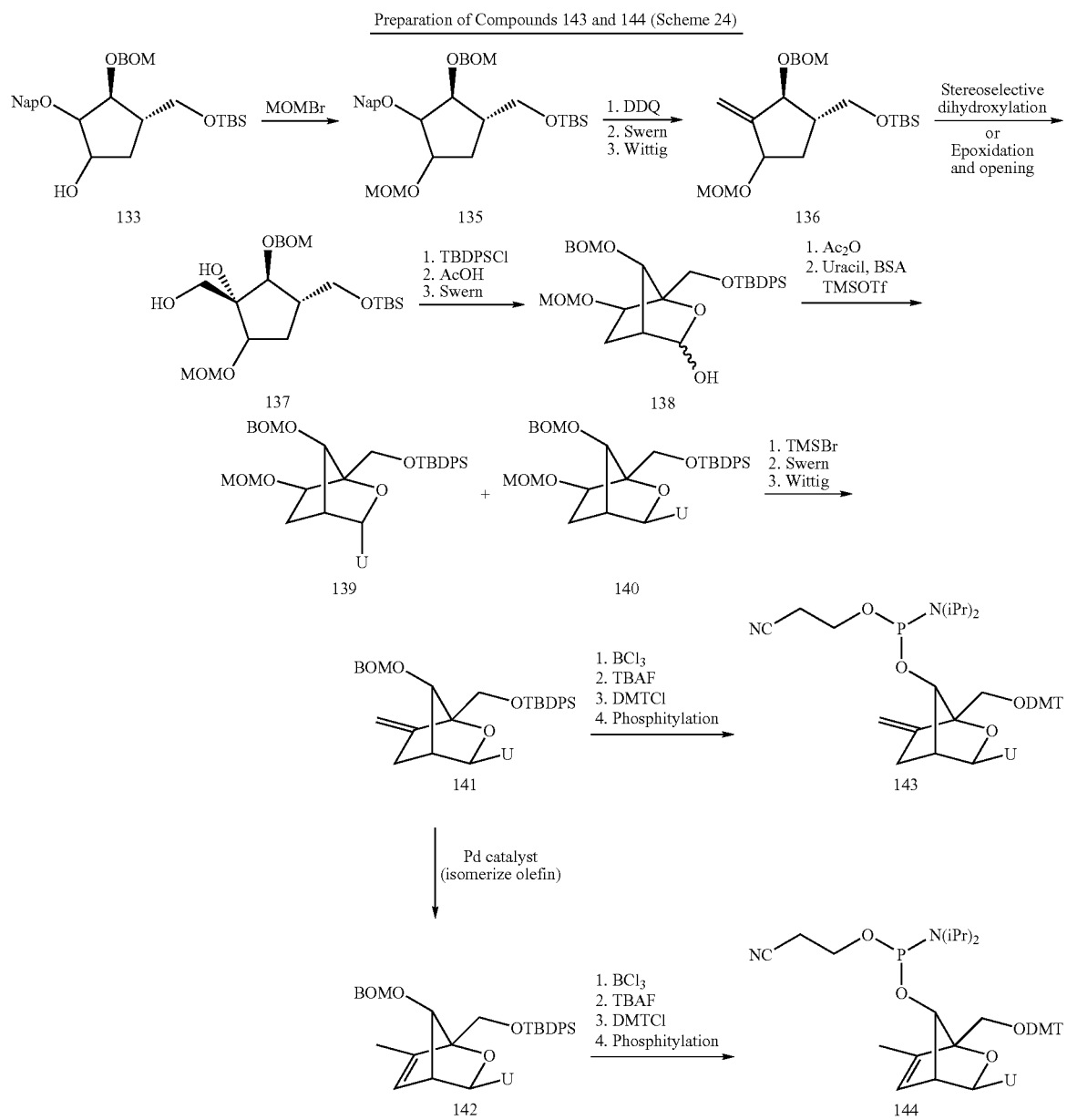
Compound 133 is prepared as per the procedures illustrated in example 23.
EXAMPLE 25
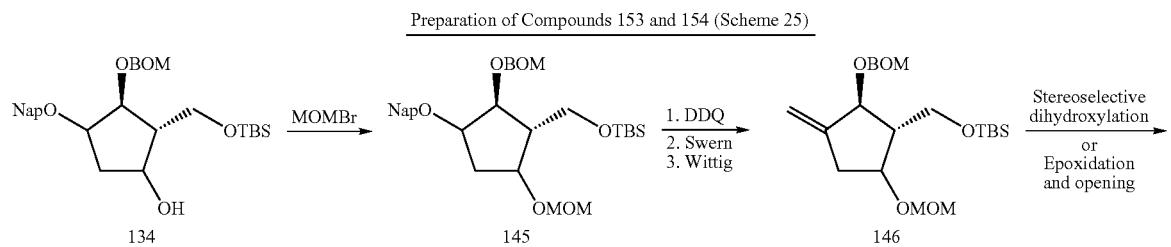

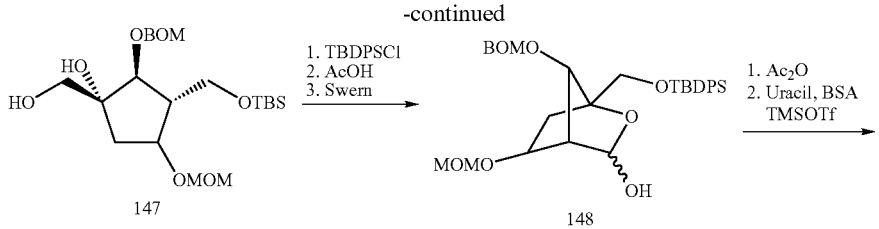
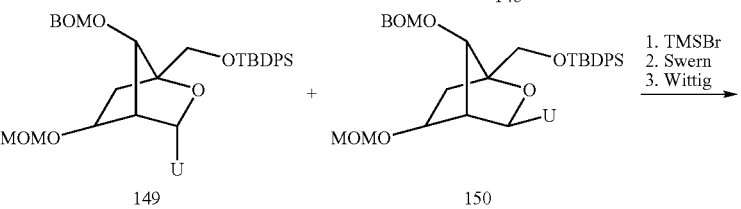
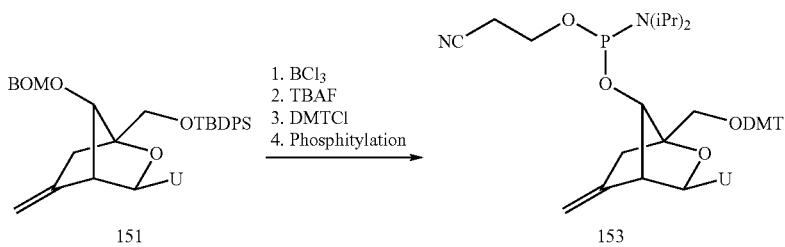
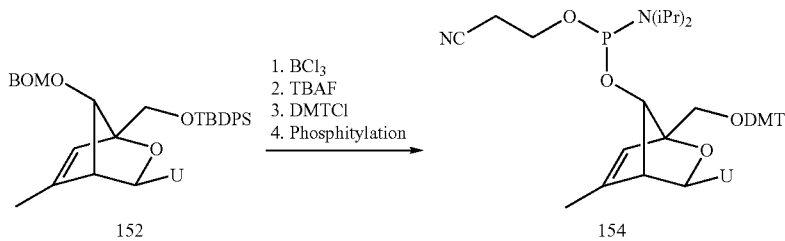
Compound 134 is prepared as per the procedures illustrated in example 23.
EXAMPLE 26
Preparation of Compound 160 (Scheme 26)
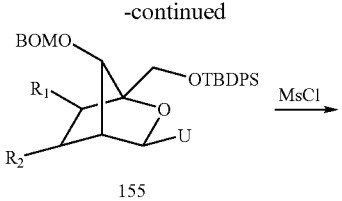
139
R$_1$ = OMOM, R$_2$ = H
or
R$_1$ = H, R$_2$ = OMOM
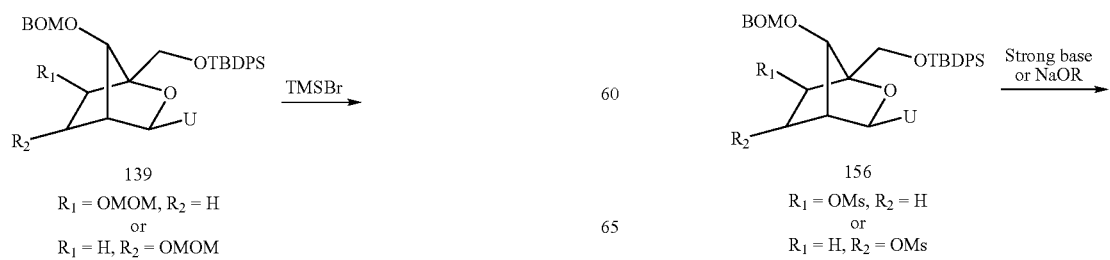
155
R$_1$ = OH, R$_2$ = H
or
R$_1$ = H, R$_2$ = OH
156
R$_1$ = OMs, R$_2$ = H
or
R$_1$ = H, R$_2$ = OMs

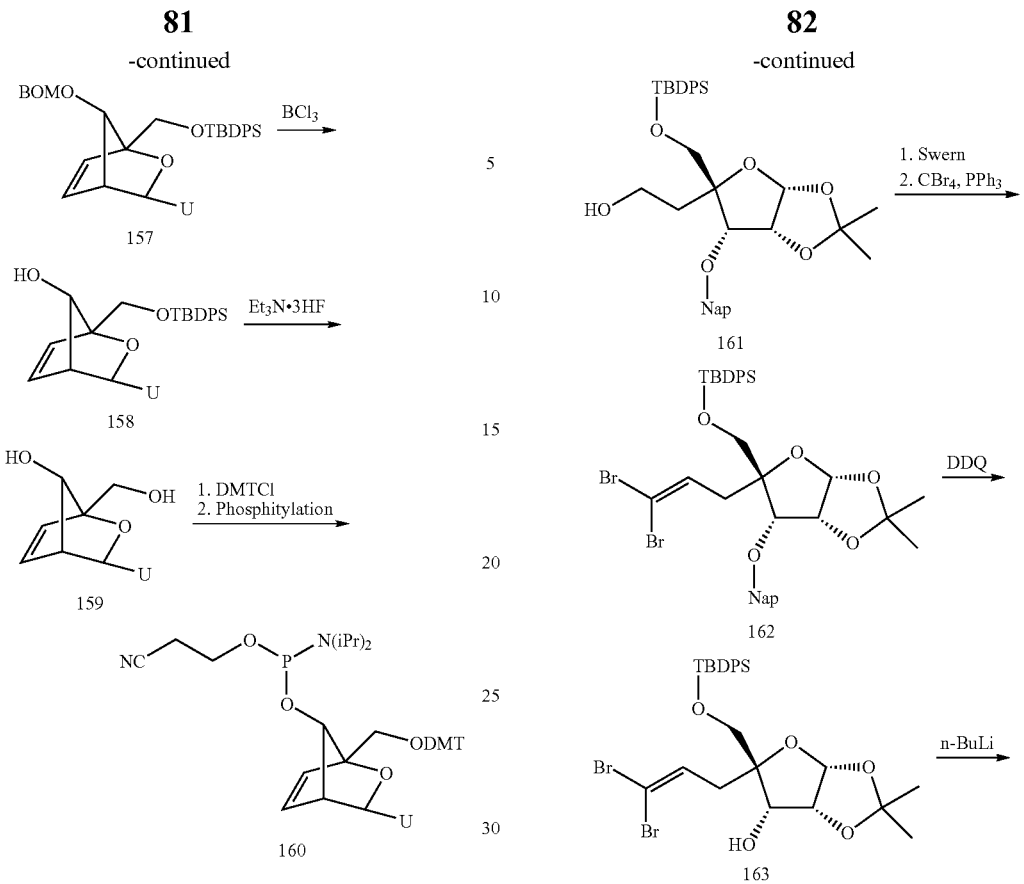
Compound 139 is prepared as per the procedures illustrated in example 24.
EXAMPLE 27
Preparation of (1R,3R,4R,7S)-7-[2-Cyanoethoxy(diisopropylamino)phosphin oxy]-1-(4,4'-dimethoxytrityloxymethyl)-3-(uracil-1-yl)-5-methylene-2-oxa-bicyclo[2.2.1]heptane
(Compound 171, Scheme 27)
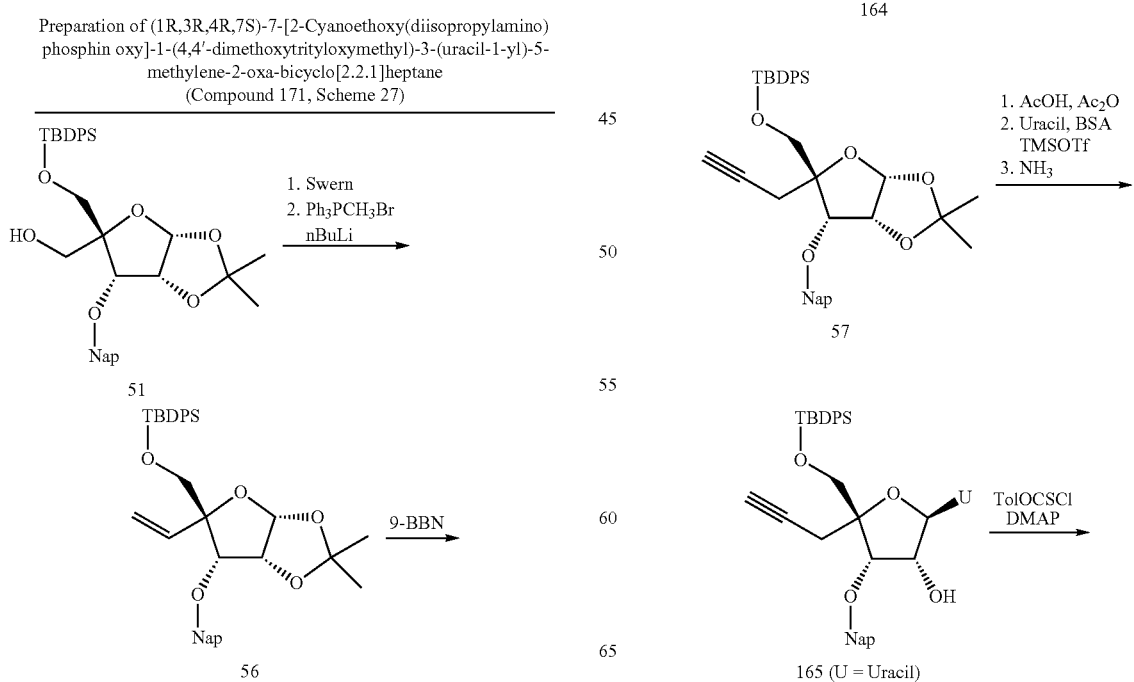

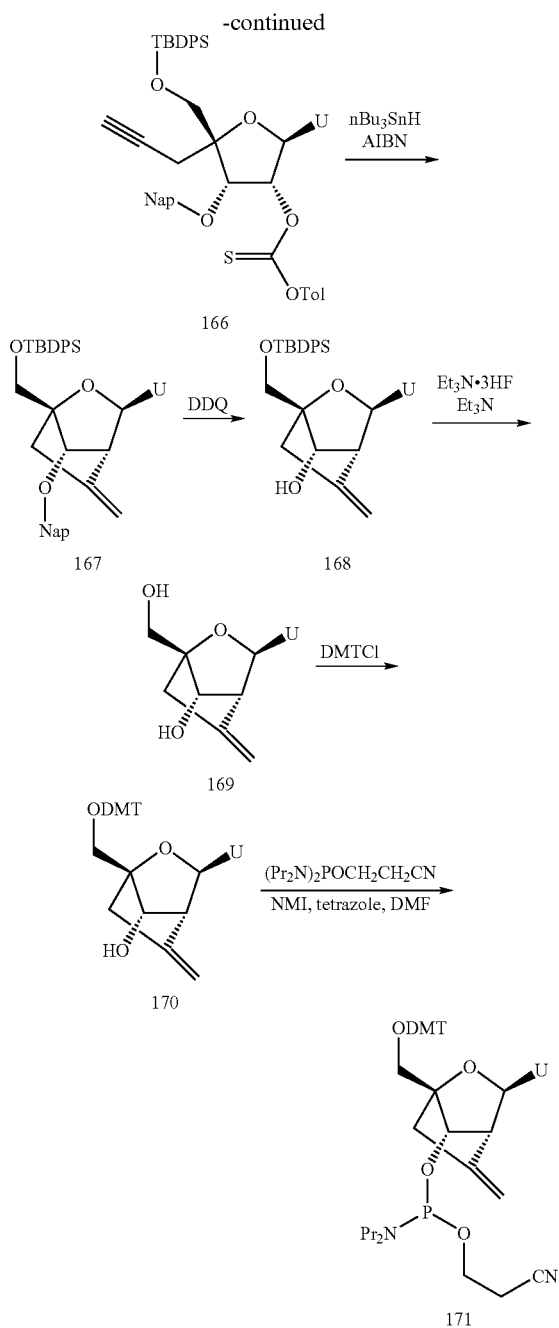

A) Compound 56

Dimethylsulfoxide (188 mmol, 13.3 mL) was added dropwise to a cold (−78° C.) solution of oxalyl chloride (94 mmol, 8.2 mL) in dichloromethane (600 mL). After stirring for 30 minutes, a solution of alcohol 51 (67 mmol, 40.0 g) in dichloromethane (100 mL) was added to the reaction via a canula and stirring was continued for another 45 minutes at −78° C. Triethylamine (281 mmol, 39.0 mL) was added and the reaction was removed from the cold bath and stirring was continued for another 30 minutes. The reaction was then diluted with dichloromethane and washed sequentially with 5% HCl, saturated NaHCO₃, brine, dried (Na₂SO₄) and concentrated to provide the corresponding aldehyde which was used in the next step without any purification.

nBuLi (84 mmol, 33.5 mL of a 2.5 M solution) was added to a cold (0° C.) solution of methyltriphenyphosphonium bromide (84 mmol, 29.9 g) in THF (600 mL). After stirring for 2 hours in the ice bath, the deep red solution was cooled to −78° C. and a solution of the crude aldehyde from above in THF (70 mL) was added to the reaction over 20 minutes. The reaction was allowed to warm to room temperature gradually and stirred for 16 hours. Saturated ammonium chloride was added to the reaction and roughly 80% of the THF was evaporated under reduced pressure. The resulting oil was diluted with ethyl acetate and the organic layer was washed with water, brine, dried (Na₂SO₄) and concentrated. The crude material was purified by chromatography (silica gel, eluting with hexanes/20% ethyl acetate in hexanes) to provide Compound 56 (36.4 g, 92% over two steps) as an oil.

B) Compound 161

A solution of Compound 56 (57.5 mmol, 34.2 g) in THF (40 mL) was added to a solution of 9-BBN (0.5 M in THF, 172 mmol, 345 mL). After stirring at room temperature for 24 hours, the reaction was cooled in an ice bath and carefully quenched with EtOH. A suspension of sodium perborate tetrahydrate (340 mmol, 53.0 g) in ethanol (340 mL) and water (340 mL) was added to the reaction and the mixture was heated at 50° C. for 4 hours. Roughly 80% of the solvent was evaporated under reduced pressure and the residue was suspended in ethyl acetate and washed sequentially with water, brine, dried (Na₂SO₄) and concentrated. The residue was purified by chromatography (silica gel, eluting with 10 to 30% ethyl acetate in hexanes) to provide Compound 161 (27.7 g, 76%) as an oil.

C) Compound 162

Dimethylsulfoxide (68.6 mmol, 4.9 mL) was added dropwise to a cold (−78° C. solution of oxalyl chloride (34.3 mmol, 3.0 mL) in dichloromethane (170 mL). After stirring for 30 minutes, a solution of alcohol, Compound 161 (22.9 mmol, 14.0 g) in dichloromethane (50 mL) was added to the reaction via a canula and stirring was continued for another 45 minutes at −78° C. Triethylamine (102.9 mmol, 14.4 mL) was added and the reaction was removed from the cold bath and stirring was continued for another 30 minutes. The reaction was then diluted with dichloromethane and washed sequentially with 5% HCl, saturated NaHCO₃, brine, dried (Na₂SO₄) and concentrated to provide the corresponding aldehyde which was used in the next step without any purification.

A solution of triphenylphosphine (91.3 mmol, 24.0 g) in dichloromethane (50 mL) was added to a cold (0° C.) solution of carbon tetrabromide (45.6 mmol, 15.0 g) in dichloromethane (200 mL). After stirring for 30 minutes, the reaction was cooled to −78° C. and a solution of the crude aldehyde (57.5 mmol) in dichloromethane (40 mL) was added to the reaction. After stirring at −78° C. for 2 hours, the reaction was quenched with saturated sodium bicarbonate solution and the organic layer was washed with brine, dried (Na₂SO₄) and concentrated. Purification by chromatography (silica gel, eluting with hexanes to 15% ethyl acetate in hexanes) provided olefin, Compound 162 (14.1 g, 81% from 56a).

D) Compound 163

DDQ (31.3 mmol, 7.1 g) was added to a solution of Compound 162 (15.7 mmol, 12.0 g) in dichloromethane (150 mL) and water (7.5 mL). After stirring at room temperature for 6 hours, the reaction was evaporated to dryness under reduced pressure and the residue was redissolved in ethyl acetate. The organic layer was then washed with watsr, 10% sodium bisulfite, saturated sodium bicarbonate, brine, dried (Na₂SO₄) and concentrated. Purification by chromatography (silica gel, 10 to 20% ethyl acetate in hexanes) provided Compound 163 (quantitative).

E) Compound 164 nBuLi (75 mmol, 30 mL of a 2.5 M solution in hexanes) was added to a cold (−78° C.) solution of Compound 163 (15 mmol) in THF (150 mL). After stirring at −78° C. for 30 minutes, the reaction was quenched using saturated ammonium chloride and diluted with ethyl acetate. The organic layer was then sequentially washed with water, brine, dried ($Na_2SO_4$) and concentrated to provide Compound 164 (7.3 g, quantitative).

F) Compound 57

Sodium hydride (18.5 mmol, 0.74 g, 60% in mineral oil) was added in portions to a cold (0° C.) solution of Compound 164 (14.8 mmol, 7.3 g) and 2-bromomethyl-naphthalene (18.5 mmol, 4.1 g) in DMF (100 mL). After stirring for 1 hour, additional sodium hydride (0.35 g) was added to the reaction and the stirring was continued for another 3 hours at room temperature. The reaction was then cooled in an ice bath and carefully quenched with saturated ammonium chloride and then diluted with ethyl acetate. The organic layer was sequentially washed with water, brine, dried ($Na_2SO_4$) and concentrated. Purification by column chromatography (silica gel, eluting with 10 to 15% ethyl acetate in hexanes) provided Compound 57 (7.6 g, 81%).

G) Compound 165

Concentrated sulfuric acid (2 drops) was added to a solution of compound 57 (12.0 mmol, 7.5 g) in acetic acid (36 mL) and acetic anhydride (7 mL). After stirring at room temperature for 15 minutes, the reaction was concentrated under reduced pressure and the residue was diluted with ethyl acetate. The organic layer was washed with water, saturated sodium bicarbonate (until washings are pH>10), brine, dried ($Na_2SO_4$) and concentrated to provide the bis-acetate which was used in the next step without any purification.

N,O-bis-trimethylsilyl-acetamide (60.0 mmol, 14.8 mL) was added to a suspension of uracil (24 mmol, 2.7 g) and compound 58a (12.0 mmol, from above) in acetonitrile (60 mL).

The suspension was heated until dissolution occurred after which it was cooled in an ice bath. TMSOTf (18.0 mmol, 3.3 mL) was added drop-wise to the reaction and the reaction was refluxed for 2 hours. The reaction was then cooled in an ice bath and carefully quenched with saturated sodium bicarbonate solution. The reaction was then diluted with ethyl acetate and the organic layer was washed with water, brine, dried ($Na_2SO_4$) and concentrated to provide the crude nucleoside which was used in the next step without any further purification.

The crude nucleoside (12.0 mmol) obtained from above, was dissolved in a solution of ammonia in methanol (7 N, 36 mL). After stirring for 16 hours at room temperature, the reaction was concentrated under reduced pressure and the residue was purified by chromatography (silica gel, eulting with 35 to 50% ethyl acetate in hexanes) to provide Compound 165 (5.9 g, 72% from 57).

H) Compound 166

Tolyl-chlorothionoformate (1.5 mL, 9.9 mmol) was added drop-side to a cold (0° C.) solution of compound 165 (8.9 mmol, 5.9 g) and dimethylaminopyridine (19.7 mmol, 2.4 g) in acetonitrile (90 mL). After stirring for 1 hour, the reaction was quenched with methanol. Roughly 50% of the solvent was evaporated under reduced pressure and the reaction was diluted with ethyl acetate and washed with 5% HCl, saturated sodium bicarbonate, brine, dried ($Na_2SO_4$) and concentrated. Purification by chromatography (silica gel, eluting with 30 to 40% ethyl acetate in hexanes) provided Compound 166 (6.3 g, 86%).

I) Compound 167

A solution of compound 166 (7.7 mmol, 6.2 g) in toluene (230 mL) was refluxed for 30 minutes. A solution of $nBu_3SnH$ (15.4 mmol, 4.1 mL) in toluene (36 mL) was added drop-wise to the refluxing reaction. After about half (18 mL) of the $nBu_3SnH$ solution was added to the reaction (30 minutes), a solution of AIBN (15.4 mmol, 2.5 g) in toluene (40 mL) was added drop-wise to the reaction over 90 minutes. After refluxing for another 2 hours, the reaction was cooled and the solvent was evaporated under reduced pressure. The residue was diluted with ether and washed with saturated KF solution, brine, dried ($Na_2SO_4$) and concentrated. Purification of the residue by chromatography (silica gel, eluting with 25 to 40% ethyl acetate in hexanes) provided Compound 167 (3.3 g).

J) Compound 168

DDQ (9.3 mmol, 2.1 g) was added to a solution of compound 167 (4.7 mmol, 3.0 g) in dichloromethane (47 mL) and water (2.5 mL). After stirring at room temperature for 6 hours, the reaction was concentrated under reduced pressure and re-dissolved in ethyl acetate. The organic layer was washed with water, 10% sodium bisulfite, saturated sodium bicarbonate, brine, dried ($Na_2SO_4$) and concentrated. Purification of the residue by chromatography (silica gel, eluting with 30 to 60% ethyl acetate in hexanes) provided Compound 168 (1.46 g, 62%).

K) Compound 169

Triethylamine trihydrofluoride (0.94 mL, 5.8 mmol) was added to a solution of compound 168 (2.9 mmol, 1.45 g) in THF (20 mL). After stirring at room temperature for 16 hours, additional triethylamine trihydrofluoride (0.9 mL) was added to the reaction. After stirring for 40 hours, the solvent was evaporated under reduced pressure and the residue was purified by chromatography (silica gel, eluting with 5 to 10% methanol in chloroform) provided the nucleoside, Compound 169 (0.53 g, 69%). $^1H$ NMR (300 MHz, MeOD) δ=8.08-7.88 (m, 1 H), 5.67-5.47 (m, 1 H), 5.38-5.25 (m, 1 H), 5.25-5.15 (m, 1 H), 5.06-4.93 (m, 1 H), 4.13-3.94 (m, 1 H), 3.88-3.67 (m, 2 H), 3.30-3.15 (m, 2 H), 3.10-2.95 (m, 1H), 2.52-2.30 (m, 1 H), 2.16 (none, 1 H)

L) Compound 170

Dimethoxytrityl chloride (3.0 mmol, 1.0 g) was added to a solution of compound 169 (2.5 mmol, 0.67 g) in pyridine (10 mL). After stirring at room temperature for 16 hours, the reaction was quenched with methanol and the pyridine was removed under reduced pressure. The residual oil was dissolved in ethyl acetate and the organic layer was washed with saturated sodium bicarbonate, brine, dried ($Na_2SO_4$) and concentrated. Purification by chromatography (silica gel, eluting with 70% ethyl acetate in hexanes containing 1% triethylamine) provided compound 170 (1.36 g).

M) Compound 171

$(iPr_2N)_2POCH_2CH_2CN$ (1.7 mmol, 0.53 mL) was added to a solution of Compound 170 (1.1 mmol, 0.63 g), NMI (0.28 mmol, 0.022 g) and tetrazole (0.88 mmol, 0.062 g) in DMF (3.0 mL). After stirring at room temperature for 6 hours, the reaction was diluted with ethyl acetate and washed with saturated sodium bicarbonate, brine, dried ($Na_2SO_4$) and concentrated. Purification by chromatography (silica gel, eluting with 50 to 60% ethyl acetate in hexanes) provided Compound 171 (0.79 g). $^{31}P$ NMR (300 MHz, $CDCl_3$) δ=149.2, 148.6.

EXAMPLE 28

Preparation of (1R,3R,4R,7S)-7-[2-Cyanoethoxy(diisopropylamino)phosphin oxy]-1-(4,4'-dimethoxytrityloxymethyl)-3-(cytosin-1-yl)-5-methylene-2-oxa-bicyclo[2.2.1]heptane (Compound 175, Scheme 28)

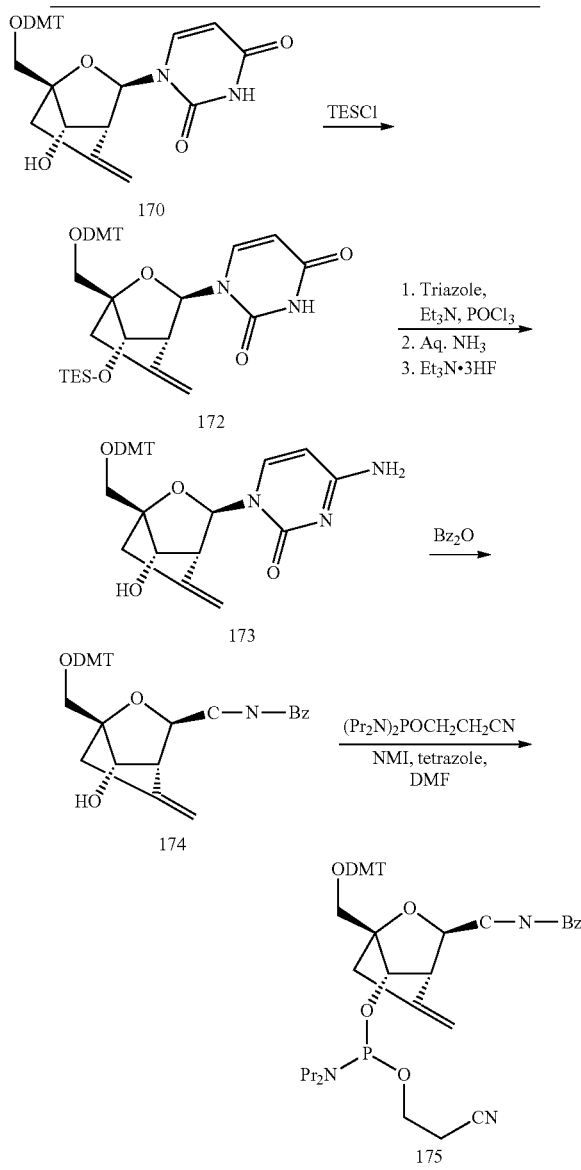

A) Compound 172

Triethylsilyl chloride (2.7 mmol, 0.29 mL) was added to a solution of Compound 170 (0.05 mmol, 0.3 g) and imidazole (3.4 mmol, 0.23 g) in DMF (1 mL). After stirring at room temperature for 16 hours, the reaction was diluted with ethyl acetate and the organic layer was washed with water, brine, dried (Na$_2$SO$_4$) and concentrated. Purification by chromatography (silica gel, eluting with 40% ethyl acetate in hexanes) provided Compound 172 (0.23 g).

B) Compound 173

Phosphorus oxychloride (2.7 mmol, 0.25 mL) was added to a cold suspension of 1,2,4-triazole (11.5 mmol, 0.8 g) in acetonitrile (10 mL). After stirring for 15 minutes, triethylamine (13.5 mmol, 1.9 mL) was added to the reaction and the white suspension was stirred for another 30 minutes. A solution of compound 172 (0.34 mmol, 0.23 g) in acetonitrile (5 mL) was added to the reaction and the stirring was continued at room temperature for 5 hours. The reaction was then concentrated under reduced pressure and the residue was dissolved in ethyl acetate and the organic layer was washed with water, brine, dried (Na$_2$SO$_4$) and concentrated and the crude material was used in the next step without any purification.

Aqueous ammonia (0.2 mL) was added to a solution of the crude material obtained above in dioxane (5 mL). After stirring at room temperature for 4 hours, the reaction was evaporated to dryness and the residue was dried to provide the cytosine nucleoside.

Triethylamine trihydrofluoride (1.7 mmol, 0.27 mL) was added to a solution of compound from above and triethylamine (0.84 mmol, 0.12 mL) in THF (3 mL). After stirring at room temperature for 16 hours the reaction was then diluted with ethyl acetate and the organic layer was washed with water, saturated sodium bicarbonate, brine, dried (Na$_2$SO$_4$) and concentrated. Purification by chromatography (silica gel, eluting with 10% methanol in dichloromethane) provided Compound 173.

C) Compound 174

Benzoic anhydride (1.7 mmol, 0.37 g) was added to a solution of the cytosine nucleoside (0.82 mmol, 0.47 g) in DMF (1.6 mL). After stirring at room temperature for 24 hours, the reaction was diluted with ethyl acetate and the organic layer was washed with water, brine, dried (Na$_2$SO$_4$) and concentrated. Purification by chromatography (silica gel, eluting with 3% methanol in dichloromethane) provided Compound 174 (0.54 g).

D) Compound 175

(iPr$_2$N)$_2$POCH$_2$CH$_2$CN (1.2 mmol, 0.38 mL) was added to a solution of Compound 174 (0.86 mmol, 0.54 g), NMI (0.21 mmol, 0.016 g) and tetrazole (0.64 mmol, 0.045 g) in DMF (2 mL). After stirring at room temperature for 6 hours, the reaction was diluted with ethyl acetate and washed with saturated sodium bicarbonate, brine, dried (Na$_2$SO$_4$) and concentrated. Purification by chromatography (silica gel, eluting with 70 to 80% ethyl acetate in hexanes) provided Compound 175 (0.25 g). $^{31}$P NMR (300 MHz, CDCl$_3$) δ=149.2, 148.8.

EXAMPLE 29

Preparation of (1R,3R,4R,7S)-7-[2-Cyanoethoxy(diisopropylamino)phosphin oxy]-1-(4,4'-dimethoxytrityloxymethyl)-3-(adenin-7-yl)-5-methylene-2-oxa-bicyclo[2.2.1]heptane (Compound 179, Scheme 29)

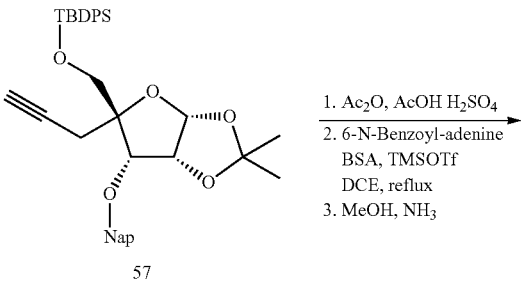

-continued

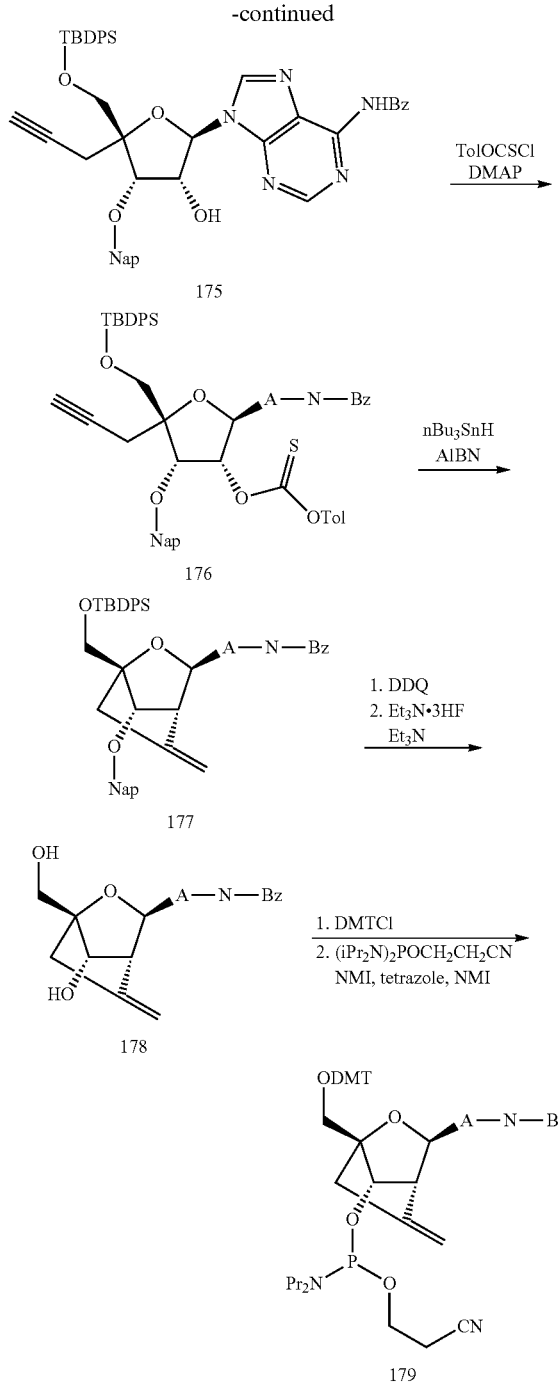

ether followed by a phosphitilation reaction provides the phosphoramidite, Compound 179.

EXAMPLE 30

Preparation of (1R,3R,4R,7S)-7-[2-Cyanoethoxy(diisopropylamino)phosphin oxy]-1-(4,4'-dimethoxytrityloxymethyl)-3-(guanin-7-yl)-5-methylene-2-oxa-bicyclo[2.2.1]heptane (Compound 186, Scheme 30)

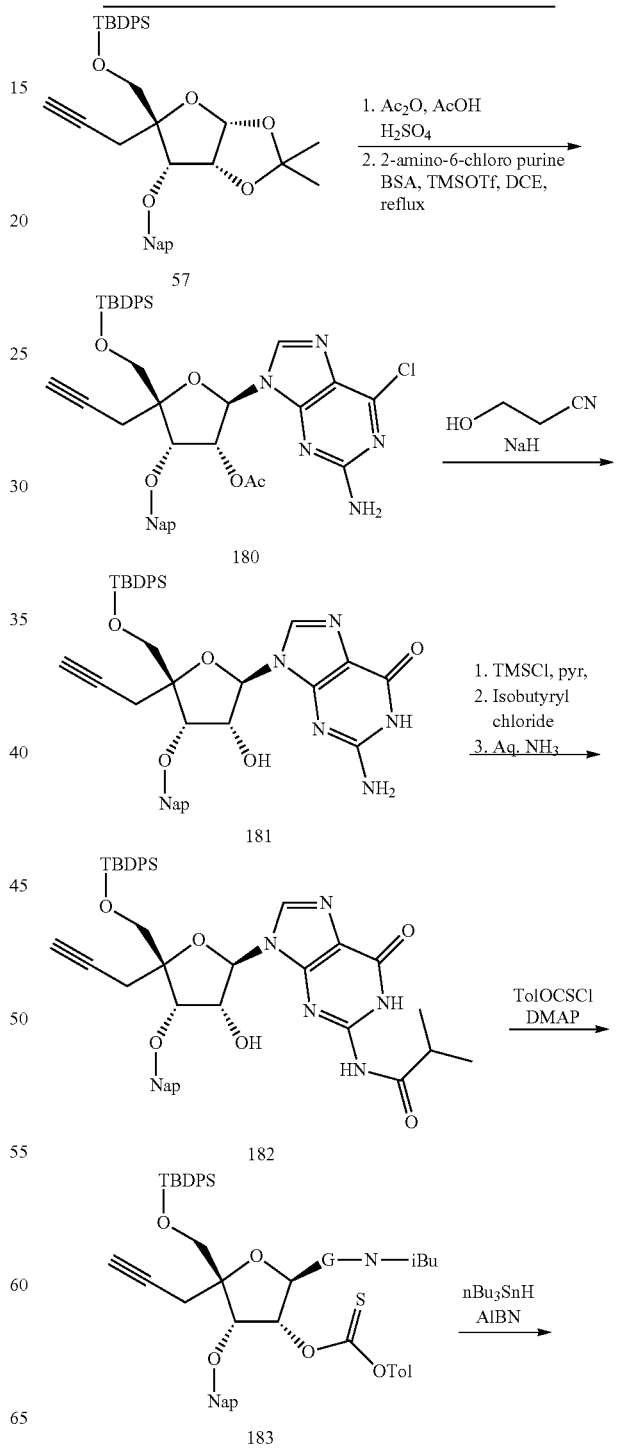

Compound 179 is prepared from Compound 57 using the general procedures described in Example 27. Acetolysis of the 1,2-acetonide followed by a Vorbrugen reaction with 6-N-benzoyl-adenine in refluxing dichloroethane and removal of the 2'O-acetyl protecting group provides the desired nucleoside, Compound 175. Reaction of the 2'-hydroxyl group with a thionoformate reagent followed by a radical cyclization provides the nucleoside, Compound 177. Removal of the Naphthyl and TBDPS protecting groups using DDQ and triethylamine trihydrofluoride provides the nucleoside, Compound 178. Protection of the 5'-hydroxyl group as the DMT

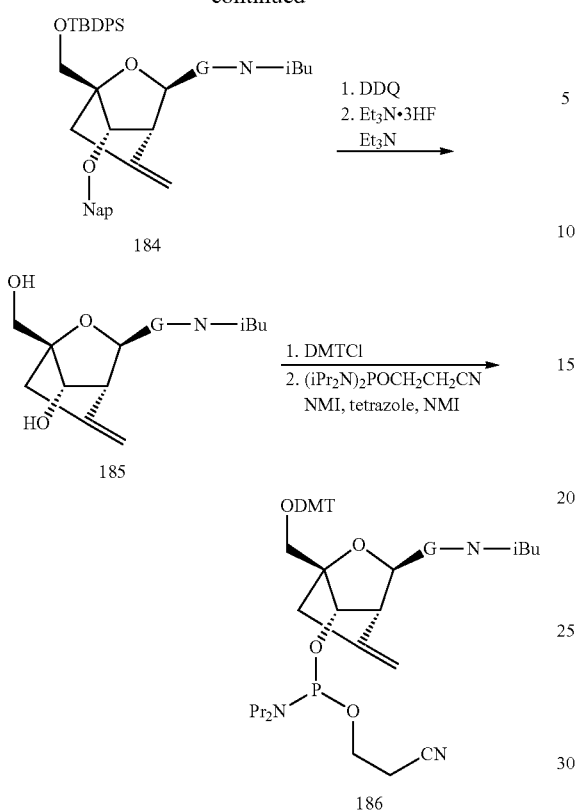
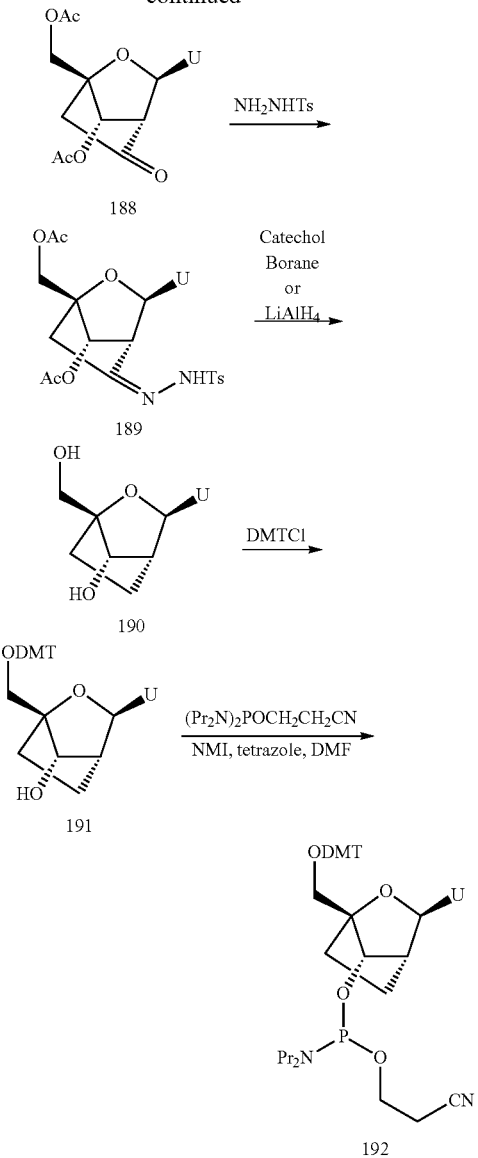

Compound 186 is prepared from Compound 57 using the general procedures described in example 27. Acetolysis of the 1,2-acetonide followed by a Vorbrugen reaction with 2-amino-6-chloro-purine provides nucleoside, Compound 180. Reaction of 180 with 3-hydroxypropionitrile and sodium hydride provides the deprotected nucleoside 181. Reaction of the 2'-hydroxyl group with a thionoformate reagent followed by a radical cyclization provides nucleoside 184. Removal of the Naphthyl and TBDPS protecting groups using DDQ and triethylamine trihydrofluoride provides nucleoside185. Protection of the 5'-hydroxyl group as the DMT ether followed by a phosphitylation reaction provides the phosphoramidite, Compound186.

EXAMPLE 31

Preparation of (1R,3R,4R,7S)-7-[2-Cyanoethoxy(diisopropylamino)phosphin oxy]-1-(4,4'-dimethoxytrityloxymethyl)-3-(uracil-1-yl)-2-oxa-bicyclo[2.2.1]heptane (Compound 192, Scheme 31)

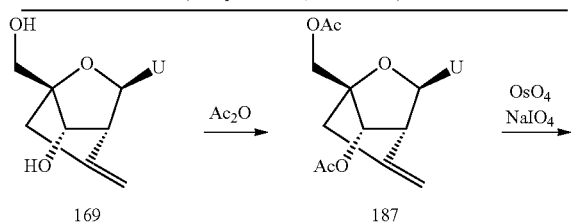

A) Compound 187

Acetic anhydride (7.8 mmol, 0.73 mL) was added to a solution of Compound 169 (1.9 mmol, 0.51 g, example 27) in pyridine (4 mL). After stirring at room temperature for 20 hours, the solvent was removed and ethyl acetate (few drops) was added to the oil. The white solid that was formed was collected and dried to provide Compound 187 (0.6 g, 90%).

B) Compound 188

Osmium tetroxide (0.08 mL oa 2.5% w/w solution in iPrOH) was added to a solution of Compound 187 (0.04 g) and sodium periodate (0.12 g) in dioxane (0.8 mL) and water (2 mL). After stirring at room temperature for 2 days, the reaction was diluted with ethyl acetate and washed with sodium thiosulfate solution, brine, dried ($Na_2SO_4$) and concentrated. Purification by chromatography (silica gel, eluting with 25% acetone in chloroform) provided Compound 188 (10 mg) and unreacted 187 (20 mg). $^1$H NMR (300 MHz, CHLOROFORM-d) δ=8.82 (br. s., 1 H), 7.77 (d, J=8.1 Hz, 1 H), 5.82 (br. s., 2 H), 5.73 (br. s., 1 H), 5.44-5.25 (m, 1 H), 4.64-4.34 (m, 2 H), 3.88-3.66 (m, 1 H), 3.65-3.39 (m, 3 H), 2.18 (br. s., 3 H), 2.09 (br. s., 3 H).

93

C) Compound 189

Tosylhydrazine (0.034 mmol, 6 mg) was added to a suspension of Compound 188 (10 mg) and anhydrous $Na_2SO_4$ in methanol (0.3 mL). After refluxing for 4 hours, the reaction was cooled to room temperature. LCMA analysis of the crude reaction mixture indicated complete conversion to Compound 189. LCMS: retention time (2.7 minutes), M+H expected 521.1; observed 521.0.

D) Compound 192

Reduction of tosylhydrazone, Compound 189 to Compound 190 is accomplished by a variety of reducing agents such as lithium aluminum hydride, catechol borane or sodium cyano borohydride reported in the art. Conversion of 190 to the phsophoramidite, Compound 192 is accomplished according to the general procedure described in example 27 for conversion of Compound 169 to Compound 171.

EXAMPLE 32

Preparation of (1R,3R,4R,5R7S)-7-[2-Cyanoethoxy(diisopropylamino)phosphin oxy]-1-(4,4'-dimethoxytrityloxymethyl)-3-(uracil-1-yl)-5-fluoro-2-oxa-bicyclo[2.2.1]heptane (Compound 200, Scheme 31)

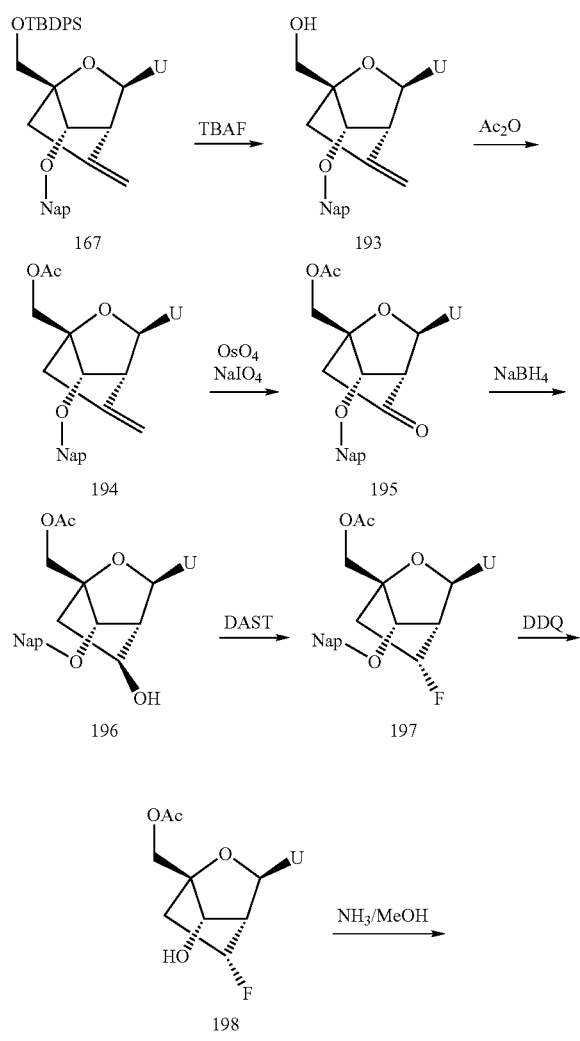

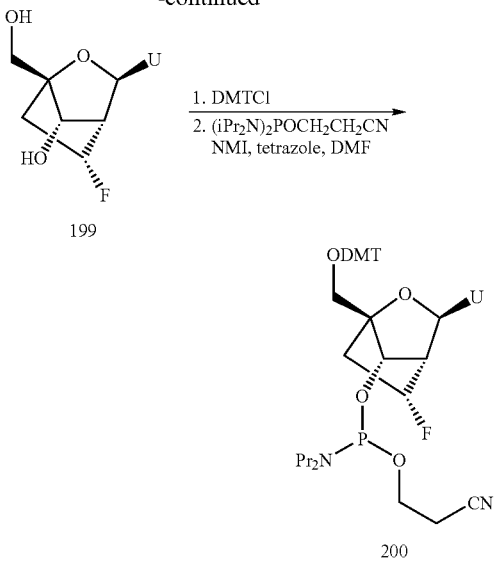

A) Compound 193

TBAF (93 mmol, 93 mL of a 1M solution in THF) was added to a solution of Compound 167 (46.6 mmol, 30.0 g) in THF (50 mL). After stirring at room temperature for 16 hours, the solvent was evaporated under reduced pressure and the resulting oil was dissolved in ethyl acetate. The organic layer was washed with water, brine, dried ($Na_2SO_4$) and concentrated. Purification by column chromatography (silica gel, eluting with 20 to 40% acetone in chloroform) provided Compound 193 (12.0 g, 63%).

B) Compound 194

Acetic anhydride (88.7 mmol, 8.4 mL) was added to a solution of Compound 193 (29.6 mmol, 12.0 g) in pyridine (100 mL). After stirring at room temperature for 16 hours, the reaction was quenched with methanol and the pyridine was evaporated under reduced pressure. The residue was dissolved in ethyl acetate and the organic layer was washed with water, brine, dried ($Na_2SO_4$) and concentrated. Purification by column chromatography (silica gel eluting with 15 to 20% acetone in chloroform) provided Compound 194 (13.7 g, quantitative).

C) Compound 196

Osmium tetroxide (3 mL of a 2.5% w/w solution in isopropanol) was added to a solution of Compound 194 (14.5 mmol, 6.5 g) and sodium periodate (58.8 mmol, 12.4 mmol) in dioxane (145 mL) and water (145 mL). After stirring at room temperature for 16 hours, the reaction was concentrated under reduced pressure (~30% of original volume) and the residue was partitioned between ethyl acetate and water. The organic layer was washed with saturated sodium thiosulfate solution, brine, dried ($Na_2SO_4$) and concentrated to provide a mixture of crude 195 and unreacted 194 which was used without any further purification.

Sodium borohydride (2 g) was added to a cold (-78° C.) solution of the crude residue above in methanol (50 mL). After stirring for 1 hour, the reaction was quenched by addition of 10% HCl. Ethyl acetate was added and the organic layer was washed with water, brine, dried ($Na_2SO_4$) and concentrated. Purification by column chromatography (silica gel, eluting with 20 to 40% acetone in chloroform) provided Compound 196 (1.45 g) and unreacted 188 (1.17 g).

D) Compound 199

DAST (12.4 mmol, 1.61 mL) was slowly added to a cold (0° C.) solution of Compound 196 (3.1 mmol, 1.4 g) in dichloromethane (30 mL). The reaction was allowed to warm to room temperature gradually and stirred for 16 hours after which it was carefully quenched by addition of saturated sodium bicarbonate. The organic layer was separated and E) Compound 200

Conversion of Compound 199 to the phsophoramidite, Compound 200 is accomplished according to the general procedure described in example 27 for conversion of Compound 169 to Compound 171.

EXAMPLE 33

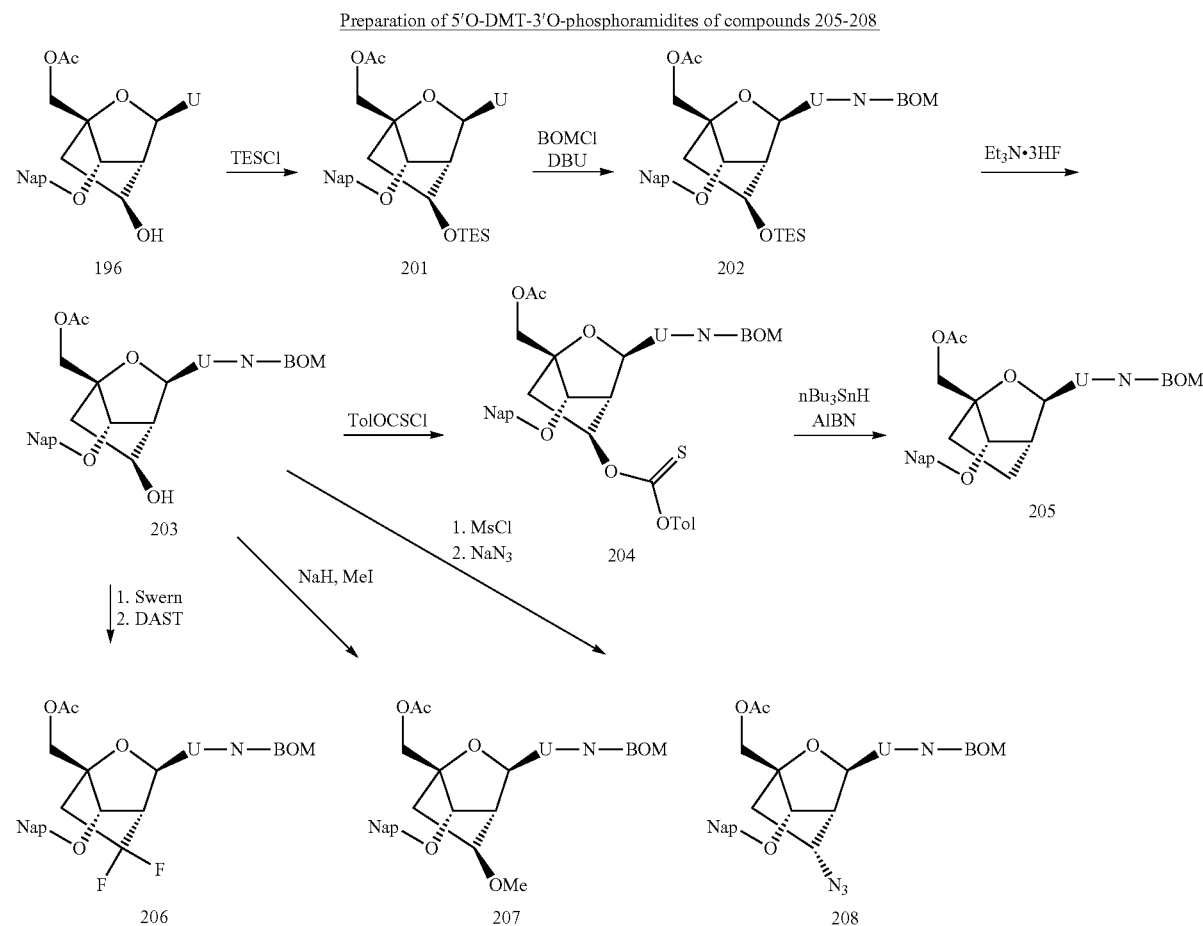

Preparation of 5′O-DMT-3′O-phosphoramidites of compounds 205-208 further washed with water, brine, dried (Na$_2$SO$_4$) and concentrated. Purification by column chromatography (silica gel, eluting with 20% acetone in chloroform) provided Compound 197 (170 mg, impure).

DDQ (0.37 mmol, 81 mg) was added to a solution of Compound 197 (0.17 g from above) in dichloromethane (3.7 mL) and water (0.2 mL). After stirring for 4 hours, additional DDQ (81 mg) was added to the reaction. After stirring at room temperature for 16 hours, the solvent was removed under reduced pressure and the residue was purified by column chromatography (50% acetone in chloroform) to provide Compound 198 (50 mg).

Methanolic ammonia (7N, 1 mL) was added to Compound 198 (50 mg) obtained above. After stirring at room temperature for 3 hours, the solvent was evaporated to provide Compound 199. $^1$H NMR (300 MHz, MeOD) δ=7.92-7.77 (m, 1 H), 5.64 (s, 1 H), 5.45 (d, J=8.1 Hz, 1 H), 5.43-5.15 (m, 1 H), 3.99 (br. s., 1 H), 3.69-3.57 (m, 1 H), 3.57-3.42 (m, 1 H), 3.08 (s, 2 H), 2.73 (d, J=4.0 Hz, 1 H), 2.21-1.99 (m, 1 H), 1.78 (s, 1 H), 1.60-1.33 (m, 1 H). $^{19}$F NMR δ=−202.4 to −202.7 (m)

A) Compound 201

Chloro triethylsilane (1.1 mmol, 0.18 mL) was added to a solution of Compound 196 (0.55 mmol, 0.2 g) and imidazole (2.2 mmol, 0.15 g) in DMF (3 mL). After stirring at room temperature for 2 hours, the reaction was diluted with ethyl acetate and the organic layer was washed with water, brine, dried (Na$_2$SO$_4$) and concentrated. Purification by chromatography (silica gel, eluting with 30 to 50% ethyl acetate in hexanes) provided Compound 201 (0.14 g).

B) Compound 202

Benzyloxymethyl chloride (0.5 mmol, 0.08 mL) was added to a cold (0° C.) solution of Compound 201 (0.25 mmol, 0.14 g) and DBU (0.5 mmol, 0.08 mL) in acetonitrile (1 mL). After stirring at room temperature for 16 hours, the reaction was purified by chromatography (silica gel, eluting with 20 to 30% ethyl acetate in hexanes) provided Compound 202 (75 mg).

C) Compound 203

Triethylamine trihydrofluoride (0.65 mmol, 0.1 mL) was added to a solution of Compound 202 (0.109 mmol, 75 mg) in THF (1 mL). After stirring for 3 hours, the reaction was concentrated and purified by chromatography (silica gel, eluting with 30 to 50% ethyl acetate in hexanes) to provide Compound 203 (61 mg, 99%).

D) Compound 205

Tolyl chlorothionoformate (0.066 mmol, 0.012 g) was added to a solution of Compound 203 (0.043 mmol, 0.025 g) and DMAP (8 mg) in dichloromethane (0.2 mL). After 16 hours at room temperature DIPEA (0.02 mL) was added to the reaction. LCMS: retention time (4.5 minutes), M+H expected 723.2; observed 723.2.

Compound 205 is prepared from Compound 204 by heating with nBu₃SnH in a suitable solvent such as toluene and a radical initiator such as AIBN.

E) Compound 206

Compound 206 is prepared from Compound 205 by oxidation of the primary alcohol under Swern or any other appropriate conditions to provide the corresponding ketone. Reaction of the ketone with a suitable fluorinating agent such as DAST provides Compound 206.

F) Compound 207

Compound 207 is prepared from Compound 205 by reaction with methyl iodide in the presence of a base such as sodium hydride using DMF as the solvent.

G) Compound 208

Compound 208 is prepared from Compound 205 by converting the hydroxyl group to a mesylate or triflate derivative followed by reaction with sodium azide in a solvent such as DMF.

Compounds 205-208 are converted to their 5'O-DMT-3'O-phosphoramidites by removal of the N-BOM group under hydrogenation, strong acid or BCl₃ conditions followed by removal of the 3'O-Nap group with DDQ and removal of the 5'-O-acetyl group as described in example 32. Reaction with DMTCl followed by reaction with an appropriate phosphitilating reagent provides the desired 5'-O-DMT-3'O-phosphoramidites as described in example 27.

EXAMPLE 34

Preparation of (1R,3R,4R,5R,7S)-7-[2-Cyanoethoxy(diisopropylamino)phosphin oxy]-1-(4,4'-dimethoxytrityloxymethyl)-3-(uracil-1-yl)-5-methyl-2-oxa-bicyclo[2.2.1]heptane (Compound 217, Scheme 34) and (1R,3R,4R,5S,7S)-7-[2-Cyanoethoxy(diisopropylamino)phosphin oxy]-1-(4,4'-dimethoxytrityloxymethyl)-3-(uracil-1-yl)-5-methyl-2-oxa-bicyclo[2.2.1]heptane (Compound 218, Scheme 34)

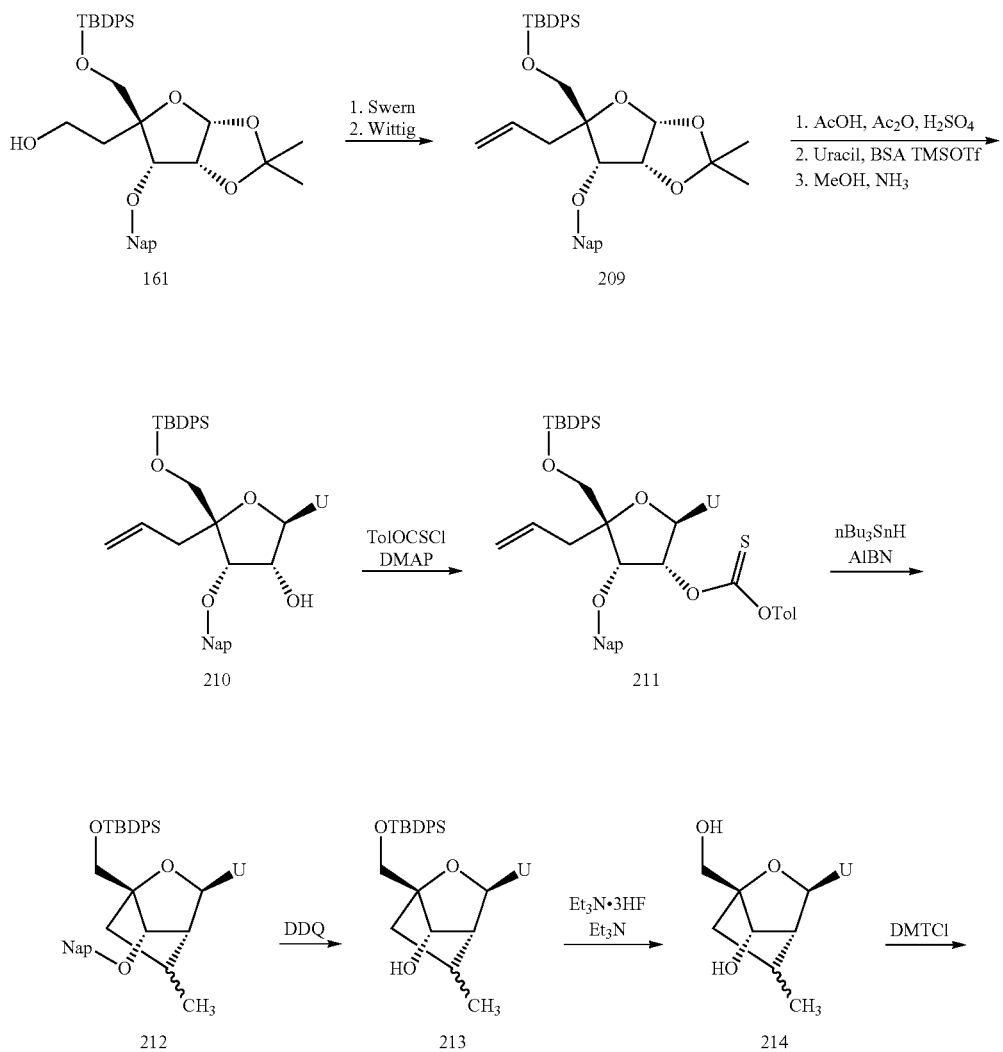

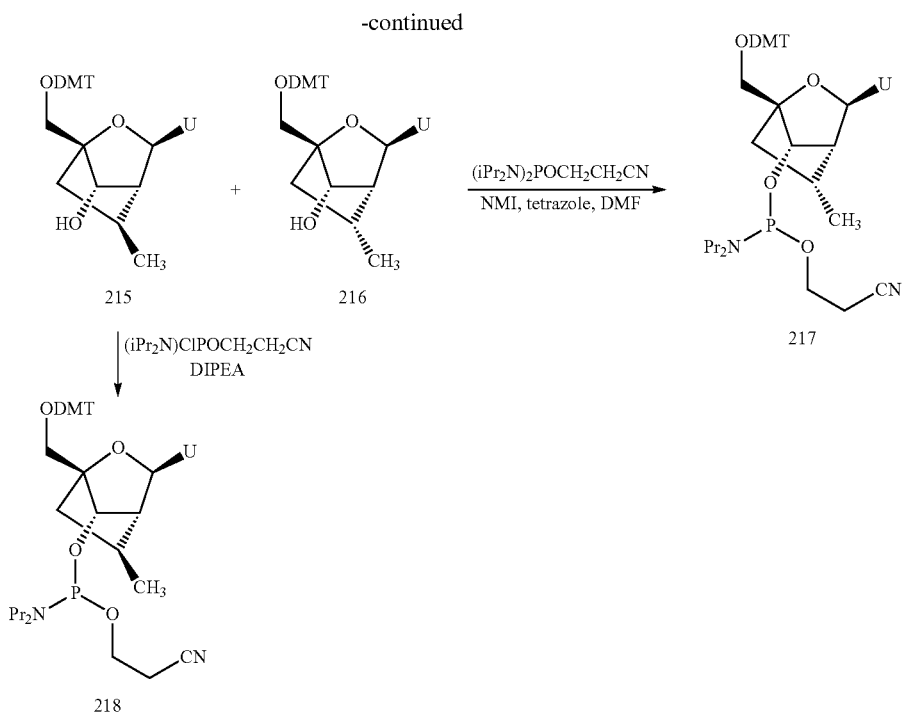

A) Compound 209

Dimethylsulfoxide (63.7 mmol, 4.5 mL) was added to a cold (−78° C.) solution of oxalyl chloride (31.9 mmol, 2.8 mL) in dichloromethane (150 mL). After stirring for 30 minutes, a solution of alcohol, Compound 161 (21.2 mmol, 13.0 g) in dichloromethane (50 mL) was added to the reaction and the stirring was continued for another 45 minutes. Triethylamine (95.6 mmol, 13.4 mL) was added to the reaction which was gradually allowed to warm outside the cold bath for 10 minutes. The reaction was then diluted with chloroform and sequentially washed with 5% HCl, saturated sodium bicarbonate, brine, dired ($Na_2SO_4$) and concentrated to provide the corresponding aldehyde which was used without any further purification.

nBuLi (42.5 mmol, 17 mL of a 2.5 M solution in hexanes) was added to a cold (0° C.) suspension of methyl triphenylphosphoniumbromide (42.5 mmol, 15.2 g) in THF (175 mL). After stirring for 2 hours, the reaction was cooled to −78° C. and a solution of the aldehyde (21.2 mmol) from above in THF (25 mL) was added to the reaction which was gradually allowed to warm to room temperature and stirred for another 16 hours. The reaction was quenched with saturated ammonium chloride and the solvent was removed under reduced pressure. The residue was dissolved in ethyl acetate and the organic layer was washed with water, brine, dried ($Na_2SO_4$) and concentrated. Purification by chromatography (silica gel, eluting with hexanes to 15% ethyl acetate in hexanes) provided Compound 209.

B) Compound 210

Concentrated sulfuric acid (8 drops) was added to a solution of Compound 209 (13.2 mmol, 8.1 g) in acetic acid (40 mL) and acetic anhydride (8 mL). After stirring at room temperature for 15 minutes, the reaction was concentrated under reduced pressure and the residue was diluted with ethyl acetate. The organic layer was washed with water, saturated sodium bicarbonate (until washings are pH>10), brine, dried ($Na_2SO_4$) and concentrated to provide the bis-acetate which was used in the next step without any purification.

N,O-bis-trimethylsilyl-acetamide (29.6 mmol, 7.3 mL) was added to a suspension of uracil (11.8 mmol, 1.3 g) and bis-acetate (13.3 mmol, from above) in acetonitrile (67 mL). The suspension was heated until dissolution occurred after which it was cooled in an ice bath. TMSOTf (17.7 mmol, 3.2 mL) was added drop-wise to the reaction and the reaction was refluxed for 2 hours. The reaction was then cooled in an ice bath and carefully quenched with saturated sodium bicarbonate solution. The reaction was then diluted with ethyl acetate and the organic layer was washed with water, brine, dried ($Na_2SO_4$) and concentrated to provide the crude nucleoside which was used in the next step without any further purification.

The crude nucleoside (13.2 mmol) obtained from above, was dissolved in a solution of ammonia in methanol (7 N, 40 mL). After stirring for 16 hours at room temperature, the reaction was concentrated under reduced pressure and the residue was purified by chromatography (silica gel, eulting with 35 to 50% ethyl acetate in hexanes) to provide Compound 210 (5.0 g).

C) Compound 211

Tolyl-chlorothionoformate (8.3 mmol, 1.3 mL) was added drop-side to a cold (0° C.) solution of Compound 210 (7.6 mmol, 5.0 g) and dimethylaminopyridine (16.6 mmol, 2.0 g) in acetonitrile (75 mL). After stirring for 1 hour, the reaction was quenched with methanol. Roughly 50% of the solvent was evaporated under reduced pressure and the reaction was diluted with ethyl acetate and washed with 5% HCl, saturated sodium bicarbonate, brine, dried ($Na_2SO_4$) and concentrated. Purification by chromatography (silica gel, eluting with 30 to 40% ethyl acetate in hexanes) provided Compound 211 (5.1 g)

I) Compound 212

A solution of Compound 211 (6.3 mmol, 5.1 g) in toluene (190 mL) was refluxed for 30 minutes. A solution of $nBu_3SnH$ (12.5 mmol, 3.3 mL) in toluene (30 mL) was added drop-wise to the refluxing reaction. After about half (15 mL) of the nBu$_3$SnH solution was added to the reaction (30 minutes), a solution of AIBN (12.5 mmol, 2.0 g) in toluene (30 mL) was added drop-wise to the reaction over 90 minutes. After refluxing for another 2 hours, the reaction was cooled and the solvent was evaporated under reduced pressure. The residue was diluted with ether and washed with saturated KF solution, brine, dried (Na$_2$SO$_4$) and concentrated. Purification of the residue by chromatography (silica gel, eluting with 20 to 40% ethyl acetate in hexanes) provided Compound 212 (3.2 g).

E) Compound 213

DDQ (9.9 mmol, 2.3 g) was added to a solution of Compound 212 (4.9 mmol, 3.2 g) in dichloromethane (50 mL) and water (2.5 mL). After stirring at room temperature for 6 hours, the reaction was concentrated under reduced pressure and re-dissolved in ethyl acetate. The organic layer was washed with water, 10% sodium bisulfite, saturated sodium bicarbonate, brine, dried (Na$_2$SO$_4$) and concentrated. Purification of the residue by chromatography (silica gel, eluting with 30 to 60% ethyl acetate in hexanes) provided Compound 213 (2.36 g)

F) Compound 214

Triethylamine trihydrofluoride (4.4 mL, 27.0 mmol) was added to a solution of Compound 213 (4.5 mmol, 2.3 g) and triethylamine (11.4 mmol, 1.6 mL) in THF (45 mL). After stirring at room temperature for 16 hours, the solvent was evaporated under reduced pressure and the residue was purified by chromatography (silica gel, eluting with 5 to 10% methanol in chloroform) provided nucleoside, Compound 214 (1.05 g, 87%).

G) Compounds 215 and 216

Dimethoxytrityl chloride (4.3 mmol, 1.3 g) was added to a solution of Compound 214 (1.05 g, 3.9 mmol) in pyridine (20 mL). After stirring for 16 hours at room temperature, the reaction was diluted with ethyl acetate and the organic layer was extracted with water, brine, dried (Na2SO4) and concentrated. Purification by column chromatography (silica gel, eluting with 15 to 25% acetone in chloroform) provided pure Compound 216 (1.24 g) and a mixture of compounds 215 and 216 (0.42 g) and unreacted Compound 214 (272 mg). Repurification of the mixture by column chromatography as above provided pure Compound 215 (228 mg) and 210 (122 mg).
216 $^1$H NMR (300 MHz, CHLOROFORM-d) δ=8.90 (br. s., 1 H), 8.20 (d, J=8.1 Hz, 1 H), 7.52-7.22 (m, 12 H), 6.96-6.73 (m, 5 H), 5.75 (s, 1 H), 5.52 (dd, J=1.4, 8.2 Hz, 1H), 4.20 (br. s., 1 H), 3.79 (s, 7 H), 3.62 (d, J=11.3 Hz, 1H), 3.31 (d, J=11.3 Hz, 1 H), 2.62 (d, J=5.5 Hz, 1 H), 2.47 (d, J=3.2 Hz, 1 H), 2.17 (s, 2H), 1.89 (s, 1 H), 1.65 (d, J=3.6 Hz, 1 H), 1.23 (d, J=7.3 Hz, 3 H), 1.07 (none, 1H).

215 $^1$H NMR (300 MHz, CHLOROFORM-d) δ=8.94-8.72 (m, 1 H), 8.35-8.10 (m, 1 H), 7.52-7.22 (m, 11 H), 6.97-6.74 (m, 4 H), 5.55-5.41 (m, 1 H), 5.41-5.27 (m, 1 H), 4.22-4.04 (m, 1 H), 3.80 (s, 6 H), 3.74-3.59 (m, 1 H), 3.50-3.30 (m, 1 H), 2.46-2.28 (m, 1 H), 2.28-2.01 (m, 1 H), 2.01-1.75 (m, 1 H), 1.54-1.31 (m, 2 H), 1.21 (none, 3 H).

H) Compound 217

(iPr$_2$N)$_2$POCH$_2$CH$_2$CN (3.4 mmol, 1.1 mL) was added to a solution of Compound 216 (2.3 mmol, 1.3 g), NMI (0.57 mmol, 0.046 g) and tetrazole (1.8 mmol, 0.13 g) in DMF (11 mL). After stirring at room temperature for 6 hours, the reaction was diluted with ethyl acetate and washed with saturated sodium bicarbonate, brine, dried (Na$_2$SO$_4$) and concentrated. Purification by chromatography (silica gel, eluting with 50 to 60% ethyl acetate in hexanes) provided Compound 217 (1.24 g). $^{31}$P NMR (300 MHz, CHLOROFORM-d) δ=148.9, 148.6.

I) Compound 218

(iPr$_2$N)ClPOCH$_2$CH$_2$CN is added to a solution of Compound 215 and DIPEA in dichloromethane. The final product is then isolated and purified according to the procedure described above for Compound 217.

EXAMPLE 35

Preparation of (1R,3R,4R,5R,7S)-7-[2-Cyanoethoxy(diisopropylamino)phosphin oxy]-1-(4,4'-dimethoxytrityloxymethyl)-3-(cytosin-1-yl)-5-methyl-2-oxa-bicyclo[2.2.1]heptane (Compound 222, Scheme 35)

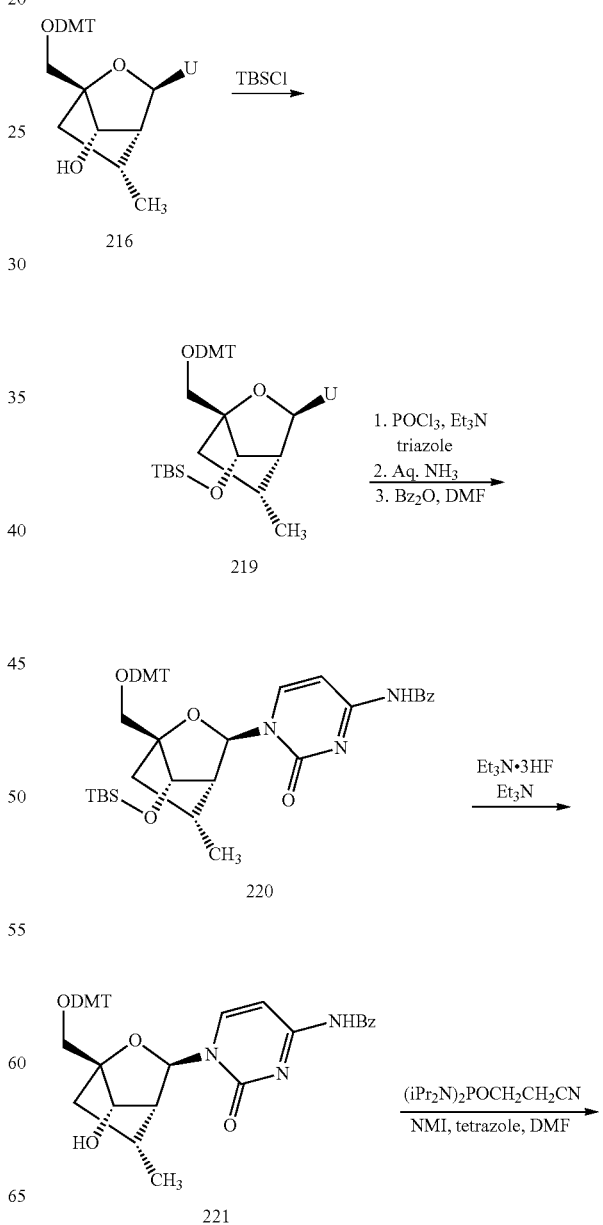

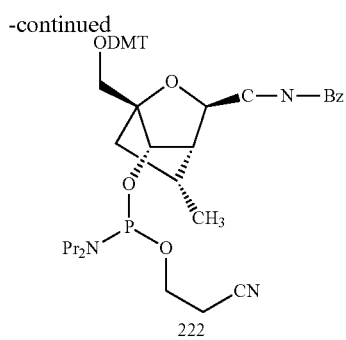

A) Compound 219

Tert-Butyldimethylsilyl chloride (1.2 g) was added to a solution of Compound 216 (1.6 mmol, 0.9 g) and imidazole (1.0 g) in DMF. After stirring at room temperature for 4 days, the reaction was diluted with ethyl acetate and the organic layer was washed with water, brine, dried (Na$_2$SO$_4$) and concentrated. Purification by chromatography (silica gel, eluting with 30 to 40% ethyl acetate in hexanes) provided Compound 219 (0.8 g).

B) Compound 220

Phosphorus oxychloride (13.0 mmol, 1.2 mL) was added to a cold suspension of 1,2,4-triazole (55.1 mmol, 3.8 g) in acetonitrile (16 mL). After stirring for 15 minutes, triethylamine (64.8 mmol, 9.1 mL) was added to the reaction and the white suspension was stirred for another 30 minutes. A solution of compound 219 (1.6 mmol, 1.1 g) in acetonitrile (5 mL) was added to the reaction and the stirring was continued at room temperature for 5 hours. The reaction was then concentrated under reduced pressure and the residue was dissolved in ethyl acetate and the organic layer was washed with water, brine, dried (Na2SO4) and concentrated and the crude material was used in the next step without any purification.

Aqueous ammonia (3.2 mL) was added to a solution of the crude material obtained above in dioxane (16 mL). After stirring at room temperature for 4 hours, the reaction was evaporated to dryness and the residue was purified by chromatography (silica gel, eluting with 20 to 35% acetone in chloroform) to provide the cytosine nucleoside (0.67 g).

Benzoic anhydride (1.9 mmol, 0.43 g) was added to a solution of the cytosine nucleoside from above (1.6 mmol, 1.1 g) in DMF (3 mL). After stirring at room temperature for 24 hours, the reaction was diluted with ethyl acetate and the organic layer was washed with water, brine, dried (Na$_2$SO$_4$) and concentrated. Purification by chromatography (silica gel, eluting with 30 to 50% ethyl acetate in hexanes) provided Compound 220 (1.3 g).

C) Compound 221

Triethylamine trihydrofluoride (9.7 mmol, 1.6 mL) was added to a solution of Compound 220 (1.6 mmol, 1.25 g) and triethylamine (4.0 mmol, 0.6 mL) in THF (16 mL). After stirring at room temperature for 40 hours, additional triethylamine trihydrofluoride (0.8 mL) and triethylamine (0.2 mL) were added to the reaction which was stirred for another 16 hours at room temperature. The reaction was then diluted with ethyl acetate and the organic layer was washed with water, saturated sodium bicarbonate, brine, dried (Na$_2$SO$_4$) and concentrated. Purification by chromatography (silica gel, eluting with 20 to 30% acetone in chloroform) provided Compound 221 (0.94 g, 88%).

D) Compound 222

(iPr$_2$N)$_2$POCH$_2$CH$_2$CN (2.1 mmol, 0.66 mL) was added to a solution of Compound 221 (1.4 mmol, 0.94 g), NMI (0.35 mmol, 0.03 g) and tetrazole (1.1 mmol, 0.08 g) in DMF (7 mL). After stirring at room temperature for 6 hours, the reaction was diluted with ethyl acetate and washed with saturated sodium bicarbonate, brine, dried (Na$_2$SO$_4$) and concentrated. Purification by chromatography (silica gel, eluting with 70 to 80% ethyl acetate in hexanes) provided Compound 222 (1.04 g). $^{31}$P NMR (300 MHz, CHLOROFORM-d) δ=148.9, 148.8.

EXAMPLE 36

Preparation of (1R,3R,4R,5S,7S)-7-[2-Cyanoethoxy(diisopropylamino)phosphin oxy]-1-(4,4'-dimethoxytrityloxymethyl)-3-(cytosin-1-yl)-5-methyl-2-oxa-bicyclo[2.2.1]heptane (Compound 226, Scheme 36)

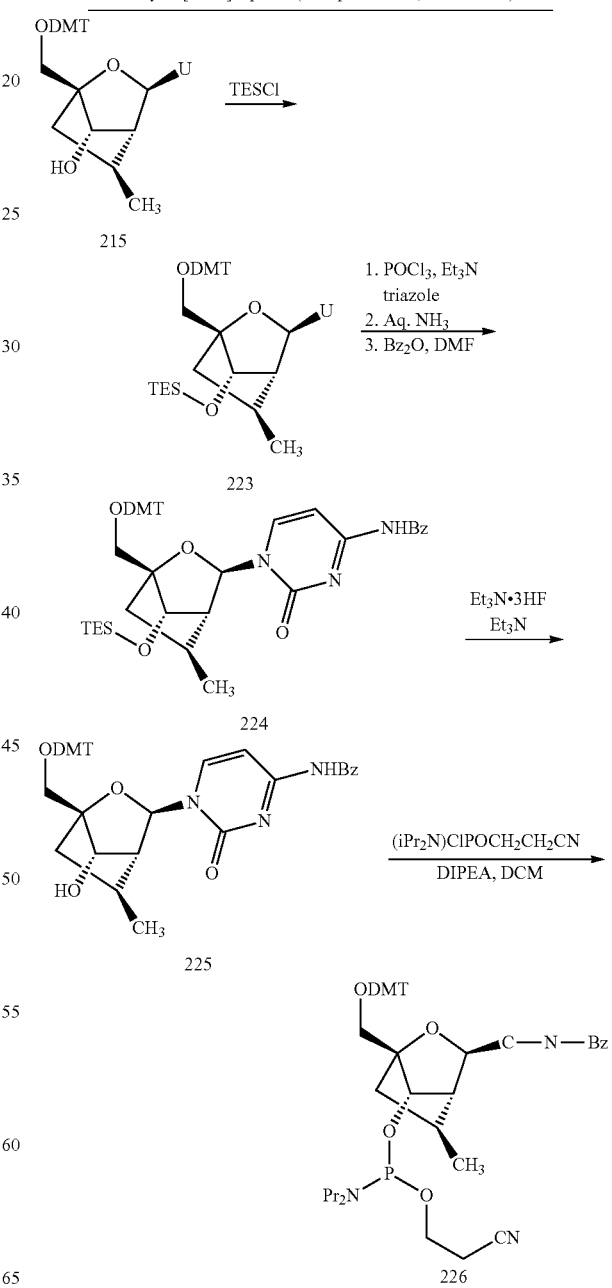

Compound 226 is prepared from Compound 215 (example 34) using the general procedures described in examples 34 and 35.

EXAMPLE 37

Preparation of (1R,3R,4R,5R,7S)- and (1R,3R,4R,5S,7S)-7-[2-Cyanoethoxy(diisopropylamino)phosphin oxy]-1-(4,4'-dimethoxytrityloxymethyl)-3-(adenin-1-yl)-5-methyl-2-oxa-bicyclo[2.2.1]heptane (Compound 231, scheme 37)

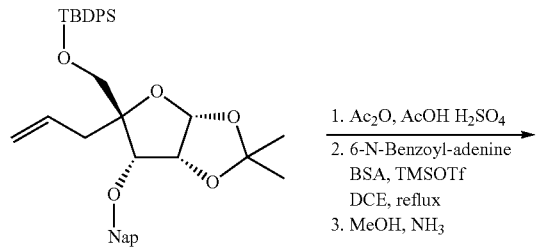

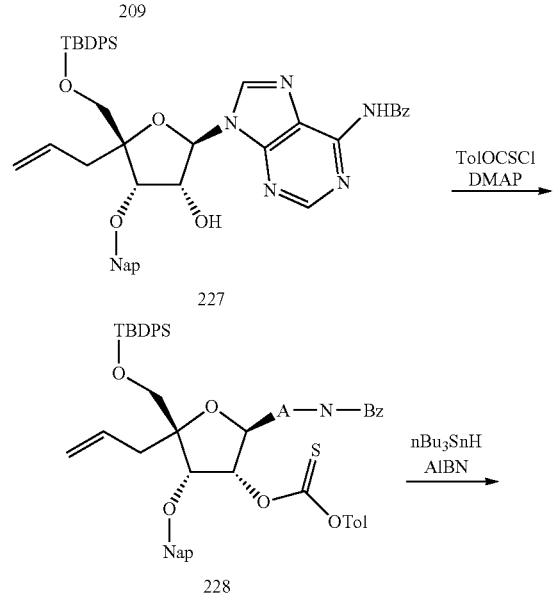

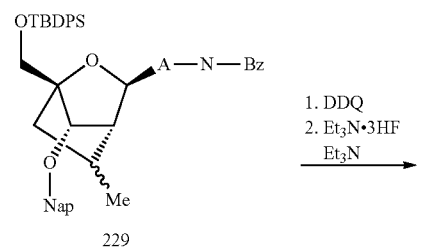

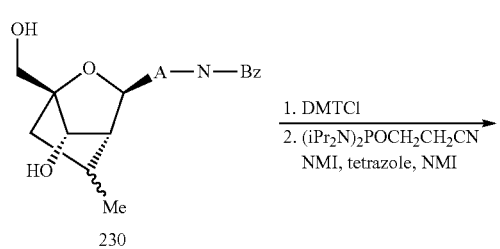

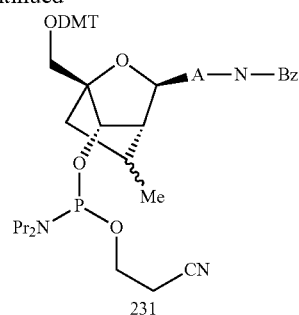

The phosphoramidite, Compound 231 is prepared from Compound 209 (example 34) using the general procedures described in example 29.

EXAMPLE 38

Preparation of (1R,3R,4R,5R,7S)- and (1R,3R,4R,5S,7S)-7-[2-Cyanoethoxy(diisopropylamino)phosphin oxy]-1-(4,4'-dimethoxytrityloxymethyl)-3-(guanin-1-yl)-5-methyl-2-oxa-bicyclo[2.2.1]heptane (Compound 238, Scheme 38)

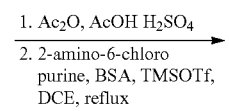

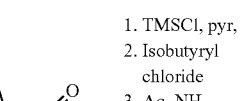

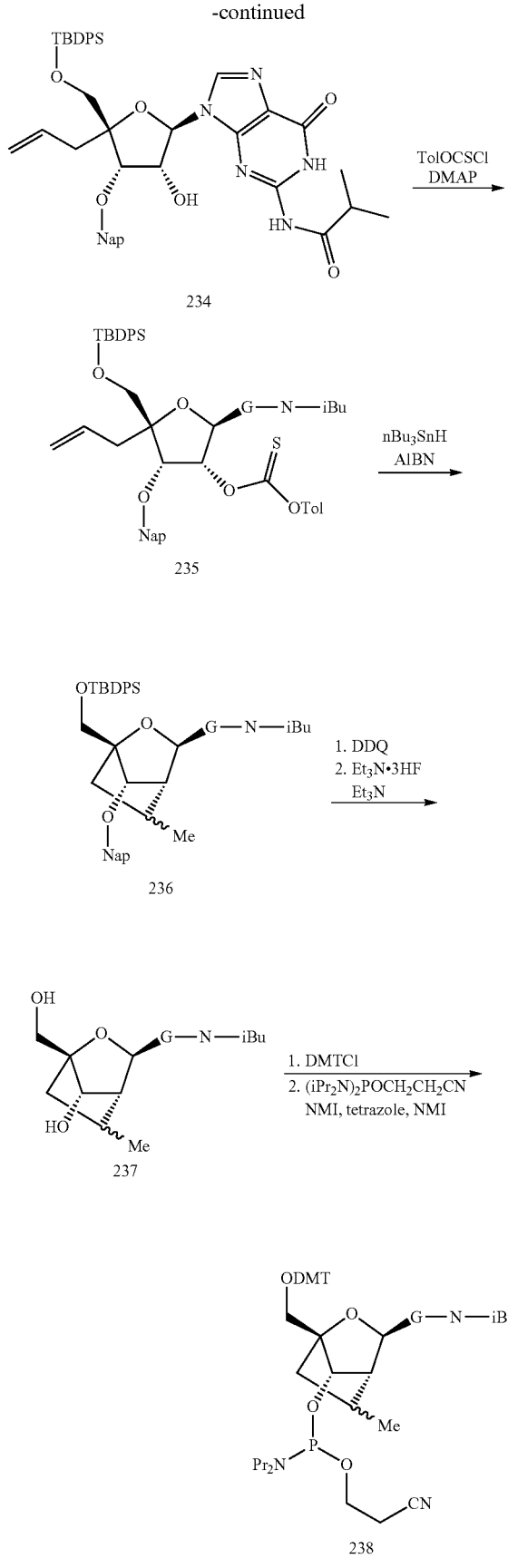
The phosphoramidite, Compound 238 is prepared from Compound 209 (example 34) using the general procedures described in example 30.
EXAMPLE 39
Preparation of compound 246
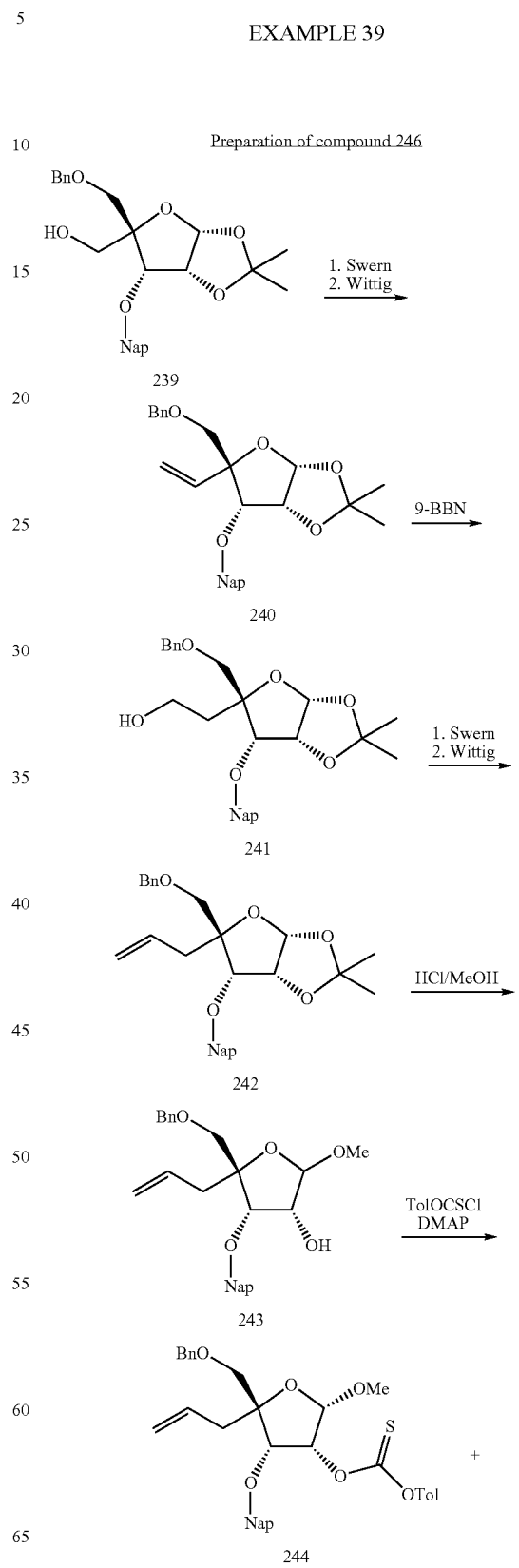

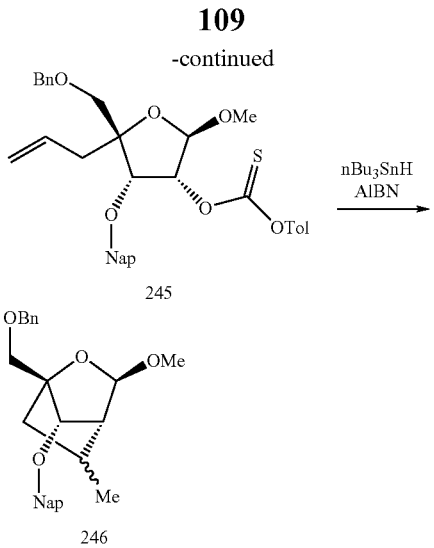

A) Compound 240

Dimethylsulfoxide (103.6 mmol, 7.3 mL) was added dropwise to a cold (−78° C. solution of oxalyl chloride (51.8 mmol, 4.5 mL) in dichloromethane (320 mL). After stirring for 30 minutes, a solution of commercially available alcohol, Compound 239 (37.0 mmol, 16.7 g) in dichloromethane (50 mL) was added to the reaction via a canula and stirring was continued for another 45 minutes at −78° C. Triethylamine (155 mmol, 21.8 mL) was added and the reaction was removed from the cold bath and stirring was continued for another 30 minutes. The reaction was then diluted with dichloromethane and washed sequentially with 5% HCl, saturated NaHCO$_3$, brine, dried (Na$_2$SO$_4$) and concentrated to provide the corresponding aldehyde which was used in the next step without any purification.

nBuLi (51.8 mmol, 20.7 mL of a 2.5 M solution) was added to a cold (0° C.) solution of methyltriphenyphosphonium bromide (51.8 mmol, 18.5 g) in THF (300 mL). After stirring for 2 hours in the ice bath, the deep red solution was cooled to −78° C. and a solution of the crude aldehyde from above in THF (50 mL) was added to the reaction over 20 minutes. The reaction was allowed to warm to room temperature gradually and stirred for 16 hours. Saturated ammonium chloride was added to the reaction and roughly 80% of the THF was evaporated under reduced pressure. The resulting oil was diluted with ethyl acetatae and the organic layer was washed with water, brine, dried (Na$_2$SO$_4$) and concentrated. The crude material was purified by chromatography (silica gel, eluting with hexanes—20% ethyl acetate in hexanes) to provide Compound 240.

B) Compound 241

A solution of Compound 240 (42.6 mmol, 19.0 g) in THF (30 mL) was added to a solution of 9-BBN (0.5 M in THF, 127.8 mmol, 256 mL). After stirring at room temperature for 24 hours, the reaction was cooled in an ice bath and carefully quenched with EtOH. A suspension of sodium perborate tetrahydrate (255 mmol, 39.0 g) in ethanol (255 mL) and water (255 mL) was added to the reaction and the mixture was heated at 50° C. for 4 hours. Roughly 80% of the solvent was evaporated under reduced pressure and the residue was suspended in ethyl acetate and washed sequentially with water, brine, dried (Na$_2$SO$_4$) and concentrated. The residue was purified by chromatography (silica gel, eluting with 10 to 30% ethyl acetate in hexanes) to provide the alcohol, Compound 241 (19.8 g, 88%) as an oil.

C) Compound 242

Dimethylsulfoxide (112.9 mmol, 8.0 mL) was added dropwise to a cold (−78° C.) solution of oxalyl chloride (56.5 mmol, 4.9 mL) in dichloromethane (320 mL). After stirring for 30 minutes, a solution of Compound 241 (37.3 mmol, 17.5 g) in dichloromethane (50 mL) was added to the reaction via a canula and stirring was continued for another 45 minutes at −78° C. Triethylamine (169.4 mmol, 23.8 mL) was added and the reaction was removed from the cold bath and stirring was continued for another 30 minutes. The reaction was then diluted with dichloromethane and washed sequentially with 5% HCl, saturated NaHCO$_3$, brine, dried (Na$_2$SO$_4$) and concentrated to provide the corresponding aldehyde which was used in the next step without any purification.

nBuLi (56.5 mmol, 22.6 mL of a 2.5 M solution in hexanes) was added to a cold (0° C.) suspension of methyl triphenylphosphoniumbromide (56.5 mmol, 20.2 g) in THF (350 mL). After stirring for 2 hours, the reaction was cooled to −78° C. and a solution of the aldehyde (37.7 mmol) from above in THF (50 mL) was added to the reaction which was gradually allowed to warm to room temperature and stirred for another 16 hours. The reaction was quenched with saturated ammonium chloride and the solvent was removed under reduced pressure. The residue was dissolved in ethyl acetate and the organic layer was washed with water, brine, dried (Na$_2$SO$_4$) and concentrated. Purification by chromatography (silica gel, eluting with hexanes to 15% ethyl acetate in hexanes) provided Compound 242 (7.8 g).

D) Compound 243

HCl (2.2 mmol, 0.54 mL of a 4M solution in dioxane) was added to a cold (0° C.) solution of Compound 242 (1.1 mmol, 0.5 g) in dry methanol (10 mL). After stirring at 0° C. for 1 hour, the reaction was quenched with saturated sodium bicarbonate solution and extracted with ethyl acetate. The organic layer was washed with brine, dried (Na$_2$SO$_4$) and concentrated to provide Compound 243 (0.44 g).

E) Compounds 244 and 245

Tolyl-chlorothionoformate (1.2 mmol, 0.19 mL) was added drop-side to a cold (0° C.) solution of Compound 243 (1.0 mmol, 0.44) and dimethylaminopyridine (2.0 mmol, 0.24 g) in acetonitrile (10 mL). After stirring for 16 hours at room temperature, the reaction was quenched with methanol. Roughly 50% of the solvent was evaporated under reduced pressure and the reaction was diluted with ethyl acetate and washed with 5% HCl, saturated sodium bicarbonate, brine, dried (Na$_2$SO$_4$) and concentrated. Purification by chromatography (silica gel, eluting with 10 to 20% ethyl acetate in hexanes) provided Compound 244 (0.21 g) and Compound 245 (0.15 g).

I) Compound 246

A solution of Compound 245 (0.26 mmol, 0.15 g) in toluene (8 mL) was refluxed for 30 minutes. A solution of nBu$_3$SnH (0.26 mmol, 0.07 mL) in toluene (1 mL) was added drop-wise to the refluxing reaction. After about half (0.5 mL) of the nBu$_3$SnH solution was added to the reaction (30 minutes), a solution of AIBN (0.26 mmol, 0.043 g) in toluene (1 mL) was added drop-wise to the reaction over 90 minutes. After refluxing for another 2 hours, the reaction was cooled and the solvent was evaporated under reduced pressure. The residue was diluted with ether and washed with saturated KF solution, brine, dried (Na$_2$SO$_4$) and concentrated. Purification of the residue by chromatography (silica gel, eluting with 20 to 40% ethyl acetate in hexanes) provided Compound 246 (0.05 g). $^1$H NMR (300 MHz, CHLOROFORM-d) δ=7.89-7.77 (m, 3H), 7.47-7.44 (m, 2H), 7.39-7.24 (m, 7H), 4.86 (s, 1H), 4.70-4.57 (m, 4H), 4.29 (s, 1H), 3.68 (m, 2H), 3.37 (s, 3H), 2.54-2.48 (m, 1H), 2.35-2.31 (m, 1H), 2.11-1.99 (m, 1H), 1.22-1.17 (m, 1H), 1.11 (d, 3H, J=7.2).

EXAMPLE 40
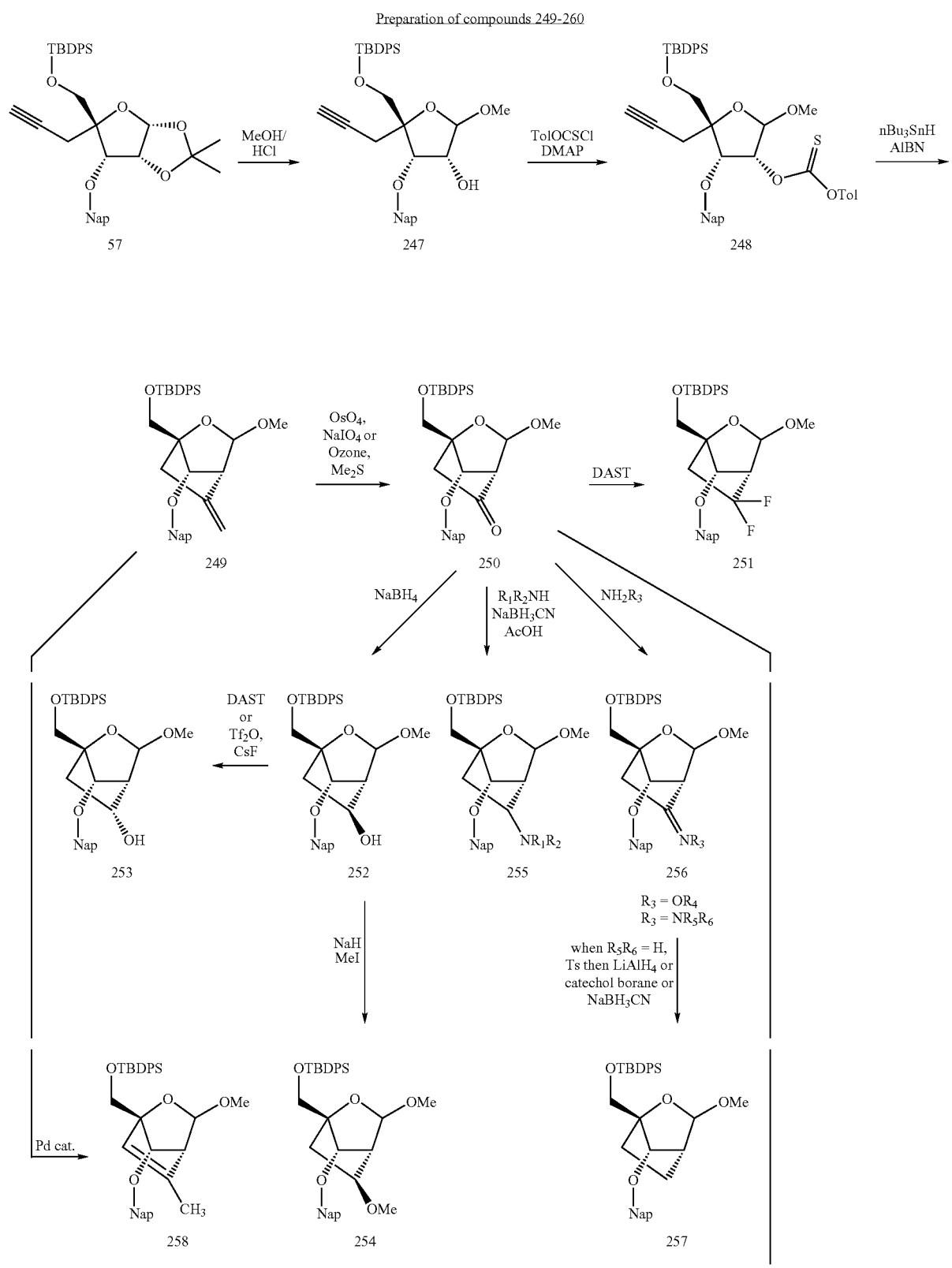
Preparation of compounds 249-260

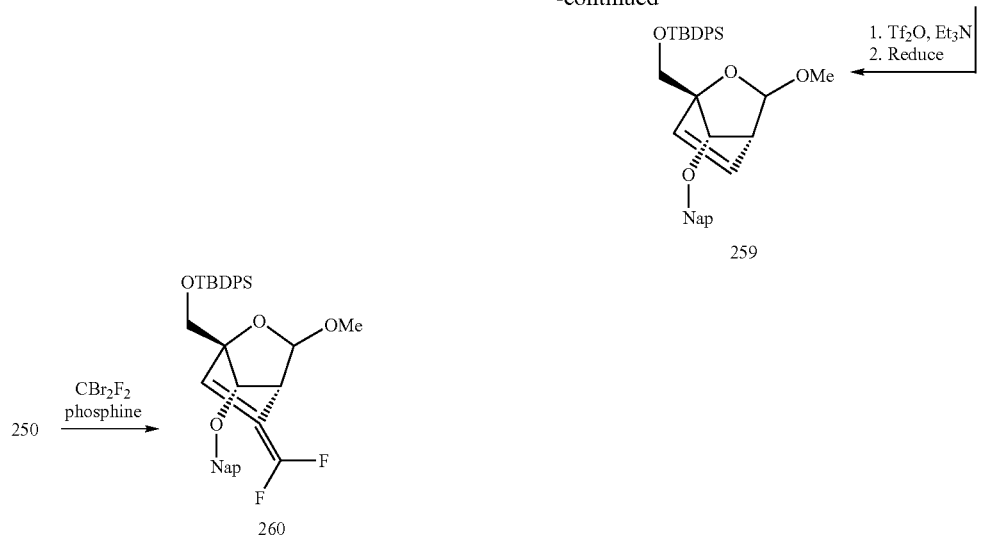

Compound 249 is prepared from Compound 57 (example 27) using the general procedures described in examples 39 and 27. Compounds 250 is prepared from compound 249 by an oxidative cleavage reaction using osmium tetroxide and sodium periodate or ozone. Compound 251 is prepared by difluorination of Compound 250 using DAST or any other suitable fluorinating reagent. Compound 252 is prepared from Compound 250 by reducing with sodium borohydride. Fluorination of Compound 252 with DAST provides Compound 253.

Alkylation of Compound 252 using a strong base like sodium hydride and an alkylating agent like methyl iodide provides Compound 254. A reductive amination reaction of Compound 250 provides the amino substituted Compound 255. Reaction of Compound 250 with a hydroxylamine or hydrazine compound provides the corresponding oxime or hydrazone, Compound 256. When the hydrazine used is tosylhydrazine, Compound 256 is reduced using a reducing agent like LiAlH$_4$, catechol borane or sodium cyanoborohydride to provide Compound 257. Compound 249 is isomerized to the more stable internal olefin using palladium or rhodium or any other suitable olefin isomerization catalyst to provide Compound 258. Compound 250 is converted to the corresponding enol-triflate followed by a reduction reaction to provide Compound 259. Compound 250 is converted to the difluoro olefin, Compound 260a using CBr$_2$F$_2$ and a phosphine reagent.

EXAMPLE 41

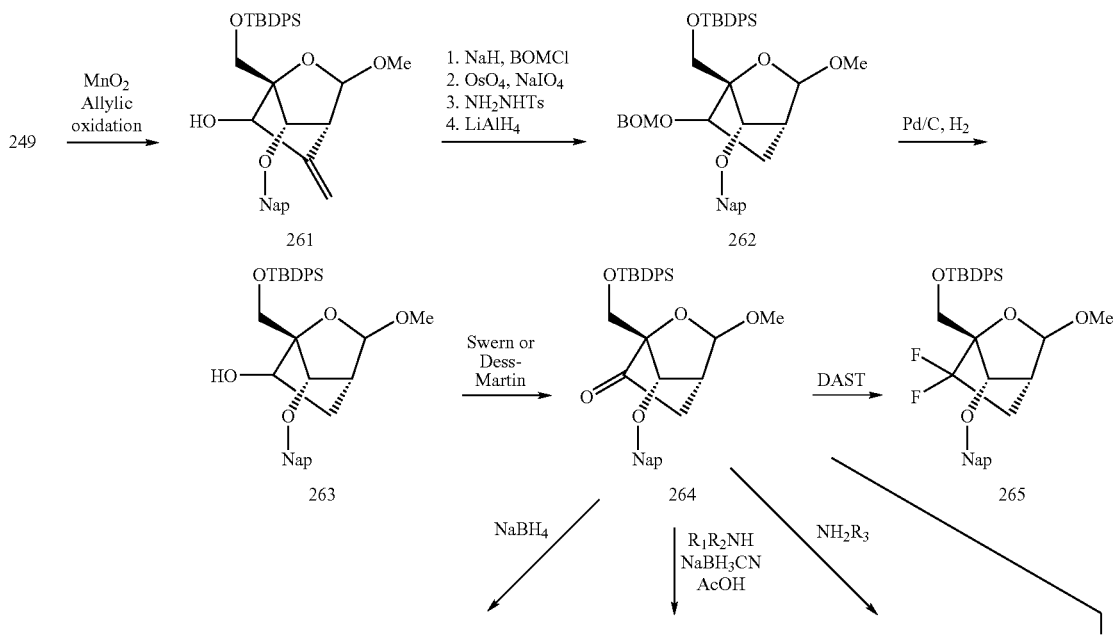

-continued

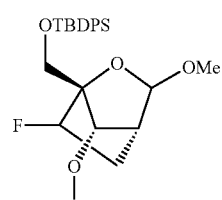
266

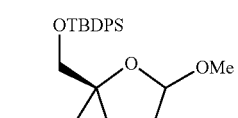

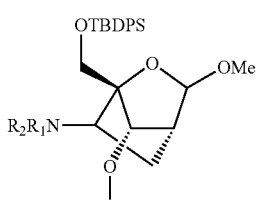
267    268    269

$R_3 = OR_4$
$R_3 = NR_5R_6$

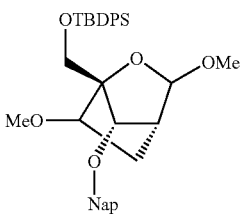
270

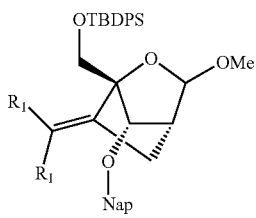
271

($R_1$ = H or F)

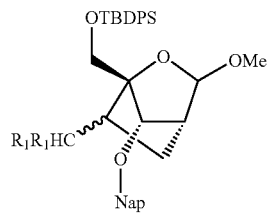
272

($R_1$ = H or F)

Compound 261 is prepared from Compound 249 (example 40) by means of an allylic oxidation reaction using a suitable oxidant such as manganese dioxide. The hydroxyl group is then protected as the benzyloxymethyl ether and the double bond is cleaved using osmium tetroxide and sodium periodate or ozone. Reaction of this ketone with tosylhydrazine followed by reduction with lithium aluminum hydride or catecholborane or sodium cyanoborohydride provides Compound 262. Removal of the BOM group in 262 provides the alcohol, Compound 263. Oxidation of the alcohol in Compound 263 provides the ketone, Compound 264 which is converted to the (difluoro-compound) Compound 265 using DAST or any other suitable fluorinating agent. Compound 264 is reduced to Compound 267 using sodium borohydride. Compound 267 is converted to the fluoro analog, Compound 266 using DAST or any other suitable fluorinating reagent. Compound 264 is converted to Compound 268 by a reductive amination reaction. Compound 264 is converted to the oxime/hydrazone, Compound 269 by reaction with a hydroxylamine or hydrazine. Compound 270 is prepared from Compound 269 by means of an alkylation reaction using a strong base and an alkylating agent such as methyl iodide. Compound 271 is prepared from Compound 264 by means of a Wittig reaction using appropriate conditions. Compound 272 is prepared from compound 271 by a reduction reaction using catalytic palladium on charcoal and hydrogen.

EXAMPLE 42

Preparation of compound 277

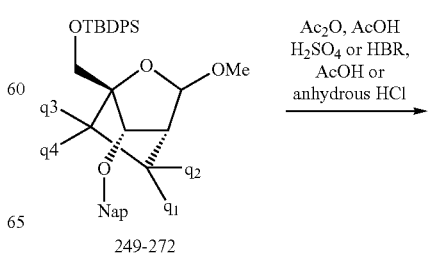
249-272

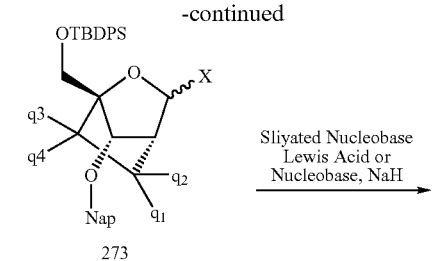

273

X = OAc, Br or Cl

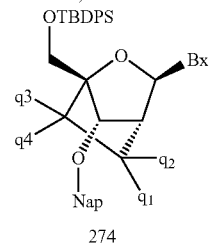

274

+

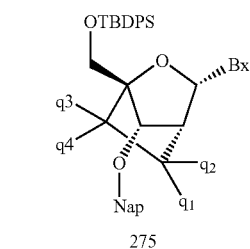

275

1. DDQ
2. Et$_3$N·3HF
   Et$_3$N

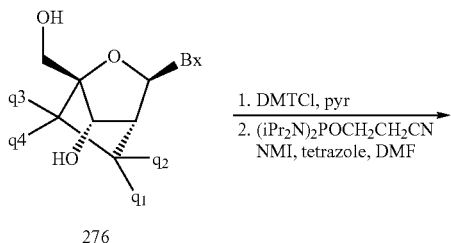

276

1. DMTCl, pyr
2. (iPr$_2$N)$_2$POCH$_2$CH$_2$CN
   NMI, tetrazole, DMF

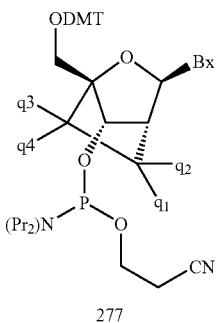

277

Compounds 249-272 are prepared as described in example 40 and 41 are treated with a mixture of acetic acid, acetic anhydride and catalytic sulfuric acid or HBr/acetic acid or HCl provides Compound 273. Treatment of Compound 273 with a silyated nucleobase and a Lewis acid or the sodium salt of an appropriately protected nucleobase provides a mixture of anomeric nucleosides Compound 274 and Compound 275. Removal of the 3'-O and 5'-O protecting groups in Compound 274 provides the nucleosides, Compound 276. Protection of the 5'-hydroxyl group as the DMT ether followed by phosphitylation of the 3'-hydroxyl group provides the desired phosphoramidites, Compound 277.

EXAMPLE 43

Synthesis of Nucleoside Phosphoramidites

The preparation of nucleoside phosphoramidites is performed following procedures that are illustrated herein and in the art such as but not limited to U.S. Pat. No. 6,426,220 and published PCT WO 02/36743.

EXAMPLE 44

Oligonucleotide and Oligonucleoside Synthesis

The oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Oligonucleotides with unsubstituted and substituted phosphodiester (P=O) internucleoside linkages can be synthesized on an automated DNA synthesizer (Applied Biosystems model 394) using standard phosphoramidite chemistry with oxidation by iodine.

Oligonucleotides with phosphorothioate internucleoside linkages (P=S) are synthesized similar to phosphodiester oligonucleotides with the following exceptions: thiation is effected by utilizing a 0.2 M solution of phenylacetyl disulfide in 50% 3-picoline in acetonitrile for the oxidation of the phosphite linkages. The thiation reaction step time is increased to 180 sec and preceded by the normal capping step. After cleavage from the CPG column and deblocking in concentrated ammonium hydroxide at 55° C. (12-16 hr), the oligonucleotides are recovered by precipitating with greater than 3 volumes of ethanol from a 1 M NH$_4$OAc solution. Phosphinate oligonucleotides can be prepared as described in U.S. Pat. No. 5,508,270.

Alkyl phosphonate oligonucleotides can be prepared as described in U.S. Pat. No. 4,469,863.

3'-Deoxy-3'-methylene phosphonate oligonucleotides can be prepared as described in U.S. Pat. Nos. 5,610,289 or 5,625,050.

Phosphoramidite oligonucleotides can be prepared as described in U.S. Pat. Nos. 5,256,775 or 5,366,878.

Alkylphosphonothioate oligonucleotides can be prepared as described in published PCT applications PCT/US94/00902 and PCT/US93/06976 (published as WO 94/17093 and WO 94/02499, respectively).

3'-Deoxy-3'-amino phosphoramidate oligonucleotides can be prepared as described in U.S. Pat. No. 5,476,925.

Phosphotriester oligonucleotides can be prepared as described in U.S. Pat. No. 5,023,243.

Borano phosphate oligonucleotides can be prepared as described in U.S. Pat. Nos. 5,130,302 and 5,177,198.

Oligonucleosides: Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleo-sides, as well as mixed backbone oligomeric compounds having, for instance, alternating MMI and P=O or P=S linkages can be prepared as described in U.S. Pat. Nos. 5,378,825; 5,386,023; 5,489,677; 5,602,240 and 5,610,289.

Formacetal and thioformacetal linked oligonucleosides can be prepared as described in U.S. Pat. Nos. 5,264,562 and 5,264,564.

Ethylene oxide linked oligonucleosides can be prepared as described in U.S. Pat. No. 5,223,618.

EXAMPLE 45

Oligonucleotide Isolation

After cleavage from the controlled pore glass solid support and deblocking in concentrated ammonium hydroxide at 55° C. for 12-16 hours, the oligonucleotides or oligonucleosides are recovered by precipitation out of 1 M $NH_4OAc$ with >3 volumes of ethanol. Synthesized oligonucleotides are analyzed by electrospray mass spectroscopy (molecular weight determination) and by capillary gel electrophoresis. The relative amounts of phosphorothioate and phosphodiester linkages obtained in the synthesis is determined by the ratio of correct molecular weight relative to the −16 amu product (+/−32 +/−48). For some studies oligonucleotides are purified by HPLC, as described by Chiang et al., J. Biol. Chem. 1991, 266, 18162-18171. Results obtained with HPLC-purified material are generally similar to those obtained with non-HPLC purified material.

EXAMPLE 46

Oligonucleotide Synthesis-96 Well Plate Format

Oligonucleotides can be synthesized via solid phase P(III) phosphoramidite chemistry on an automated synthesizer capable of assembling 96 sequences simultaneously in a 96-well format. Phosphodiester internucleotide linkages are afforded by oxidation with aqueous iodine. Phosphorothioate internucleotide linkages are generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites are purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides are cleaved from support and deprotected with concentrated $NH_4OH$ at elevated temperature (55-60° C.) for 12-16 hours and the released product then dried in vacuo. The dried product is then re-suspended in sterile water to afford a master plate from which all analytical and test plate samples are then diluted utilizing robotic pipettors.

EXAMPLE 47

Oligonucleotide Analysis Using 96-Well Plate Format

The concentration of oligonucleotide in each well is assessed by dilution of samples and UV absorption spectroscopy. The full-length integrity of the individual products is evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition is confirmed by mass analysis of the oligomeric compounds utilizing electrospray-mass spectroscopy. All assay test plates are diluted from the master plate using single and multi-channel robotic pipettors. Plates are judged to be acceptable if at least 85% of the oligomeric compounds on the plate are at least 85% full length.

EXAMPLE 48

Cell Culture and Oligonucleotide Treatment

The effect of oligomeric compounds on target nucleic acid expression can be tested in any of a variety of cell types provided that the target nucleic acid is present at measurable levels. This can be routinely determined using, for example, PCR or Northern blot analysis. Cell lines derived from multiple tissues and species can be obtained from American Type Culture Collection (ATCC, Manassas, Va.).

The following cell type is provided for illustrative purposes, a plurality of other cell types can be routinely used, provided that the target is expressed in the cell type chosen. This can be readily determined by methods routine in the art, for example Northern blot analysis, ribonuclease protection assays or RT-PCR.

B.END cells: The mouse brain endothelial cell line b.END was obtained from Dr. Werner Risau at the Max Plank Institute (Bad Nauheim, Germany). b.END cells were routinely cultured in DMEM, high glucose (Invitrogen Life Technologies, Carlsbad, Calif.) supplemented with 10% fetal bovine serum (Invitrogen Life Technologies, Carlsbad, Calif.). Cells were routinely passaged by trypsinization and dilution when they reached approximately 90% confluence. Cells were seeded into 96-well plates (Falcon-Primaria #353872, BD Biosciences, Bedford, Mass.) at a density of approximately 3000 cells/well for uses including but not limited to oligomeric compound transfection experiments.

Experiments involving treatment of cells with oligomeric compounds:

When cells reach appropriate confluency, they are treated with oligomeric compounds using, in certain embodiments, a transfection method as described.

LIPOFECTIN™

When cells reached 65-75% confluency, they are treated with an oligonucleotide. The selected oligonucleotide is mixed with LIPOFECTIN™ Invitrogen Life Technologies, Carlsbad, Calif.) in Opti-MEM™-1 reduced serum medium (Invitrogen Life Technologies, Carlsbad, Calif.) to achieve the desired concentration of oligonucleotide and a LIPOFECTIN™ concentration of 2.5 or 3 µg/mL per 100 nM oligonucleotide. This transfection mixture is incubated at room temperature for approximately 0.5 hours. For cells grown in 96-well plates, wells are washed once with 100 µL. OPTI-MEM™-1 and then treated with 130 µL of the transfection mixture. Cells grown in 24-well plates or other standard tissue culture plates are treated similarly, using appropriate volumes of medium and oligonucleotide. Cells are treated and data are obtained in duplicate or triplicate. After approximately 4-7 hours of treatment at 37° C., the medium containing the transfection mixture is replaced with fresh culture medium. Cells are harvested 16-24 hours after oligonucleotide treatment.

Other suitable transfection reagents known in the art include, but are not limited to, CYTOFECTINT™, LIPOFECTAMINE™, OLIGOFECTAMINE™, and FUGENE™. Other suitable transfection methods known in the art include, but are not limited to, electroporation.

EXAMPLE 49

Analysis of Oligonucleotide Inhibition of a Target Expression

Antisense modulation of a target expression can be assayed in a variety of ways known in the art. For example, a target mRNA levels can be quantitated by, e.g., Northern blot analysis, competitive polymerase chain reaction (PCR), or real-time PCR. Real-time quantitative PCR is presently desired.

RNA analysis can be performed on total cellular RNA or poly(A)+ mRNA. One method of RNA analysis is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of a target can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Methods for preparation of polyclonal antisera are taught in, for example, Ausubel, F. M. et al., *Current Protocols in Molecular Biology*, Volume 2, pp. 11.12.1-11.12.9, John Wiley & Sons, Inc., 1997. Preparation of Monoclonal Antibodies is Taught in, for Example, Ausubel, F. M. et al., *Current Protocols in Molecular Biology*, Volume 2, pp. 11.4.1-11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1-10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1-11.2.22, John Wiley & Sons, Inc., 1991.

EXAMPLE 50

Design of Phenotypic Assays and in Vivo Studies for the Use of Target Inhibitors
Phenotypic Assays Once target inhibitors have been identified by the methods disclosed herein, the oligomeric compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of a target in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with a target inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Measurement of the expression of one or more of the genes of the cell after treatment is also used as an indicator of the efficacy or potency of the a target inhibitors. Hallmark genes, or those genes suspected to be associated with a specific disease state, condition, or phenotype, are measured in both treated and untreated cells.
In Vivo Studies The individual subjects of the in vivo studies described herein are warm-blooded vertebrate animals, which includes humans.

EXAMPLE 51

RNA Isolation
Poly(A)+ mRNA Isolation

In certain embodiments, poly(A)+ mRNA is isolated according to Miura et al., (Clin. Chem., 1996, 42, 1758-1764). Other methods for poly(A)+ mRNA isolation are routine in the art. Briefly, for cells grown on 96-well plates, growth medium is removed from the cells and each well is washed with 200 µl, cold PBS. 60 µl, lysis buffer (10 mM Tris-HCl, pH 7.6, 1 mM EDTA, 0.5 M NaCl, 0.5% NP-40, 20 mM vanadyl-ribonucleoside complex) is added to each well, the plate is gently agitated and then incubated at room temperature for five minutes. 55 µL of lysate is transferred to Oligo d(T) coated 96-well plates (AGCT Inc., Irvine Calif.). Plates are incubated for 60 minutes at room temperature, washed 3 times with 200 µL of wash buffer (10 mM Tris-HCl pH 7.6, 1 mM EDTA, 0.3 M NaCl). After the final wash, the plate is blotted on paper towels to remove excess wash buffer and then air-dried for 5 minutes. 60 µL of elution buffer (5 mM Tris-HCl pH 7.6), preheated to 70° C., is added to each well, the plate is incubated on a 90° C. hot plate for 5 minutes, and the eluate is then transferred to a fresh 96-well plate.

Cells grown on 100 mm or other standard plates may be treated similarly, using appropriate volumes of all solutions.
Total RNA Isolation Total RNA is isolated using an RNEASY 96™ kit and buffers purchased from Qiagen Inc. (Valencia, Calif.) following the manufacturer's recommended procedures. Briefly, for cells grown on 96-well plates, growth medium is removed from the cells and each well is washed with 200 µL cold PBS. 150 µL Buffer RLT is added to each well and the plate vigorously agitated for 20 seconds. 150 µl, of 70% ethanol is then added to each well and the contents mixed by pipetting three times up and down. The samples are then transferred to the RNEASY 96™ well plate attached to a QIAVAC™ manifold fitted with a waste collection tray and attached to a vacuum source. Vacuum is applied for 1 minute. 500 µL of Buffer RW1 is added to each well of the RNEASY 96™ plate and incubated for 15 minutes and the vacuum is again applied for 1 minute. An additional 500 μL of Buffer RW1 is added to each well of the RNEASY 96™ plate and the vacuum is applied for 2 minutes. 1 mL of Buffer RPE is then added to each well of the RNEASY 96™ plate and the vacuum applied for a period of 90 seconds. The Buffer RPE wash is then repeated and the vacuum is applied for an additional 3 minutes. The plate is then removed from the QIAVAC™ manifold and blotted dry on paper towels. The plate is then re-attached to the QIAVAC™ manifold fitted with a collection tube rack containing 1.2 mL collection tubes. RNA is then eluted by pipetting 140 μL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

EXAMPLE 52

Real-time Quantitative PCR Analysis of Target mRNA Levels

In certain embodiments, quantitation of a target mRNA levels is accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

RT and PCR reagents are obtained from Invitrogen Life Technologies (Carlsbad, Calif.). RT, real-time PCR is carried out by adding 20 μl PCR cocktail (2.5×PCR buffer minus $MgCl_2$, 6.6 mM $MgCl_2$, 375 μM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 μL total RNA solution (20-200 ng). The RT reaction is carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

In certain embodiments, gene target quantities obtained by RT, real-time PCR are normalized using either the expression level of GAPDH, a gene whose expression is constant, or by quantifying total RNA using RIBOGREEN™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RIBOGREEN™ are taught in Jones, L. J., et al, (Analytical Biochemistry, 1998, 265, 368-374).

In this assay, 170 μL of RIBOGREEN™ working reagent (RIBOGREEN™ reagent diluted 1:350 in 10 mM Tris-HCl, 1 mM EDTA, pH 7.5) is pipetted into a 96-well plate containing 30 μL purified, cellular RNA. The plate is read in a CytoFluor 4000 (PE Applied Biosystems) with excitation at 485 nm and emission at 530 nm.

EXAMPLE 53

Target-specific Primers and Probes

Probes and primers may be designed to hybridize to a target sequence, using published sequence information.

For example, for human PTEN, the following primer-probe set was designed using published sequence information (GENBANK™ accession number U92436.1, SEQ ID NO: 01).

```
Forward primer:
AATGGCTAAGTGAAGATGACAATCAT    (SEQ ID NO: 02)

Reverse primer:
TGCACATATCATTACACCAGTTCGT     (SEQ ID NO: 03)
```

And the PCR probe:

```
                                           (SEQ ID NO: 04)
    FAM-TTGCAGCAATTCACTGTAAAGCTGGAAAGG-TAMRA,
``` where FAM is the fluorescent dye and TAMRA is the quencher dye.

EXAMPLE 54

Western Blot Analysis of Target Protein Levels

Western blot analysis (immunoblot analysis) is routinely carried out using standard methods. Cells are harvested 16-20 h after oligonucleotide treatment, washed once with PBS, suspended in Laemmli buffer (100 µl/well), boiled for 5 minutes and loaded on a 16% SDS-PAGE gel. Gels are run for 1.5 hours at 150 V, and transferred to membrane for western blotting. Appropriate primary antibody directed to a target is used, with a radiolabeled or fluorescently labeled secondary antibody directed against the primary antibody species. Bands are visualized using a PHOSPHORIMAGER™ (Molecular Dynamics, Sunnyvale Calif.).

EXAMPLE 55

Effects of Antisense Compounds Targeting PTEN in Vitro Study

Oligomeric compounds were synthesized and tested for their ability to reduce PTEN expression over a range of doses. Mouse primary hepatocytes were treated with the modified oligomers listed below at concentrations of 0.625, 12.5, 25, 50, 100 and 200 nM using Cytofectin with methods described herein. Expression levels of PTEN were determined using real-time PCR and normalized to RIBOGREEN™ as described in other examples herein. The percent inhibition of PTEN mRNA was determined. Resulting dose-response curves were used to determine the $IC_{50}$ and Tm's were assessed in 100 mM phosphate buffer, 0.1 mM EDTA, pH 7, at 260 nm using 4 µM modified oligomers and 4 µM complementary length matched RNA. The activities are listed below.

| SEQ ID NO/ ISIS NO | Sequence | $IC_{50}$ | Tm °C. |
|---|---|---|---|
| 05/394425 | $^{Me}C_lT_lGCTAGCCTCTGGATT_lT_l$ | 42 | 61.6 |
| 06/411001 | $C_{cm}U_{cm}GCTAGCCTCTGGATU_{cm}U_{cm}$ | 49 | 58.8 |
| 06/425453 | $C_{cv}U_{cv}GCTAGCCTCTGGATU_{cv}U_{cv}$ | 44 | 60.5 |

Each internucleoside linking group is a phosphorothioate, superscript Me indicates that the following cytidine is a 5-methyl cytidine, each nucleoside not otherwise annotated is a 2'-deoxyribonucleoside and nucleosides followed by a subscript are defined as shown below:

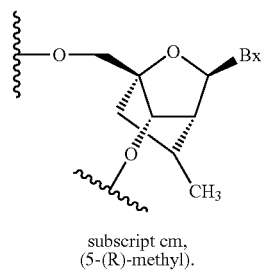
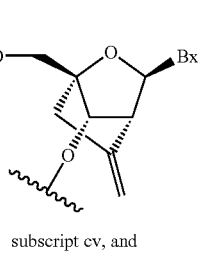

subscript cm, (5-(R)-methyl). subscript cv, and

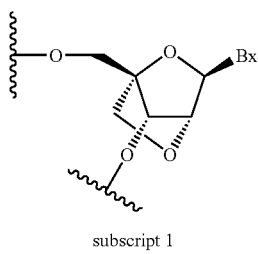

subscript 1

| SEQ ID NO/ | % of untreated control of PTEN mRNA @ Dose (nM) | | | | | |
|---|---|---|---|---|---|---|
| ISIS NO | 6.25 | 12.5 | 25 | 50 | 100 | 200 |
| 05/394425 | 136 | 97 | 73 | 39 | 16 | 3 |
| 06/411001 | 128 | 94 | 96 | 41 | 21 | 4 |
| 06/425453 | 116 | 95 | 82 | 39 | 15 | 3. |

EXAMPLE 56

Effects of Antisense Compounds Targeting PTEN in Vivo Study

Six week old male Balb/c mice (Jackson Laboratory, Bar Harbor, Me.) were injected once with modified oligomers targeted to PTEN at doses of 3.2, 10, 32 and 100 mg/kg. The mice were sacrificed 64 hours following the final administration. Liver tissues were homogenized and PTEN mRNA levels were quantitated using real-time PCR and RIBOGREEN® RNA quantification reagent (Molecular Probes, Inc. Eugene, Oreg.) according to standard protocols. PTEN mRNA levels were determined relative to total RNA (using Ribogreen), prior to normalization to saline-treated control. The relative activities of the antisense compounds are shown below with the results presented as the average % inhibition of mRNA expression for each antisense compound, normalized to saline-injected control.

| SEQ ID NO/ ISIS NO | Sequence | PTEN % Inhibition (mg/kg dose) | | | |
|---|---|---|---|---|---|
| | | 1.9 | 6 | 19 | 60 |
| 05/394425 | $^{Me}C_lT_lGCTAGCCTCTGGATT_lT_l$ | 0 | 65 | 92 | 96 |
| 06/411001 | $C_{cm}U_{cm}GCTAGCCTCTGGATU_{cm}U_{cm}$ | 0 | 10 | 56 | 89 |
| 06/425453 | $C_{cv}U_{cv}GCTAGCCTCTGGATU_{cv}U_{cv}$ | 29 | 57 | 83 | 95 |

Each internucleoside linking group is a phosphorothioate, superscript Me indicates that the following cytidine is a 5-methyl cytidine, each nucleoside not otherwise annotated is a 2'-deoxyribonucleoside and nucleosides followed by a subscript are defined as shown below:

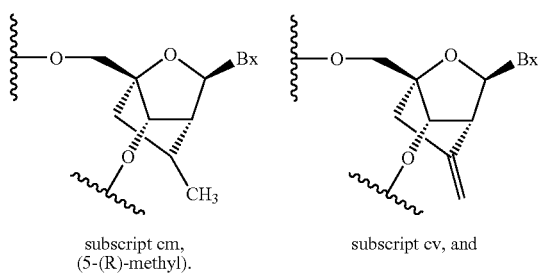

subscript cm, (5-(R)-methyl).  subscript cv, and

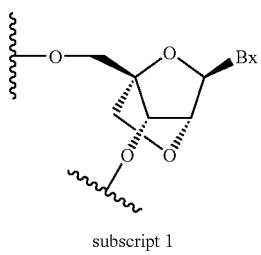

subscript l

ALT and AST levels were measured in mice treated with the antisense oligomers 394425, 411001 and 425453. Serum was analyzed by LabCorp Testing Facility (San Diego, Calif.) and ALT and AST levels in serum were measured relative to saline injected mice. The approximate ALT and AST levels are listed in the table below.

| SEQ ID NO/ ISIS NO | Dose (mg/kg) | ALT (IU/L) | AST (IU/L) | $ED_{50}$ |
|---|---|---|---|---|
| 05/394425 | na | | | 4.8 |
| | 1.9 | 31 | 59 | |
| | 6 | 28 | 51 | |
| | 19 | 55 | 91 | |
| | 60 | 1445 | 1249 | |
| 06/411001 | na | | | 16.0 |
| | 1.9 | 32 | 67 | |
| | 6 | 30 | 66 | |
| | 19 | 25 | 68 | |
| | 60 | 25 | 66 | |
| 06/425453 | na | | | 4.0 |
| | 1.9 | 26 | 45 | |
| | 6 | 30 | 59 | |
| | 19 | 30 | 49 | |
| | 60 | 234 | 164 | |
| Saline | na | 33 | 87 | na. |

All publications, patents, and patent applications referenced herein are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A bicyclic nucleoside having Formula I:

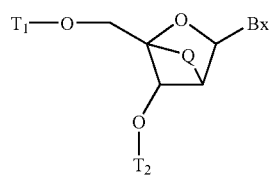

wherein:
   Bx is a heterocyclic base moiety;
   one of $T_1$ and $T_2$ is H or a hydroxyl protecting group and the other of $T_1$ and $T_2$ is H, a hydroxyl protecting group or a reactive phosphorus group;
   Q is $C(q_1)(q_2)C(q_3)(q_4)$, $C(q_1)=C(q_3)$, $C[=C(q_1)(q_2)]-C(q_3)(q_4)$ or $C(q_1)(q_2)-C[=C(q_3)(q_4)]$;
   $q_1$, $q_2$, $q_3$ and $q_4$ are each, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_1$, $SJ_1$, $SOJ_1$, $SO_2J_1$, $NJ_1J_2$, $N_3$, CN, $C(=O)OJ_1$, $C(=O)NJ_1J_2$, $C(=O)J_1$, $O-C(=O)NJ_1J_2$, $N(H)C(=NH)NJ_1J_2$, $N(H)C(=O)NJ_1J_2$ or $N(H)C(=S)NJ_1J_2$;
   wherein each substituted group is, independently, mono or poly substituted with substituent groups independently selected from halogen, $OJ_1$, $SJ_1$, $NJ_1J_2$, $N_3$, CN, $C(=O)OJ_1$, $C(=O)NJ_1J_2$, $C(=O)J_1$, $O-C(=O)NJ_1J_2$, $N(H)C(=O)NJ_1J_2$ or $N(H)C(=S)NJ_1J_2$;
   each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group; and
   wherein when Q is $C(q_1)(q_2)C(q_3)(q_4)$ and one of $q_3$ or $q_4$ is $CH_3$ then at least one of the other of $q_3$ or $q_4$ or one of $q_1$ and $q_2$ is other than H.

2. The bicyclic nucleoside of claim 1 wherein Q is 4'-$C(q_1)(q_2)C(q_3)(q_4)$-2'.

3. The bicyclic nucleoside of claim 1 wherein Q is 4'-$C(q_1)(q_2)$-$C[=C(q_3)(q_4)]$-2'.

4. The bicyclic nucleoside of claim 1 wherein Q is 4'-$C[=C(q_1)(q_2)]$-$C(q_3)(q_4)$-2'.

5. The bicyclic nucleoside of claim 1 wherein Q is 4'-$C(q_1)=C(q_3)$ -2'.

6. The bicyclic nucleoside of claim 1 wherein $q_1$, $q_2$, $q_3$ and $q_4$, where present, are each H.

7. The bicyclic nucleoside of claim 1 wherein one of $q_1$, $q_2$, $q_3$ and $q_4$ is other than H and the remaining of $q_1$, $q_2$, $q_3$ and $q_4$ are each H.

8. The bicyclic nucleoside of claim 1 wherein two of $q_1$, $q_2$, $q_3$ and $q_4$ are other than H and the remaining of $q_1$, $q_2$, $q_3$ and $q_4$ are each H.

9. The bicyclic nucleoside of claim 1 wherein $q_1$, $q_2$, $q_3$ and $q_4$ where present, are each independently, H, halogen, $C_1$-$C_6$ alkyl or $C_1$-$C_6$ alkoxy.

10. The bicyclic nucleoside of claim 1 wherein $q_1$, $q_2$, $q_3$ and $q_4$, where present, are each independently, H, $CH_3$ or F.

11. The bicyclic nucleoside of claim 1 wherein Bx is uracil, thymine, cytosine, 5-methylcytosine, 5-thiazolo-uracil, 5-thiazolo-cytosine, adenine, guanine, 2,6-diaminopurine, or other substituted or unsubstituted purine or pyrimidine.

12. The bicyclic nucleoside of claim 1 wherein $T_1$ is 4,4'-dimethoxytrityl.

13. The bicyclic nucleoside of claim 1 wherein $T_2$ is diisopropyl-cyanoethoxy phosphoramidite or H-phosphonate.

14. The bicyclic nucleoside of claim 1 wherein $T_1$ is 4,4'-dimethoxytrityl and $T_2$ is diisopropylcyanoethoxy phosphoramidite.

15. The bicyclic nucleoside of claim 1, wherein the bicyclic nucleoside has a configuration according to Formula Ia:

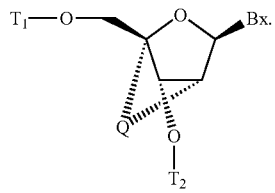

16. The bicyclic nucleoside of claim 15 wherein Q is 4'-C $(q_1)(q_2)C(q_3)(q_4)$-2'.

17. The bicyclic nucleoside of claim 16 wherein Q is 4'-$(CH_2)_2$-2'.

18. The bicyclic nucleoside of claim 16 wherein one of $q_3$ and $q_4$ is F and the remaining of $q_1$, $q_2$, $q_3$ and $q_4$ are each H.

19. The bicyclic nucleoside of claim 15 wherein Q is 4'-C $(q_1)=C(q_3)$-2'.

20. The bicyclic nucleoside of claim 15 wherein Q is 4'-C[=C($q_1$)($q_2$)]-C($q_3$)($q_4$)-2'.

21. The bicyclic nucleoside of claim 15 wherein Q is 4'-C $(q_1)(q_2)$ -C[=C($q_3$)($q_4$)]-2'.

22. The bicyclic nucleoside of claim 21 wherein Q is 4'-$CH_2$—C(=$CH_2$)-2'.

23. An oligomeric compound comprising at least one bicyclic nucleoside having Formula IV:

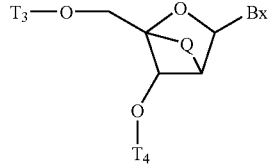

wherein independently for each bicyclic nucleoside having Formula IV:
Bx is a heterocyclic base moiety;
one of $T_3$ and $T_4$ is an internucleoside linking group linking the bicyclic nucleoside having Formula IV to the oligomeric compound and the other of $T_3$ and $T_4$ is H, a hydroxyl protecting group, a linked conjugate group, a 5' or 3'-terminal group or an internucleoside linking group linking the bicyclic nucleoside having Formula IV to the oligomeric compound;
Q is $C(q_1)(q_2)C(q_3)(q_4)$, $C(q_1)=C(q_3)$, $C[=C(q_1)(q_2)]$-C $(q_3)(q_4)$ or $C(q_1)(q_2)$ -C[=C($q_3$)($q_4$)];
$q_1$, $q_2$, $q_3$ and $q_4$ are each, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_1$, $SJ_1$, $SOJ_1$, $SO_2J_1$, $NJ_1J_2$, $N_3$, CN, C(=O) $OJ_1$, C(=O)$NJ_1J_2$, C(=O)$J_1$, O—C(=O)$NJ_1J_2$, N(H) C(=NH)$NJ_1J_2$, N(H)C(=O)$NJ_1J_2$ or N(H)C(=S) $NJ_1J_2$;
wherein each substituted group is, independently, mono or poly substituted with substituent groups independently selected from halogen, $C_1$-$C_6$ alkyl, $C_2$-$C_6$ alkenyl, $C_2$-$C_6$ alkynyl, $OJ_1$, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O)$NJ_1J_2$ or N(H)C(=S)$NJ_1J_2$;
each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group; and
wherein when Q is $C(q_1)(q_2)C(q_3)(q_4)$ and one of $q_3$ or $q_4$ is $CH_3$ then at least one of the other of $q_3$ or $q_4$ or one of $q_1$ and $q_2$ is other than H.

24. The oligomeric compound of claim 23 wherein for each bicyclic nucleoside having Formula IV, Q is 4'-C($q_1$)($q_2$)C $(q_3)(q_4)$ -2'.

25. The oligomeric compound of claim 23 wherein for each bicyclic nucleoside having Formula IV, Q is 4'-C($q_1$)($q_2$)-C[=C($q_3$)($q_4$)]-2'.

26. The oligomeric compound of claim 23 wherein for each bicyclic nucleoside having Formula IV, Q is 4'C[=C($q_1$) ($q_2$)]-C($q_3$)($q_4$)-2'.

27. The oligomeric compound of claim 23 wherein for each bicyclic nucleoside having Formula IV, Q is 4'-C($q_1$)=C($q_3$)- 2'.

28. The oligomeric compound of claim 23 wherein for each bicyclic nucleoside having Formula IV $q_1$, $q_2$, $q_3$ and $q_4$, where present, are each H.

29. The oligomeric compound of claim 23 wherein, independently, for each bicyclic nucleoside having Formula IV one of $q_1$, $q_2$, $q_3$ and $q_4$ is other than H and the remaining of $q_1$, $q_2$, $q_3$ and $q_4$ are each H.

30. The oligomeric compound of claim 23 wherein, independently, for each bicyclic nucleoside having Formula IV two of $q_1$, $q_2$, $q_3$ and $q_4$ are other than H and the remaining of $q_1$, $q_2$, $q_3$ and $q_4$ are each H.

31. The oligomeric compound of claim 23 wherein, independently, for each bicyclic nucleoside having Formula IV $q_1$, $q_2$, $q_3$ and $q_4$ are each, independently, H, halogen, $C_1$-$C_6$ alkyl or $C_1$-$C_6$ alkoxy.

32. The oligomeric compound of claim 23 wherein, independently, for each bicyclic nucleoside having Formula IV $q_1$, $q_2$, $q_3$ and $q_4$ are each, independently, H, $CH_3$ or F.

33. The oligomeric compound of claim 23 wherein each Bx is uracil, thymine, cytosine, 5-methylcytosine, 5-thiazolo-uracil, 5-thiazolo-cytosine, adenine, guanine, 2,6-diaminopurine, or other substituted or unsubstituted purine or pyrimidine.

34. The oligomeric compound of claim 23 wherein at least one of $T_3$ and $T_4$ is a 5' or 3'-terminal group.

35. The oligomeric compound of claim 23 wherein each bicyclic nucleoside having Formula IV has the configuration of Formula IVa:

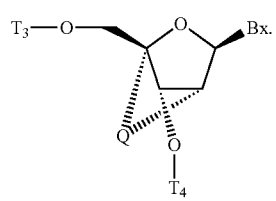

36. The oligomeric compound of claim 35 wherein for each bicyclic nucleoside having Formula IVa, Q is 4'-C($q_1$)($q_2$)C $(q_3)(q_4)$ -2'.

37. The oligomeric compound of claim 36 wherein for each bicyclic nucleoside having Formula IVa, Q is 4'-$(CH_2)_2$-2'.

38. The oligomeric compound of claim 36 wherein for each bicyclic nucleoside having Formula IVa, Q is 4'-$CH_2$—CHF-2'.

39. The oligomeric compound of claim 35 wherein for each bicyclic nucleoside having Formula IVa, Q is 4'-$C(q_1)$=$C(q_3)$-2'.

40. The oligomeric compound of claim 35 wherein for each bicyclic nucleoside having Formula IVa, Q is 4'-C[=$C(q_1)(q_2)$]-$C(q_3)(q_4)$-2'.

41. The oligomeric compound of claim 35 wherein for each bicyclic nucleoside having Formula IVa, Q is 4'-$C(q_1)(q_2)$-C[=$C(q_3)(q_4)$]-2'.

42. The oligomeric compound of claim 41 wherein for each bicyclic nucleoside having Formula IVa, Q is 4'-$CH_2$—C(=$CH_2$)-2'.

43. The oligomeric compound of claim 23 wherein each internucleoside linking group is, independently, a phosphodiester or a phosphorothioate.

44. The oligomeric compound of claim 23 comprising at least one region of at least two contiguous bicyclic nucleosides having said formula located at either the 3' or the 5'-end of the oligomeric compound.

45. The oligomeric compound of claim 23 comprising a gapped oligomeric compound having at least two regions, each region comprising from 1 to about 5 contiguous bicyclic nucleosides having Formula IV, wherein one of said regions of bicyclic nucleosides having Formula IV is located externally at the 5'-end and the other of said regions is located externally at the 3'-end and wherein the two external regions are separated by an internal region comprising from about 6 to about 14 monomeric subunits independently selected from nucleosides and modified nucleosides.

46. The oligomeric compound of claim 23 comprising from about 8 to about 40 monomers in length.

47. The oligomeric compound of claim 23 comprising from about 8 to about 20 monomers in length.

48. A method for inhibiting gene expression comprising contacting a cell with an oligomeric compound of claim 23, wherein said oligomeric compound comprises from about 8 to about 40 monomeric subunits and is complementary to a target RNA.

49. The method of claim 48 wherein said cell is in an animal.

50. The method of claim 48 wherein said cell is in a human.

51. The method of claim 48 wherein said target RNA is selected from mRNA, pre-mRNA and micro RNA.

52. The method of claim 48 wherein said target RNA is mRNA.

53. The method of claim 48 wherein said target RNA is human mRNA.

54. The method of claim 48 wherein said target RNA is cleaved thereby inhibiting its function.

55. The method of claim 48 further comprising detecting the levels of target RNA.

* * * * *